US011691977B2

(12) United States Patent
Hoenke et al.

(10) Patent No.: US 11,691,977 B2
(45) Date of Patent: *Jul. 4, 2023

(54) CYCLIC ETHER DERIVATIVES OF PYRAZOLO[1,5-A]PYRIMIDINE-3-CARBOXYAMIDE

(71) Applicant: Boehringer Ingelheim International GmbH, Ingelheim am Rhein (DE)

(72) Inventors: Christoph Hoenke, Biberach an der Riss (DE); Barbara Bertani, Castiglione delle Stiviere (IT); Marco Ferrara, San Donato Milanese (IT); Giacomo Fossati, Monza (IT); Sara Frattini, Castelleone (IT); Riccardo Giovannini, Biberach an der Riss (DE); Scott Hobson, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 252 days.

This patent is subject to a terminal disclaimer.

(21) Appl. No.: 17/075,091

(22) Filed: Oct. 20, 2020

(65) Prior Publication Data

US 2021/0032259 A1 Feb. 4, 2021

Related U.S. Application Data

(60) Continuation of application No. 16/600,965, filed on Oct. 14, 2019, now Pat. No. 10,875,867, which is a division of application No. 15/865,695, filed on Jan. 9, 2018, now Pat. No. 10,479,794, which is a division of application No. 15/291,316, filed on Oct. 12, 2016, now Pat. No. 10,023,575.

(30) Foreign Application Priority Data

Oct. 13, 2015 (EP) ..................................... 15189600

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC ............................ C07D 487/04; A61K 31/519
USPC ...................................................... 514/259.3
See application file for complete search history.

(56) References Cited

U.S. PATENT DOCUMENTS

| 6,998,402 | B2 | 2/2006 | Niewohner et al. |
| 8,163,759 | B2 | 4/2012 | Tanimoto et al. |
| 8,188,097 | B2 | 5/2012 | Moritani et al. |
| 8,637,526 | B2 | 1/2014 | Blaney et al. |
| 8,921,380 | B2 | 12/2014 | Tanimoto et al. |
| 9,085,584 | B2 | 7/2015 | Giovannini et al. |
| 10,479,794 | B2 * | 11/2019 | Hoenke ..................... A61P 3/00 |
| 10,875,867 | B2 * | 12/2020 | Hoenke ................... A61P 21/02 |
| 2007/0161628 | A1 | 7/2007 | Bernard |
| 2009/0069298 | A1 | 3/2009 | Moritani et al. |
| 2009/0215746 | A1 | 8/2009 | Yasuma et al. |
| 2009/0258867 | A1 | 10/2009 | Tanimoto et al. |
| 2010/0035882 | A1 | 2/2010 | Ellinghaus et al. |
| 2012/0022043 | A1 | 1/2012 | Blaney et al. |
| 2012/0202992 | A1 | 8/2012 | Tanimoto et al. |
| 2014/0045856 | A1 | 2/2014 | Giovannini et al. |
| 2014/0045857 | A1 | 2/2014 | Giovannini et al. |
| 2014/0107099 | A1 | 4/2014 | Blaney et al. |
| 2016/0159808 | A1 | 6/2016 | Kawasaki |
| 2016/0244456 | A1 | 8/2016 | Blaney et al. |
| 2016/0264536 | A1 | 9/2016 | Seto et al. |

FOREIGN PATENT DOCUMENTS

| JP | 2008007493 A | 1/2008 |
| JP | 2008285464 A | 11/2008 |
| JP | 2012507569 A | 3/2012 |
| JP | 2015523406 A | 8/2015 |
| JP | 2017095366 A | 6/2017 |
| WO | 2002068423 A1 | 9/2002 |
| WO | 2005041957 A1 | 5/2005 |
| WO | 2005061497 A1 | 7/2005 |
| WO | 2005063723 A1 | 7/2005 |
| WO | 2005113517 A1 | 12/2005 |
| WO | 2006024640 A2 | 3/2006 |
| WO | 2006072612 A2 | 7/2006 |
| WO | 2006072615 A2 | 7/2006 |
| WO | 2006102728 A2 | 10/2006 |
| WO | 2007046548 | 4/2007 |
| WO | 2007121319 A2 | 10/2007 |
| WO | 2008004698 | 1/2008 |
| WO | 2008043461 A2 | 4/2008 |
| WO | 2010051549 | 5/2010 |
| WO | 2010090716 A1 | 8/2010 |
| WO | 2012021615 A1 | 2/2012 |
| WO | 2012104293 A1 | 8/2012 |
| WO | 2013000924 A1 | 1/2013 |
| WO | 2013034761 A1 | 3/2013 |
| WO | 2014019979 A1 | 2/2014 |

(Continued)

OTHER PUBLICATIONS

Trabanco et al Expert Opinion on therapeutic patents, 2016, 26(8) 933-946 (Year: 2016).*

(Continued)

*Primary Examiner* — Yevgeny Valenrod

(74) *Attorney, Agent, or Firm* — David L. Kershner

(57) ABSTRACT

The invention relates to Spirocyclic ether derivatives of pyrazolo[1,5-a]pyrimidine-3-carboxyamide of general formula (I) which are inhibitors of phosphodiesterase 2, useful in treating central nervous system diseases and other diseases. In addition, the invention relates to processes for preparing pharmaceutical compositions as well as processes for manufacture the compounds according to the invention.

15 Claims, No Drawings

(56) References Cited

FOREIGN PATENT DOCUMENTS

| WO | 2014025651 | A1 | 2/2014 |
|---|---|---|---|
| WO | 2015012328 | | 1/2015 |
| WO | 2015060368 | A1 | 4/2015 |
| WO | 2015096651 | A1 | 7/2015 |

OTHER PUBLICATIONS

Boess, Frank G. et al. "Inhibition of phosphodiesterase 2 increases neuronal cGMP, synaptic plasticity and memory performance" (2004) Neuropharmacology, 47, 1081-1092.

Burdick, K.E et al. "Empirical evidence for discrete neurocognitive subgroups in bipolar disorder: clinical implications" (2014) Psychological Medicine, 44, 3083-3096.

Chakravarty, S. et al., "Kinase inhibitors: A new tool for the treatment of rheumatoid arthritis." Clinical Immunology, 2013, vol. 148, pp. 66-78.

Gooding, Diane C "Spatial working memory performance in patients with schizoaffective psychosis versus schizophrenia: a tale of two disorders?" (2002) Schizophrenia Research, 53, 209-218.

Redrobe, John P. et al. "In vitro and in vivo characterisation of Lu AF64280, a novel, brain penetrant phosphodiesterase (PDE) 2A inhibitor: potential relevance to cognitive deficits in schizophrenia" (2014) Psychopharmacology, 231, 3151-3167.

Reichenberg, Abraham et al. "Neuropsychological Function and Dysfunction in Schizophrenia and Psychotic Affective Disorders" (2009) Schizophrenia Bulletin, vol. 35, No. 5, 1022-1029.

Trabanco, Andres A. et al. "Towards selective phosphodiestiesterase 2A (PDE2A) inhibitors: a patent review (2010-present)" (2016) Expert Opinion on Therapeutic Patents, vol. 26, No. 8, 933-946.

Whang, J. et al., "Bruton's tyrosine kinase inhibitors for the treatment of rheumatoid arthritis." Drug Discovery Today, 2014, pp. 1-5.

\* cited by examiner

CYCLIC ETHER DERIVATIVES OF PYRAZOLO[1,5-A]PYRIMIDINE-3-CARBOXYAMIDE

RELATED APPLICATIONS

This application is a Continuation of co-pending U.S. application Ser. No. 16/600,965, filed Oct. 14, 2019, which is a Divisional of co-pending U.S. application Ser. No. 15/865,695, filed Jan. 9, 2018, which is a Divisional of U.S. application Ser. No. 15/291,316, filed Oct. 10, 2016, now U.S. Pat. No. 10,023,575, which claims priority to EP Application No. 15189600.8 filed Oct. 13, 2015, the content of each of which is incorporated herein by reference in its entirety.

FIELD OF THE INVENTION

The invention relates to cyclic ether derivatives of pyrazolo[1,5-a]pyrimidine-3-carboxyamide of general formula (I) which are inhibitors of phosphodiesterase 2, useful in treating central nervous system diseases and other diseases. In addition, the invention relates to processes for preparing pharmaceutical compositions as well as processes for manufacture the compounds according to the invention.

BACKGROUND OF THE INVENTION

Phosphodiesterase 2 (PDE2) inhibitors are promising therapeutic targets for treatment of cognitive impairment in diseases such as Schizophrenia, Alzheimer's disease and depression. Inhibitors of PDE2 have emerged as potential candidates to improve synaptic plasticity and memory function.

Phosphodiesterases (PDE) are expressed in nearly all mammalian cells. To date eleven families of phosphodiesterases have been identified in mammals. It is well established that PDEs are critically involved in cell signalling. Specifically, PDEs are known to inactivate the cyclic nucleotides cAMP and/or cGMP.

PDE2 hydrolyses both, cGMP and cAMP. It is both abundantly expressed in the brain indicating their relevance in CNS function.

The expression of PDE2 in the hippocampus, the cortex and in the striatum indicate an involvement in the mechanism of learning and memory/cognition. This is further supported by the fact that increased levels of both cGMP and cAMP are involved in the process of short and long term potentiation (LTP) forming. Further data support the procognitive effect of PDE2 and a synergistic effect of PDE2 on cognition. Furthermore, the expression of PDE2 in the nucleus accumbens (part of the striatum), the olfactory bulb, the olfactory tubercle and the amygdala supports additional involvement of PDE2 in the pathophysiology of anxiety and depression. This is supported by in vivo studies.

It is commonly accepted (free drug hypothesis) that unbound or free drug concentration at the site of action is responsible for pharmacological activity in vivo at steady state and, in the absence of active transport, the free drug concentration is the same in any biomembrane.

For drugs with an intended action in the central nervous system (CNS), it is assumed that unbound drug in interstitial spaces (ISF) in the brain is in direct contact or in equilibrium with the site of action. Because cerebrospinal fluid (CSF) is in direct contact with the brain tissue, it is assumed to readily equilibrate with brain interstitial fluid concentration so that CSF concentration is used as a common surrogate measure for drug unbound concentration in pre-clinical pharmacology studies. Accordingly, for compounds with an intended action in the central nervous system it is important that they reach a high CSF concentration and a high CSF to plasma ratio in order to have high pharmacological activity in the CNS.

At steady state and in the absence of active transport, the unbound brain concentration can also be estimated with the experimentally more accessible unbound plasma concentration by measuring the plasma protein binding (PPB) across species.

High membrane permeability and absence of active transport process at the BBB (blood brain barrier) together with plasma/brain tissue binding are recognised as the primary determinant of drug disposition within CNS.

High metabolic stability is desirable in order to achieve significant exposure of a drug within the body.

Several families of PDE2 inhibitors are known. Imidazotriazinones are claimed in WO 2002/068423 for the treatment of e.g. memory deficiency, cognitive disorders, dementia and Alzheimer's disease. Oxindoles are described in WO 2005/041957 for the treatment of dementia. Further inhibitors of PDE2 are known from WO 2007/121319 for the treatment of anxiety and depression, from WO 2013/034761, WO 2012/104293 and WO2013/000924 for the treatment of neurological and psychiatric disorders, from WO 2006/072615, WO 2006/072612, WO 2006/024640 and WO 2005/113517 for the treatment of arthritis, cancer, edema and septic shock, from WO 2005/063723 for the treatment of renal and liver failure, liver dysfunction, restless leg syndrome, rheumatic disorders, arthritis, rhinitis, asthma and obesity, from WO 2005/041957 for the treatment of cancer and thrombotic disorders, from WO 2006/102728 for the treatment of angina pectoris and hypertension from WO 2008/043461 for the treatment of cardiovascular disorders, erectile dysfunction, inflammation and renal failure and from WO 2005/061497 for the treatment of e.g. dementia, memory disorders, cancer and osteoporosis.

Benzodiazepine like PDE2 inhibitors are described in WO 2005/063723 for the general treatment of CNS diseases including anxiety, depression, ADHD, neurodegeneration, Alzheimer's disease and psychosis.

Newer PDE2 inhibitor families are described in WO 2015/096651, WO 2015/060368 and WO 2015/012328.

AIM OF THE INVENTION

It has now been found that compounds of the present invention according to general formula (I) are effective inhibitors of phosphodiesterase 2.

Besides the inhibition property toward phosphodiesterase 2 enzymes, the compounds of the present invention provide further advantageous properties such as high selectivity with regard to PDE 10, low plasma protein binding across species, high CSF to plasma ratio, adequate tissue permeability and high metabolic stability.

For example the compounds of the present invention show low plasma protein binding across species and as a consequence high fraction unbound in plasma, high concentration in cerebrospinal fluid (CSF) and have a high CSF to plasma ratio, which translates in lower efficacious doses of the compounds for disease treatment and as a consequence in further potential advantages such as minimization of side effects. Furthermore, compounds of the present inventions show good metabolic stability both in rodents and non rodents species, good membrane permeability with no active transport at the BBB. In addition the compounds of the present invention have very high IC50 values for PDE 10.

Accordingly, one aspect of the invention refers to compounds according to formula (I), or salts thereof as inhibitors of phosphodiesterase 2.

Another aspect of the invention refers to compounds according to formula (I), or pharmaceutically acceptable salts thereof as inhibitors of phosphodiesterase 2 and reaching high concentrations in cerebrospinal fluid (CSF) and/or having high CSF to plasma ratio.

Another aspect of the invention refers to compounds according to formula (I), or pharmaceutically acceptable salts thereof as inhibitors of phosphodiesterase 2 with low plasma protein binding and thus high fraction unbound across species.

Another aspect of the invention refers to compounds according to formula (I), or pharmaceutically acceptable salts thereof as inhibitors of phosphodiesterase 2 and showing good membrane permeability and low to moderate in vitro efflux.

Another aspect of the invention refers to according to formula (I), or pharmaceutically acceptable salts thereof as inhibitors of phosphodiesterase 2 and showing good metabolic stability.

In a further aspect this invention relates to pharmaceutical compositions, containing at least one compound according to formula (I), or pharmaceutically acceptable salts thereof, optionally together with one or more inert carriers and/or diluents.

A further aspect of the present invention relates to compounds according to formula (I), or pharmaceutically acceptable salts thereof or pharmaceutical compositions comprising compounds according to formula (I), or pharmaceutically acceptable salts thereof for the use in the prevention and/or treatment of disorders associated with PDE2 hyperactivity and/or cAMP and/or cGMP hypofunction.

Another aspect of the invention relates to processes of manufacture of the compounds of the present invention.

A further aspect of the present invention relates to compounds according to formula (I), or pharmaceutically acceptable salts thereof or pharmaceutical compositions comprising compounds according to formula (I), or pharmaceutically acceptable salts thereof for the use in the prevention and/or treatment of diseases or conditions which can be influenced by inhibition of PDE2 hyperactivity and/or cAMP and/or cGMP hypofunction, such as (1) disorders comprising the symptom of cognitive deficiency; (2) organic, including symptomatic, mental disorders, dementia; (3) mental retardation; (4) mood affective disorders; (5) neurotic, stress-related and somatoform disorders including anxiety disorders; (6) behavioural and emotional disorders with onset usually occurring in childhood and adolescence, attention deficit hyperactivity syndrome (ADHD) including Autism spectrum disorders; (7) disorders of psychological development, developmental disorders of scholastic skills; (8) schizophrenia and other psychotic disorders; (9) disorders of adult personality and behaviour; (10) mental and behavioural disorders due to psychoactive substance use; (11) extrapyramidal and movement disorders; (12) episodic and paroxysmal disorders, epilepsy; (13) Systemic atrophies primarily affecting the central nervous system, ataxia; (14) Behavioural syndromes associated with physiological disturbances and physical factors; (15) sexual dysfunction comprising excessive sexual drive; (16) factitious disorders; (17) obsessive-compulsive disorders; (18) depression; (19) neuropsychiatric symptoms (e.g. depressive symptoms in Alzheimer's disease); (20) mixed dementia; (21) cognitive impairment in schizoaffective disorder; (22) cognitive impairment in bipolar disorder and (23) cognitive impairment in major depressive disorder.

In addition, the compounds of the present invention can be used for the treatment, amelioration and/or prevention of cognitive impairment being related to perception, concentration, cognition, learning, attention or memory.

In addition, the compounds of the present invention can be used for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

In addition, the compounds of the present invention can be used for the treatment of Alzheimer's disease.

In addition compounds of the present invention can be used for the treatment of pain disorders, including but not limited to inflammatory, neuropathic and osteoarthritic pain.

In addition, the compounds of the present invention can be used for the treatment of sleep disorders, bipolar disorder, metabolic syndrome, obesity, diabetes mellitus, hyperglycemia, dyslipidemia, impaired glucose tolerance, or a disease of the testes, brain, small intestine, skeletal muscle, heart, lung, thymus or spleen.

Other aims of the present invention will become apparent to the skilled man directly from the foregoing and following remarks.

DETAILED DESCRIPTION

In a first aspect the present invention relates to compounds of general formula (I)

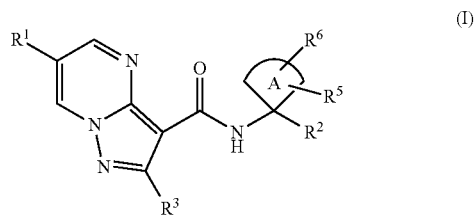

wherein
A is selected from the group $A^a$ consisting of

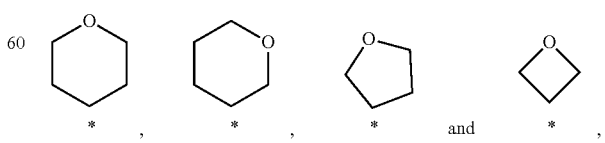

wherein above mentioned groups are substituted with one $R^5$ and one $R^6$;

R¹ is selected from the group R1a consisting of
  halogen, $C_{1-3}$-alkyl- and $C_{3-6}$-cycloalkyl-
    wherein the above mentioned $C_{1-3}$-alkyl-, and $C_{3-6}$-cycloalkyl-groups may optionally be substituted with 1 to 5 substituents independently selected from the group consisting of halogen, NC— and HO—;
R² is selected from the group $R^{2a}$ consisting of
  aryl and heteroaryl,
    wherein the above mentioned aryl and heteroaryl-groups may optionally be substituted with 1 to 5 substituents R⁴;
R³ is selected from the group $R^{3a}$ consisting of
  H— and $C_{1-3}$-alkyl-,
    wherein the above mentioned $C_{1-3}$-alkyl-groups may optionally be substituted with 1 to 7 substituents independently from each other selected from the group consisting of halogen;
R⁴ is independently from each other selected from the group $R^{4a}$ consisting of
  halogen, NC—, HO—, $C_{1-4}$-alkyl- and $C_{1-3}$-alkyl-O—
    wherein the above mentioned $C_{1-4}$-alkyl- and $C_{1-3}$-alkyl-O-groups may optionally be substituted with 1 to 5 substituents independently selected from the group consisting of HO— and F—;
R⁵ is selected from the group $R^{5a}$ consisting of
  H—, halogen, NC—, HO— and $C_{1-3}$-alkyl-,
    wherein the above mentioned $C_{1-3}$-alkyl-group may optionally be substituted with 1 to 5 substituents independently selected from the group consisting of HO— and F—
  or R⁵ and R⁶ together form an group O=;
R⁶ is selected from the group $R^{6a}$ consisting of
  H—, halogen, NC—, HO— and $C_{1-3}$-alkyl-,
    wherein the above mentioned $C_{1-3}$-alkyl-group may optionally be substituted with 1 to 5 substituents independently selected from the group consisting of HO— and F—
  or R⁵ and R⁶ together form a group O=;
or a salt thereof.

Unless otherwise stated, the groups, residues, and substituents, particularly R¹, R², R³, R⁴ and R⁵ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^b$ consisting of

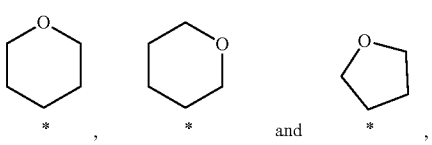 [SMILES: C1CCOCC1 ; C1CCOCC1 ; C1CCOC1]

wherein above mentioned groups are substituted with one R⁵ and one R⁶.

In a further embodiment of the present invention
A is selected from the group A consisting of

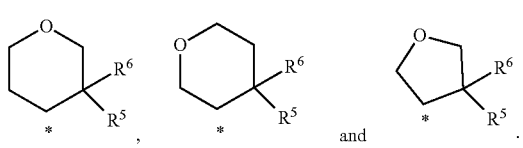

In a further embodiment of the present invention
A is selected from the group $A^d$ consisting of

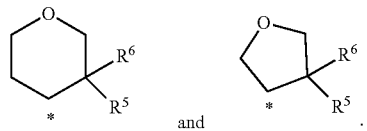

In a further embodiment of the present invention
A is selected from the group $A^e$ consisting of

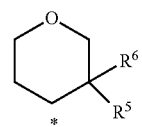

In a further embodiment of the present invention
R¹ is selected from the group $R^1 b$ consisting of
  F—, Cl—, $C_{1-3}$-alkyl- and $C_{3-6}$-cycloalkyl-,
    wherein the above mentioned $C_{1-3}$-alkyl- and $C_{3-6}$-cycloalkyl-groups may optionally be substituted with 1 to 3 substituents independently selected from the group consisting of F—.

In a further embodiment of the present invention
R¹ is selected from the group R¹ consisting of
  F—, H₃C— and cyclopropyl-.

In a further embodiment of the present invention
R¹ is selected from the group $R^1 d$ consisting of
  H₃C— and cyclopropyl-.

In a further embodiment of the present invention
R² is selected from the group $R^{2b}$ consisting of
  quinolinyl, phenyl and pyridynyl,
    wherein the above mentioned quinoline, phenyl and pyridyl-groups may optionally be substituted with 1 to 5 substituents R⁴.

In a further embodiment of the present invention
R² is selected from the group $R^{2c}$ consisting of
  phenyl and pyridyl,
    wherein the above mentioned phenyl and pyridyl-groups may optionally be substituted with 1 to 2 substituents R⁴.

In a further embodiment of the present invention
R² is selected from the group $R^{2d}$ being

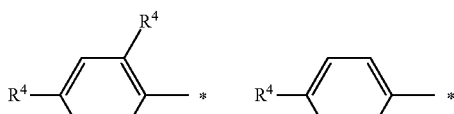
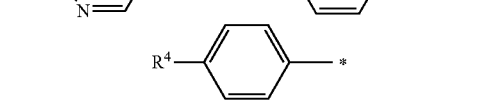

In a further embodiment of the present invention R² is selected from the group R²ᵉ being

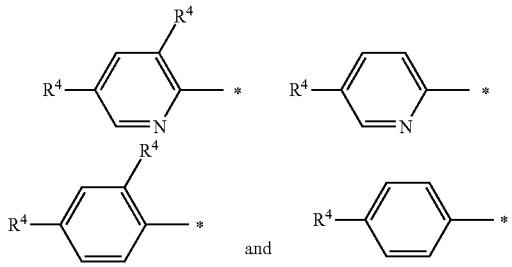

and

In a further embodiment of the present invention R² is selected from the group R²ᶠ being

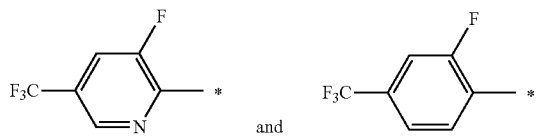

and

In a further embodiment of the present invention R³ is selected from the group R³ᵇ consisting of
H—, H₃C—, F₃C—, F₂HC—, FH₂C— and F₃C—.

In a further embodiment of the present invention R³ is selected from the group R³ᶜ consisting of
H— and H₃C—.

In a further embodiment of the present invention R³ is selected from the group R³ᵈ being H—.

In a further embodiment of the present invention R⁴ is independently from each other selected from the group R⁴ᵇ consisting of halogen, C₁₋₄-alkyl- and C₁₋₃-alkyl-O—
wherein the above mentioned C₁₋₄-alkyl- and C₁₋₃-alkyl-O-groups may optionally be substituted with 1 to 5 substituents independently selected from the group consisting of HO—, and F—.

In a further embodiment of the present invention R⁴ is independently from each other selected from the group R⁴ᶜ consisting of halogen, C₁₋₃-alkyl-, F₃C—O—, F₂HC—O—, FH₂C—O— and H₃C—O—,
wherein the above mentioned C₁₋₃-alkyl-groups may optionally be substituted with 1 to 5 F—.

In a further embodiment of the present invention R⁴ is independently from each other selected from the group R⁴ᵈ consisting of F, Cl, Br, F₃C—, F₂HC—, FH₂C—, H₃C—, F₃C—O—, F₂HC—O—, FH₂C—O— and H₃C—O—.

In a further embodiment of the present invention R⁴ is independently from each other selected from the group R⁴ᵉ consisting of F, Cl, F₃C—, F₃C—O— and H₃C—O—.

In a further embodiment of the present invention R⁴ is independently from each other selected from the group R⁴ᶠ consisting of F and F₃C—.

In a further embodiment of the present invention R⁵ is selected from the group R⁵ᵇ consisting of
H—, HO— and C₁₋₂-alkyl-,
wherein the above mentioned C₁₋₂-alkyl-group may optionally be substituted with 1 to 5 F—,
or R⁵ and R⁶ together form an group O=.

In a further embodiment of the present invention R⁵ is selected from the group R⁵ᶜ consisting of
H— and HO—.

In a further embodiment of the present invention R⁵ is selected from the group R⁵ᵈ being
HO—.

In a further embodiment of the present invention R⁶ is selected from the group R⁶ᵇ consisting of
H— and C₁₋₂-alkyl-,
wherein the above mentioned C₁₋₂-alkyl-group may optionally be substituted with 1 to 5 F—,
or R⁵/R⁶ together form a group O=.

In a further embodiment of the present invention R⁶ is selected from the group R⁶ᶜ consisting of
H and H₃C—,
wherein the above mentioned methyl-group may optionally be substituted with 1 to 3 F—.

In a further embodiment of the present invention R⁶ is selected from the group R⁶ᵈ consisting of
H— and H₃C—.

Each $A^x$, $R^{1x}$, $R^{2x}$, $R^{3x}$, $R^{4x}$, $R^{5x}$ and $R^{6x}$ represents a characterized, individual embodiment for the corresponding substituent as described above. Thus given the above definitions, individual embodiments of the first aspect of the invention are fully characterized by the term ($A^x$, $R^{1x}$, $R^{2x}$, $R^{3x}$, $R^{4x}$, $R^{5x}$ and $R^{6x}$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows such embodiments E-1 to E-39 of the invention that are considered preferred. Embodiment E-39, represented by the entries in the last row of Table 1, is the most preferred embodiment.

TABLE 1

Embodiments E-1 to E-39 of the invention

| | $A^x$ | $R^{1x}$ | $R^{2x}$ | $R^{3x}$ | $R^{4x}$ | $R^{5x}$ | $R^{6x}$ |
|---|---|---|---|---|---|---|---|
| E-1 | $A^a$ | $R^{1a}$ | $R^{2a}$ | $R^{3a}$ | $R^{4b}$ | $R^{5a}$ | $R^{6a}$ |
| E-2 | $A^a$ | $R^{1a}$ | $R^{2a}$ | $R^{3b}$ | $R^{4b}$ | $R^{5a}$ | $R^{6a}$ |
| E-3 | $A^a$ | $R^{1b}$ | $R^{2b}$ | $R^{3b}$ | $R^{4c}$ | $R^{5a}$ | $R^{6a}$ |
| E-4 | $A^a$ | $R^{1c}$ | $R^{2b}$ | $R^{3b}$ | $R^{4d}$ | $R^{5a}$ | $R^{6a}$ |
| E-5 | $A^a$ | $R^{1c}$ | $R^{2b}$ | $R^{3c}$ | $R^{4e}$ | $R^{5b}$ | $R^{6b}$ |
| E-6 | $A^b$ | $R^{1b}$ | $R^{2b}$ | $R^{3b}$ | $R^{4b}$ | $R^{5a}$ | $R^{6a}$ |
| E-7 | $A^b$ | $R^{1c}$ | $R^{2b}$ | $R^{3c}$ | $R^{4e}$ | $R^{5b}$ | $R^{6b}$ |
| E-8 | $A^c$ | $R^{1c}$ | $R^{2b}$ | $R^{3b}$ | $R^{4b}$ | $R^{5b}$ | $R^{6b}$ |
| E-9 | $A^c$ | $R^{1c}$ | $R^{2b}$ | $R^{3c}$ | $R^{4e}$ | $R^{5b}$ | $R^{6b}$ |
| E-10 | $A^c$ | $R^{1c}$ | $R^{2c}$ | $R^{3b}$ | $R^{4c}$ | $R^{5b}$ | $R^{6b}$ |
| E-11 | $A^c$ | $R^{1d}$ | $R^{2c}$ | $R^{3c}$ | $R^{4d}$ | $R^{5b}$ | $R^{6b}$ |
| E-12 | $A^c$ | $R^{1d}$ | $R^{2c}$ | $R^{3d}$ | $R^{4e}$ | $R^{5b}$ | $R^{6b}$ |
| E-13 | $A^c$ | $R^{1d}$ | $R^{2c}$ | $R^{3d}$ | $R^{4f}$ | $R^{5c}$ | $R^{6c}$ |
| E-14 | $A^c$ | $R^{1d}$ | $R^{2d}$ | $R^{3b}$ | $R^{4c}$ | $R^{5b}$ | $R^{6b}$ |
| E-15 | $A^c$ | $R^{1d}$ | $R^{2d}$ | $R^{3c}$ | $R^{4d}$ | $R^{5b}$ | $R^{6b}$ |
| E-16 | $A^c$ | $R^{1d}$ | $R^{2d}$ | $R^{3c}$ | $R^{4f}$ | $R^{5d}$ | $R^{6d}$ |
| E-17 | $A^c$ | $R^{1d}$ | $R^{2d}$ | $R^{3d}$ | $R^{4e}$ | $R^{5b}$ | $R^{6b}$ |
| E-18 | $A^c$ | $R^{1d}$ | $R^{2d}$ | $R^{3d}$ | $R^{4f}$ | $R^{5c}$ | $R^{6c}$ |
| E-19 | $A^c$ | $R^{1d}$ | $R^{2e}$ | $R^{3b}$ | $R^{4b}$ | $R^{5b}$ | $R^{6b}$ |
| E-20 | $A^c$ | $R^{1d}$ | $R^{2e}$ | $R^{3b}$ | $R^{4b}$ | $R^{5c}$ | $R^{6c}$ |
| E-21 | $A^c$ | $R^{1d}$ | $R^{2e}$ | $R^{3c}$ | $R^{4d}$ | $R^{5b}$ | $R^{6b}$ |
| E-22 | $A^c$ | $R^{1d}$ | $R^{2e}$ | $R^{3c}$ | $R^{4d}$ | $R^{5c}$ | $R^{6c}$ |
| E-23 | $A^c$ | $R^{1d}$ | $R^{2e}$ | $R^{3c}$ | $R^{4e}$ | $R^{5b}$ | $R^{6b}$ |
| E-24 | $A^c$ | $R^{1d}$ | $R^{2e}$ | $R^{3c}$ | $R^{4e}$ | $R^{5c}$ | $R^{6c}$ |
| E-25 | $A^c$ | $R^{1d}$ | $R^{2e}$ | $R^{3d}$ | $R^{4e}$ | $R^{5b}$ | $R^{6b}$ |
| E-26 | $A^c$ | $R^{1d}$ | $R^{2e}$ | $R^{3d}$ | $R^{4e}$ | $R^{5c}$ | $R^{6c}$ |
| E-27 | $A^c$ | $R^{1d}$ | $R^{2f}$ | $R^{3c}$ | — | $R^{5d}$ | $R^{6d}$ |
| E-28 | $A^c$ | $R^{1d}$ | $R^{2f}$ | $R^{3d}$ | — | $R^{5d}$ | $R^{6d}$ |
| E-29 | $A^d$ | $R^{1c}$ | $R^{2c}$ | $R^{3b}$ | $R^{4d}$ | $R^{5b}$ | $R^{6b}$ |
| E-30 | $A^d$ | $R^{1c}$ | $R^{2d}$ | $R^{3b}$ | $R^{4e}$ | $R^{5c}$ | $R^{6c}$ |
| E-31 | $A^d$ | $R^{1c}$ | $R^{2e}$ | $R^{3c}$ | $R^{4e}$ | $R^{5d}$ | $R^{6d}$ |
| E-32 | $A^d$ | $R^{1d}$ | $R^{2f}$ | $R^{3c}$ | — | $R^{5d}$ | $R^{6d}$ |
| E-33 | $A^e$ | $R^{1c}$ | $R^{2c}$ | $R^{3b}$ | $R^{4d}$ | $R^{5b}$ | $R^{6b}$ |

TABLE 1-continued

Embodiments E-1 to E-39 of the invention

| | $A^x$ | $R^{1x}$ | $R^{2x}$ | $R^{3x}$ | $R^{4x}$ | $R^{5x}$ | $R^{6x}$ |
|---|---|---|---|---|---|---|---|
| E-34 | $A^e$ | $R^{1c}$ | $R^{2d}$ | $R^{3b}$ | $R^{4e}$ | $R^{5c}$ | $R^{6c}$ |
| E-35 | $A^e$ | $R^{1c}$ | $R^{2e}$ | $R^{3c}$ | $R^{4e}$ | $R^{5d}$ | $R^{6d}$ |
| E-36 | $A^e$ | $R^{1c}$ | $R^{2f}$ | $R^{3b}$ | — | $R^{5b}$ | $R^{6b}$ |
| E-37 | $A^e$ | $R^{1d}$ | $R^{2f}$ | $R^{3c}$ | — | $R^{5c}$ | $R^{6c}$ |
| E-38 | $A^e$ | $R^{1d}$ | $R^{2f}$ | $R^{3c}$ | — | $R^{5d}$ | $R^{6d}$ |
| E-39 | $A^e$ | $R^{1d}$ | $R^{2f}$ | $R^{3d}$ | — | $R^{5d}$ | $R^{6d}$ |

Accordingly, for example E-1 covers compounds of formula (I), wherein
A is selected from the group $A^a$ consisting of

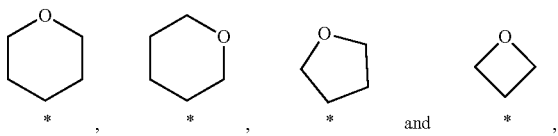

wherein above mentioned groups are substituted with one $R^5$ and one $R^6$;
$R^1$ is selected from the group Ria consisting of
halogen, $C_{1-3}$-alkyl- and $C_{3-6}$-cycloalkyl-
wherein the above mentioned $C_{1-3}$-alkyl-, and $C_{3-6}$-cycloalkyl-groups may optionally be substituted with 1 to 5 substituents independently selected from the group consisting of halogen, NC— and HO—;
$R^2$ is selected from the group $R^{2a}$ consisting of
aryl and heteroaryl,
wherein the above mentioned aryl and heteroaryl-groups may optionally be substituted with 1 to 5 substituents $R^4$;
$R^3$ is selected from the group $R^{3a}$ consisting of
H— and $C_{1-3}$-alkyl-,
wherein the above mentioned $C_{1-3}$-alkyl-groups may optionally be substituted with 1 to 7 substituents independently from each other selected from the group consisting of halogen;
$R^4$ is independently from each other selected from the group $R^{4b}$ consisting of halogen, $C_{1-4}$-alkyl- and $C_{1-3}$-alkyl-O—
wherein the above mentioned $C_{1-4}$-alkyl- and $C_{1-3}$-alkyl-O-groups may optionally be substituted with 1 to 5 substituents independently selected from the group consisting of HO—, and F—;
$R^5$ is selected from the group $R^{5a}$ consisting of
H—, halogen, NC—, HO— and $C_{1-3}$-alkyl-,
wherein the above mentioned $C_{1-3}$-alkyl-group may optionally be substituted with 1 to 5 substituents independently selected from the group consisting of HO— and F—
or $R^5$ and $R^6$ together form an group O=;
$R^6$ is selected from the group $R^{6a}$ consisting of
H—, halogen, NC—, HO— and $C_{1-3}$-alkyl-,
wherein the above mentioned $C_{1-3}$-alkyl-group may optionally be substituted with 1 to 5 substituents independently selected from the group consisting of HO— and F—
or $R^5$ and $R^6$ together form a group O=;
or a salt thereof.

Accordingly, for example E-5 covers compounds of formula (I), wherein
A is selected from the group $A^a$ consisting of

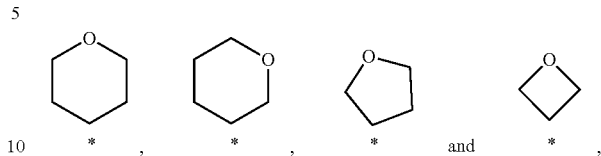

wherein above mentioned groups are substituted with one $R^5$ and one $R^6$;
$R^2$ is selected from the group $R^{2b}$ consisting of quinolinyl, phenyl and pyridynyl,
wherein the above mentioned quinoline, phenyl and pyridyl-groups may optionally be substituted with 1 to 5 substituents $R^4$;
$R^3$ is selected from the group $R^{3c}$ consisting of
H— and $H_3C$—;
$R^4$ is independently from each other selected from the group $R^{4e}$ consisting of F, Cl, $F_3C$—, $F_3C$—O— and $H_3C$—O—;
$R^5$ is selected from the group $R^{5b}$ consisting of
H—, HO— and $C_{1-2}$-alkyl-,
wherein the above mentioned $C_{1-2}$-alkyl-group may optionally be substituted with 1 to 5 F—,
or $R^5$ and $R^6$ together form an group O=:
$R^6$ is selected from the group $R^{6b}$ consisting of
H— and $C_{1-2}$-alkyl-,
wherein the above mentioned $C_{1-2}$-alkyl-group may optionally be substituted with 1 to 5 F—,
or $R^5/R^6$ together form a group O=;
or a salt thereof.

Accordingly, for example E-39 covers compounds of formula (I), wherein
A is selected from the group $A^e$ consisting of

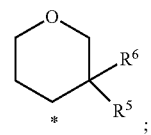

$R^1$ is selected from the group Rid consisting of
$H_3C$— and cyclopropyl-;
$R^2$ is selected from the group $R^{2f}$ being

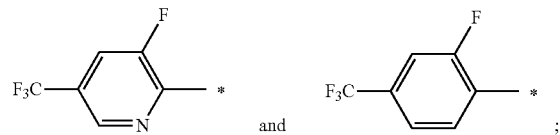

$R^3$ is selected from the group $R^{3d}$ being H—;
$R^5$ is selected from the group $R^{5d}$ being
HO—;
$R^6$ is selected from the group $R^{6d}$ consisting of
H— and methyl-;
or a salt thereof.

Further preferred are the following compounds listed in Table 2:

| No. | Structure |
|---|---|
| I | 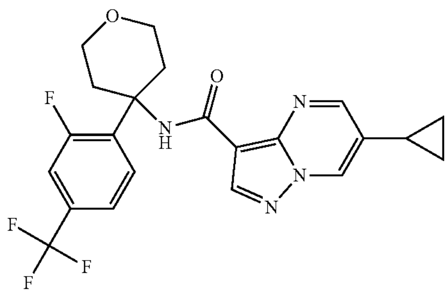 [SMILES: O=C(NC1(c2ccc(C(F)(F)F)cc2F)CCOCC1)c1cnn2cc(C3CC3)cnc12] |
| II | 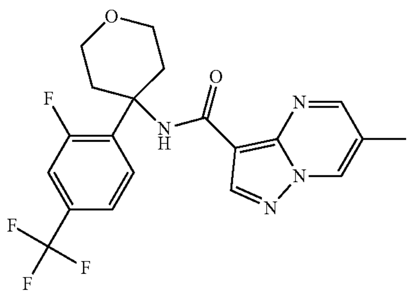 [SMILES: Cc1cnc2c(C(=O)NC3(c4ccc(C(F)(F)F)cc4F)CCOCC3)cnn2c1] |
| III | 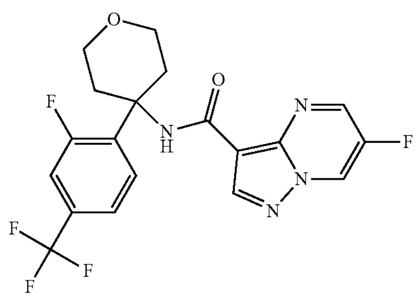 [SMILES: O=C(NC1(c2ccc(C(F)(F)F)cc2F)CCOCC1)c1cnn2cc(F)cnc12] |
| IV | 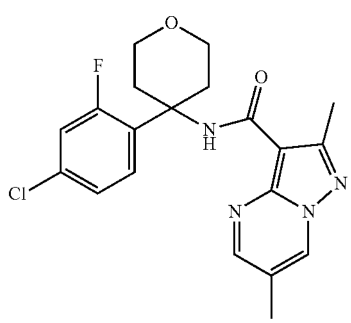 [SMILES: Cc1cnc2c(C(=O)NC3(c4ccc(Cl)cc4F)CCOCC3)c(C)nn2c1] |
| V | 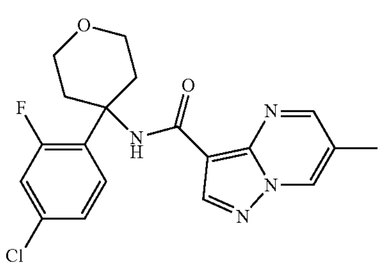 [SMILES: Cc1cnc2c(C(=O)NC3(c4ccc(Cl)cc4F)CCOCC3)cnn2c1] |
| VI | |
| VII | |
| VIII | |
| IX | |
| X | |

| No. | Structure |
|---|---|
| XI | 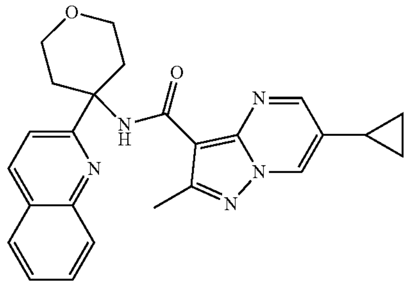 [SMILES: Cc1nn2cc(C3CC3)cnc2c1C(=O)NC1(c2ccc3ccccc3n2)CCOCC1] |
| XII | 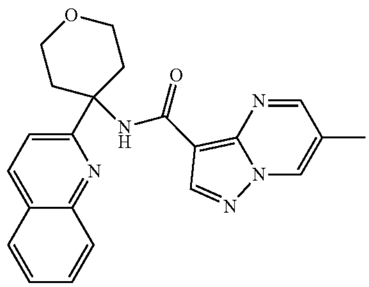 [SMILES: Cc1cnc2c(C(=O)NC3(c4ccc5ccccc5n4)CCOCC3)cnn2c1] |
| XIII | 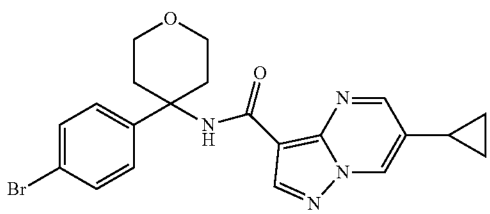 [SMILES: O=C(NC1(c2ccc(Br)cc2)CCOCC1)c1cnn2cc(C3CC3)cnc12] |
| XIV | 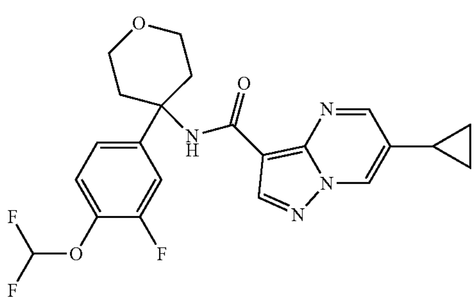 [SMILES: O=C(NC1(c2ccc(OC(F)F)c(F)c2)CCOCC1)c1cnn2cc(C3CC3)cnc12] |
| XV | 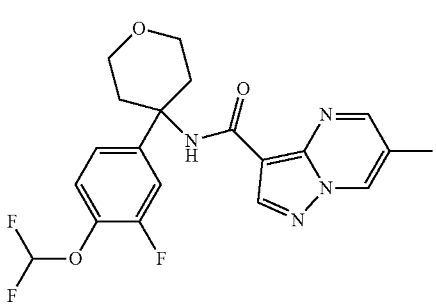 [SMILES: Cc1cnc2c(C(=O)NC3(c4ccc(OC(F)F)c(F)c4)CCOCC3)cnn2c1] |
| XVI | 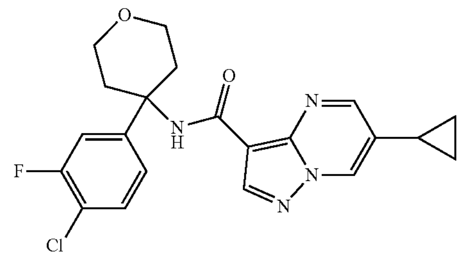 [SMILES: O=C(NC1(c2ccc(Cl)c(F)c2)CCOCC1)c1cnn2cc(C3CC3)cnc12] |
| XVII | 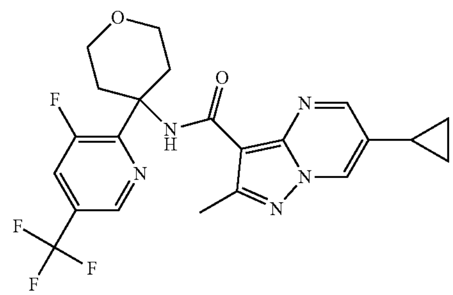 [SMILES: Cc1nn2cc(C3CC3)cnc2c1C(=O)NC1(c2ncc(C(F)(F)F)cc2F)CCOCC1] |
| XVIII | 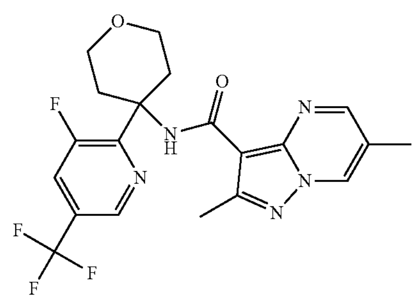 [SMILES: Cc1cnc2c(C(=O)NC3(c4ncc(C(F)(F)F)cc4F)CCOCC3)c(C)nn2c1] |
| XIX | 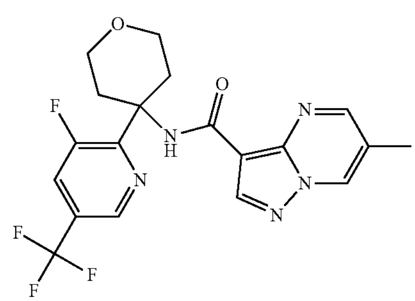 [SMILES: Cc1cnc2c(C(=O)NC3(c4ncc(C(F)(F)F)cc4F)CCOCC3)cnn2c1] |
| XX | 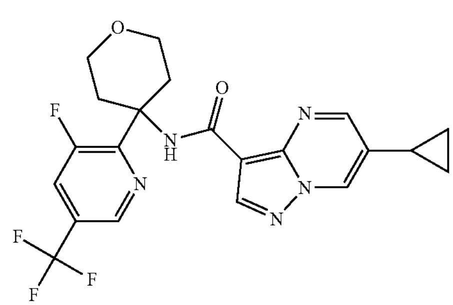 [SMILES: O=C(NC1(c2ncc(C(F)(F)F)cc2F)CCOCC1)c1cnn2cc(C3CC3)cnc12] |

| No. | Structure |
|---|---|
| XXI | 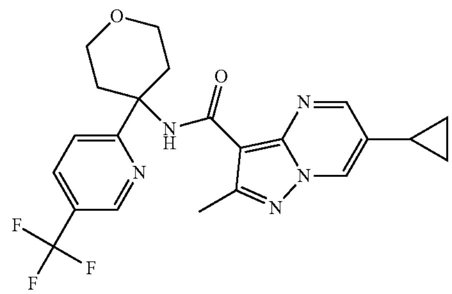 [SMILES: Cc1nn2cc(C3CC3)cnc2c1C(=O)NC1(c2ccc(C(F)(F)F)cn2)CCOCC1] |
| XXII | 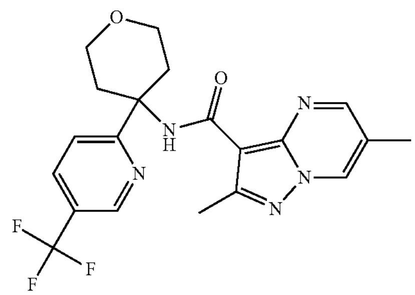 [SMILES: Cc1cnc2c(C(=O)NC3(c4ccc(C(F)(F)F)cn4)CCOCC3)c(C)nn2c1] |
| XXIII | 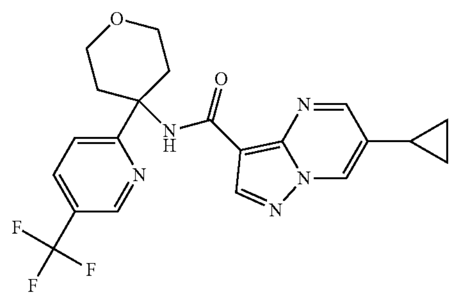 [SMILES: O=C(NC1(c2ccc(C(F)(F)F)cn2)CCOCC1)c1cnn2cc(C3CC3)cnc12] |
| XXIV | 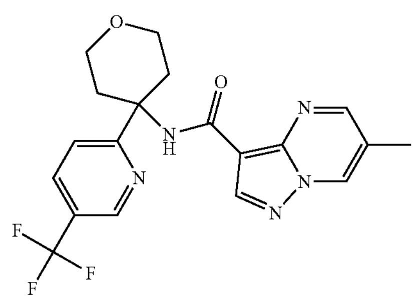 [SMILES: Cc1cnc2c(C(=O)NC3(c4ccc(C(F)(F)F)cn4)CCOCC3)cnn2c1] |
| XXV | 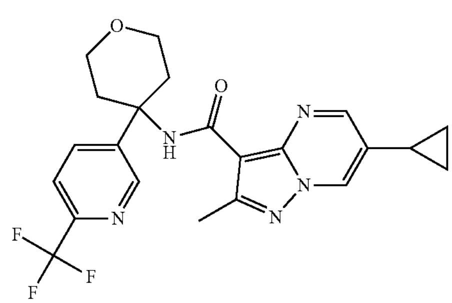 [SMILES: Cc1nn2cc(C3CC3)cnc2c1C(=O)NC1(c2ccc(C(F)(F)F)nc2)CCOCC1] |
| XXVI | |
| XXVII | |
| XXVIII | |
| XXIX | |
| XXX | |

-continued

| No. | Structure |
|---|---|
| XXXI | 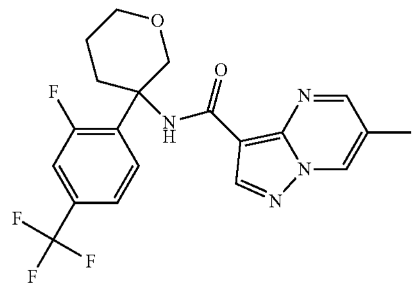 [SMILES: Cc1cnc2c(C(=O)NC3(c4ccc(C(F)(F)F)cc4F)CCCOC3)cnn2c1] |
| XXXII | 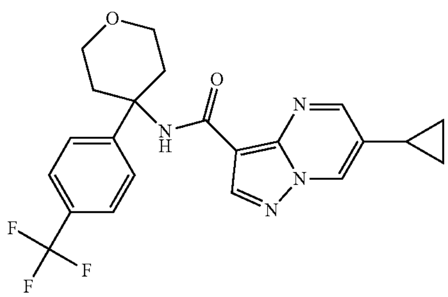 [SMILES: O=C(NC1(c2ccc(C(F)(F)F)cc2)CCOCC1)c1cnn2cc(C3CC3)cnc12] |
| XXXIII | 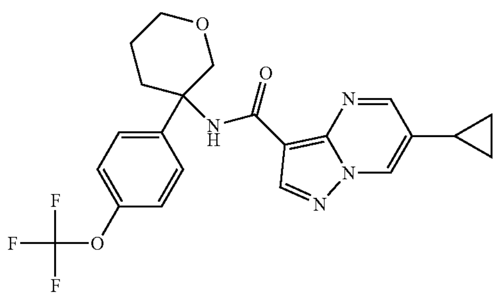 [SMILES: O=C(NC1(c2ccc(OC(F)(F)F)cc2)CCCOC1)c1cnn2cc(C3CC3)cnc12] |
| XXXIV | 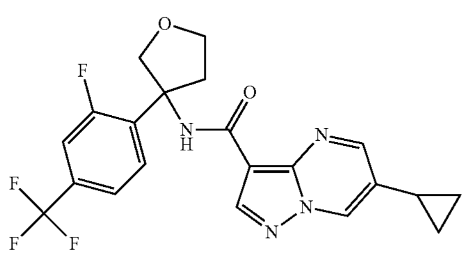 [SMILES: O=C(NC1(c2ccc(C(F)(F)F)cc2F)CCOC1)c1cnn2cc(C3CC3)cnc12] |
| XXXV | 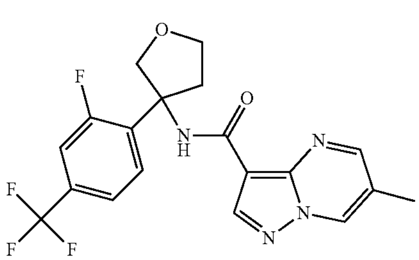 [SMILES: Cc1cnc2c(C(=O)NC3(c4ccc(C(F)(F)F)cc4F)CCOC3)cnn2c1] |

-continued

| No. | Structure |
|---|---|
| XXXVI | 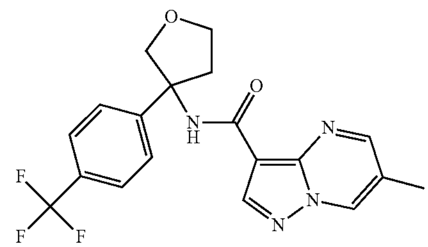 [SMILES: Cc1cnc2c(C(=O)NC3(c4ccc(C(F)(F)F)cc4)CCOC3)cnn2c1] |
| XXXVII | 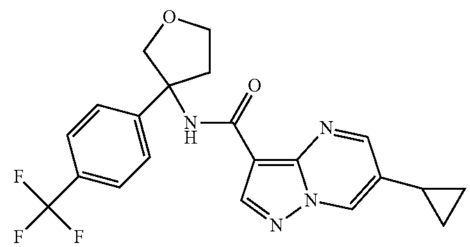 [SMILES: O=C(NC1(c2ccc(C(F)(F)F)cc2)CCOC1)c1cnn2cc(C3CC3)cnc12] |
| XXXVIII | 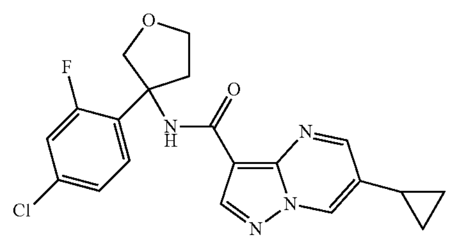 [SMILES: O=C(NC1(c2ccc(Cl)cc2F)CCOC1)c1cnn2cc(C3CC3)cnc12] |
| XXXIX | 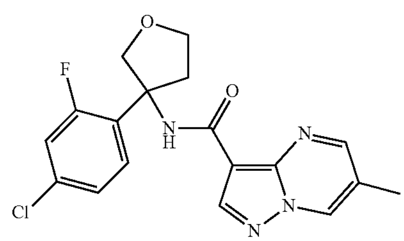 [SMILES: Cc1cnc2c(C(=O)NC3(c4ccc(Cl)cc4F)CCOC3)cnn2c1] |
| XL | 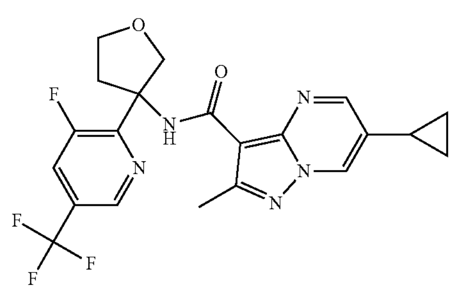 [SMILES: Cc1nn2cc(C3CC3)cnc2c1C(=O)NC1(c2ncc(C(F)(F)F)cc2F)CCOC1] |
| XLI | 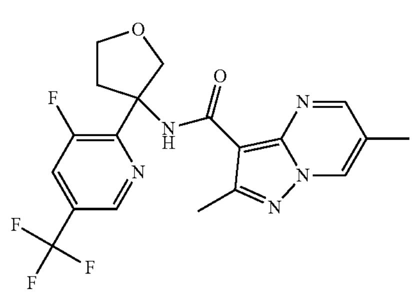 [SMILES: Cc1cnc2c(C(=O)NC3(c4ncc(C(F)(F)F)cc4F)CCOC3)c(C)nn2c1] |

| No. | Structure |
|---|---|
| XLII | 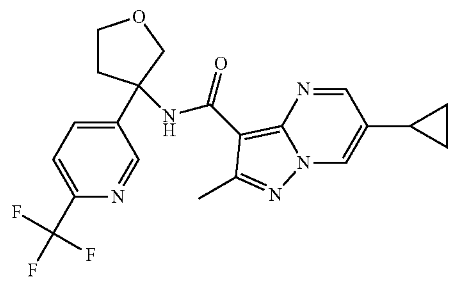 [SMILES: Cc1nn2cc(C3CC3)cnc2c1C(=O)NC1(c2ccc(C(F)(F)F)nc2)CCOC1] |
| XLIII | 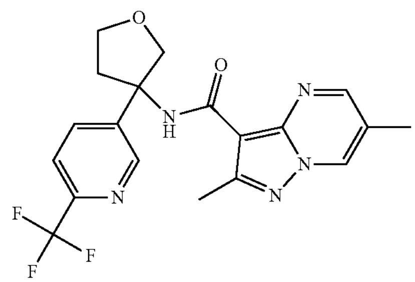 [SMILES: Cc1cnc2c(C(=O)NC3(c4ccc(C(F)(F)F)nc4)CCOC3)c(C)nn2c1] |
| XLIV | 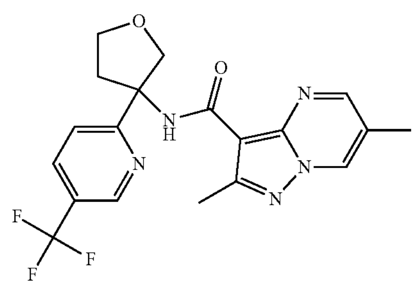 [SMILES: Cc1cnc2c(C(=O)NC3(c4ccc(C(F)(F)F)cn4)CCOC3)c(C)nn2c1] |
| XLV | 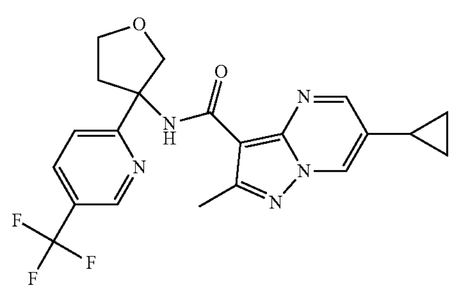 [SMILES: Cc1nn2cc(C3CC3)cnc2c1C(=O)NC1(c2ccc(C(F)(F)F)cn2)CCOC1] |
| XLVI | 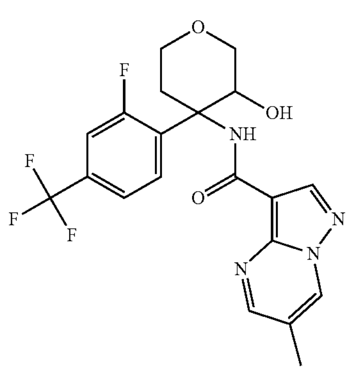 [SMILES: Cc1cnc2c(C(=O)NC3(c4ccc(C(F)(F)F)cc4F)CCOCC3O)cnn2c1] |
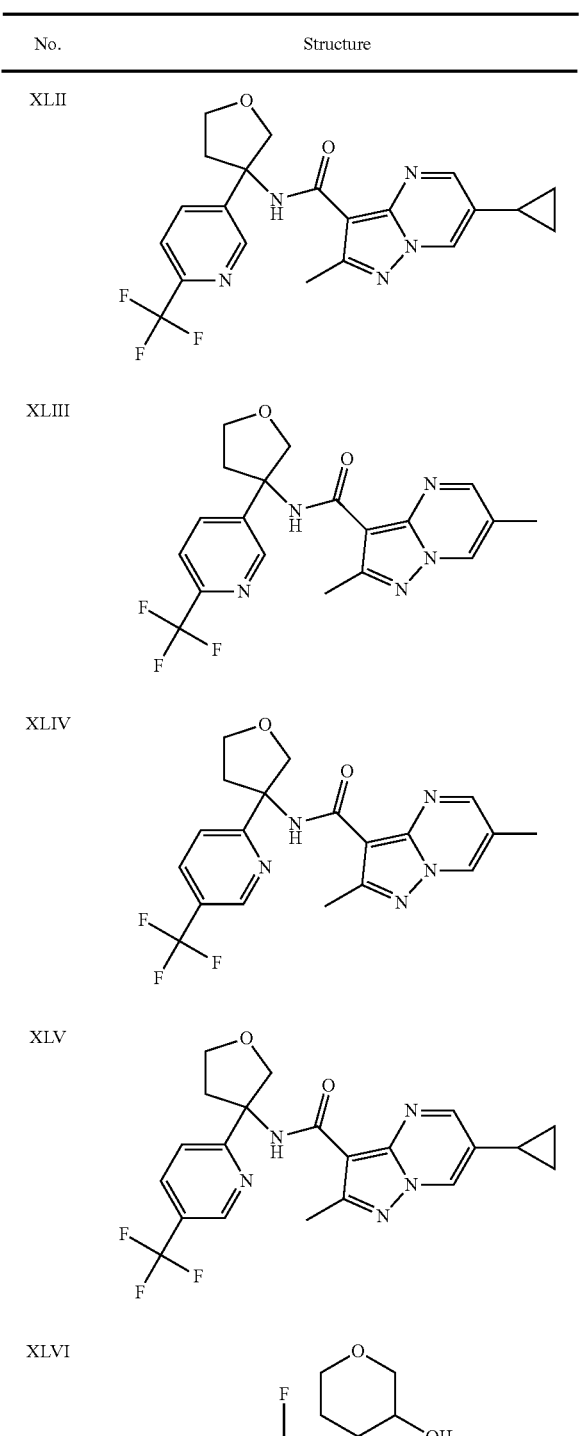
| No. | Structure |
|---|---|
| XLVII | 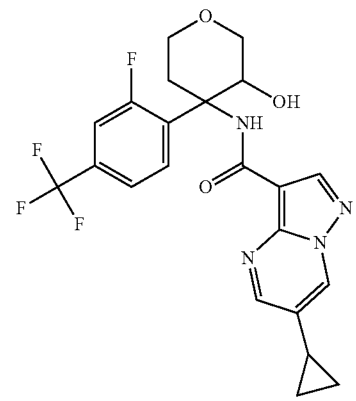 [SMILES: O=C(NC1(c2ccc(C(F)(F)F)cc2F)CCOCC1O)c1cnn2cc(C3CC3)cnc12] |
| XLVIII | 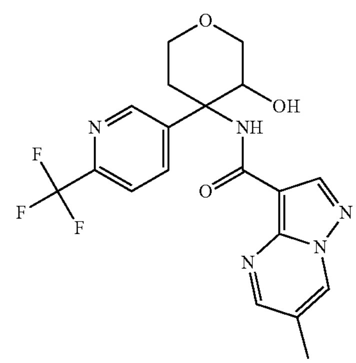 [SMILES: Cc1cnc2c(C(=O)NC3(c4ccc(C(F)(F)F)nc4)CCOCC3O)cnn2c1] |
| XLIX | 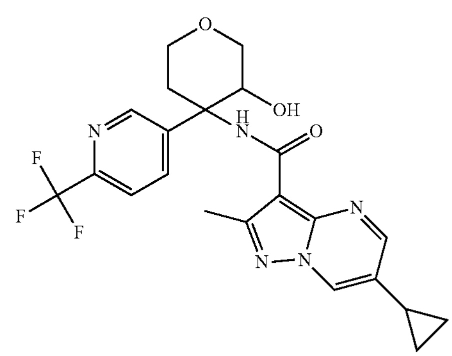 [SMILES: Cc1nn2cc(C3CC3)cnc2c1C(=O)NC1(c2ccc(C(F)(F)F)nc2)CCOCC1O] |
| L | 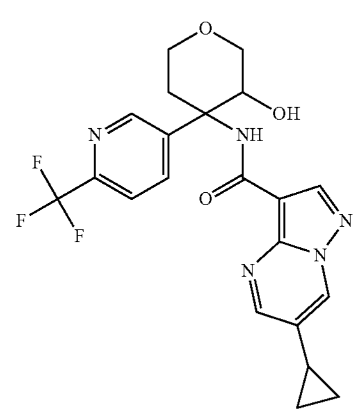 [SMILES: O=C(NC1(c2ccc(C(F)(F)F)nc2)CCOCC1O)c1cnn2cc(C3CC3)cnc12] |
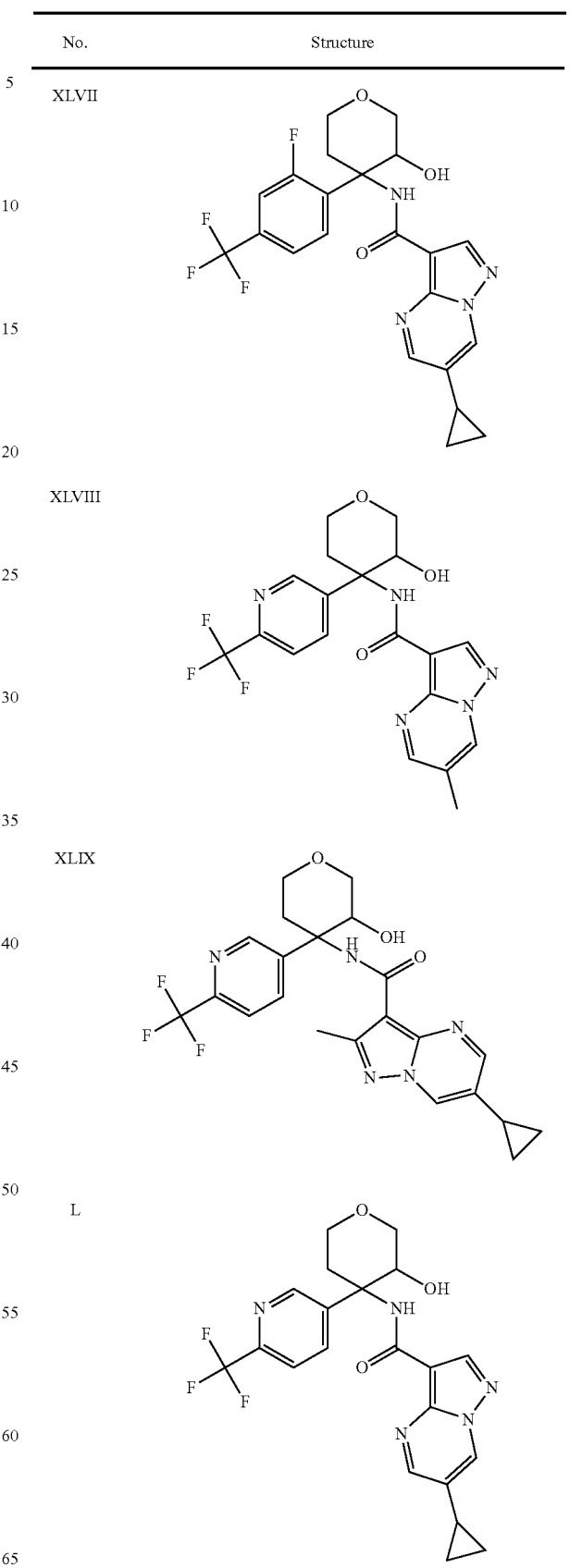

-continued

| No. | Structure |
|---|---|
| LI | 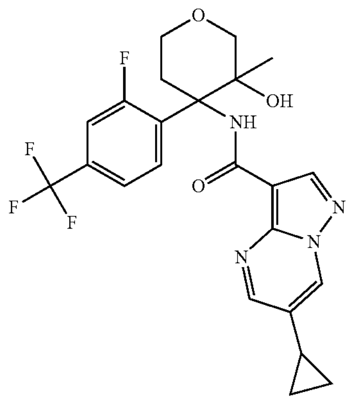 [SMILES: CC1(O)COCCC1(NC(=O)c1cnn2cc(C3CC3)cnc12)c1ccc(C(F)(F)F)cc1F] |
| LII | 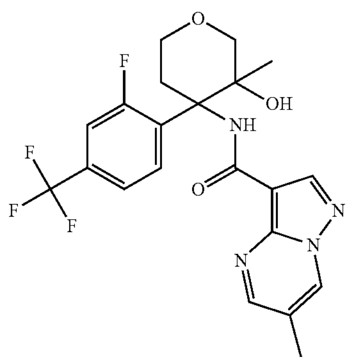 [SMILES: Cc1cnc2c(C(=O)NC3(c4ccc(C(F)(F)F)cc4F)CCOCC3(C)O)cnn2c1] |
| LIII | 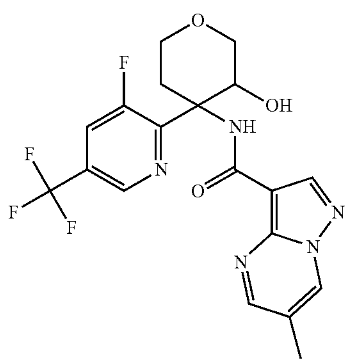 |
| LIV | 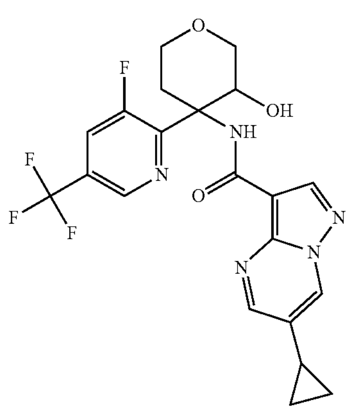 |

-continued

| No. | Structure |
|---|---|
| LV | 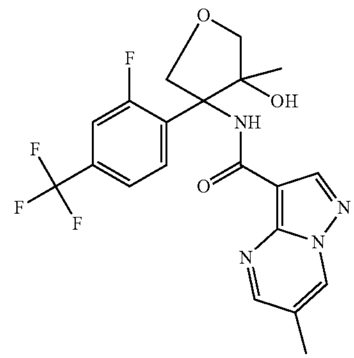 [SMILES: Cc1cnc2c(C(=O)NC3(c4ccc(C(F)(F)F)cc4F)COCC3(C)O)cnn2c1] |
| LVI | 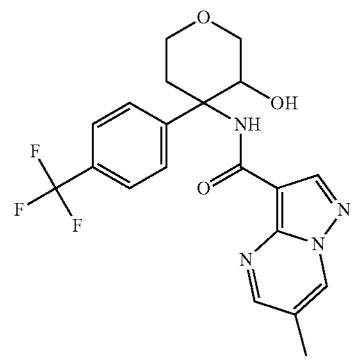 [SMILES: Cc1cnc2c(C(=O)NC3(c4ccc(C(F)(F)F)cc4)CCOCC3O)cnn2c1] |
| LVII | 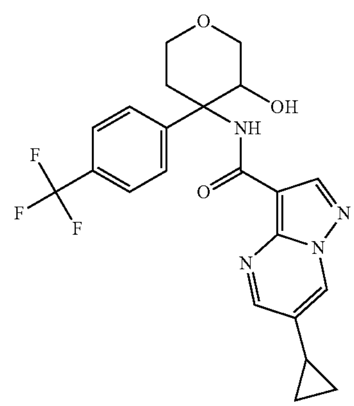 |
| LVIII | 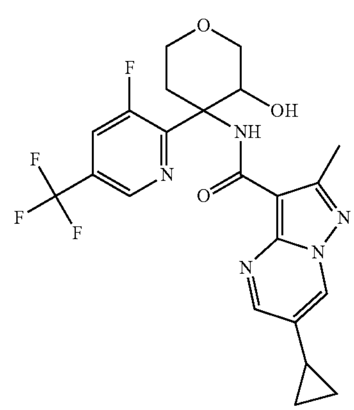 [SMILES: Cc1nn2cc(C3CC3)cnc2c1C(=O)NC1(c2ncc(C(F)(F)F)cc2F)CCOCC1O] |

| No. | Structure |
|---|---|
| LIX | 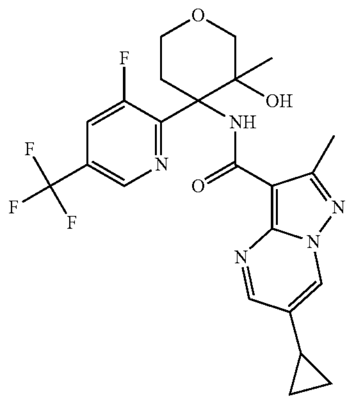 [SMILES: Cc1nn2cc(C3CC3)cnc2c1C(=O)NC1(c2ncc(C(F)(F)F)cc2F)CCOCC1(C)O] |
| LX | 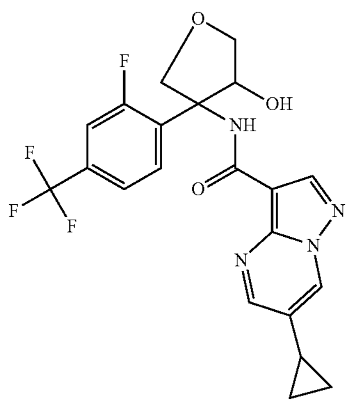 [SMILES: O=C(NC1(c2ccc(C(F)(F)F)cc2F)COCC1O)c1cnn2cc(C3CC3)cnc12] |
| LXI | 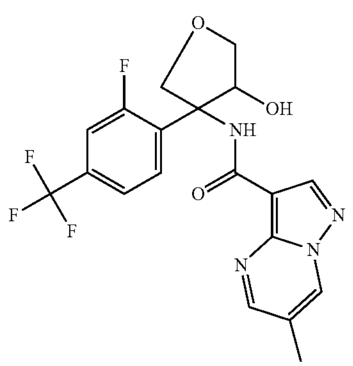 [SMILES: Cc1cnc2c(C(=O)NC3(c4ccc(C(F)(F)F)cc4F)COCC3O)cnn2c1] |
| LXII | 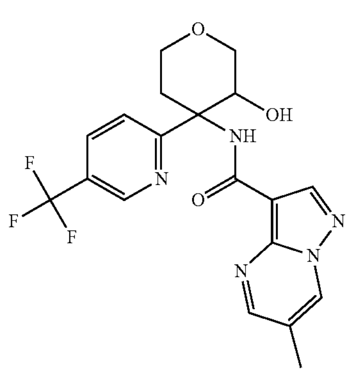 [SMILES: Cc1cnc2c(C(=O)NC3(c4ccc(C(F)(F)F)cn4)CCOCC3O)cnn2c1] |

| No. | Structure |
|---|---|
| LXIII | 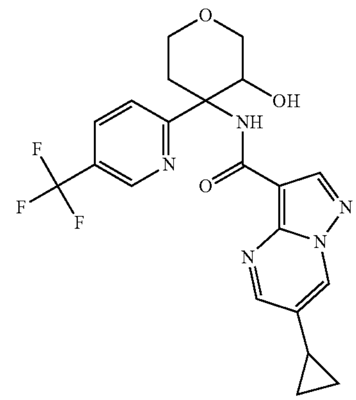 [SMILES: O=C(NC1(c2ccc(C(F)(F)F)cn2)CCOCC1O)c1cnn2cc(C3CC3)cnc12] |
| LXIV | 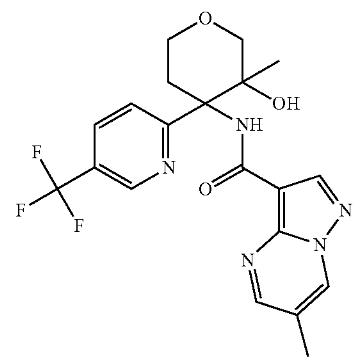 [SMILES: Cc1cnc2c(C(=O)NC3(c4ccc(C(F)(F)F)cn4)CCOCC3(C)O)cnn2c1] |
| LXV | 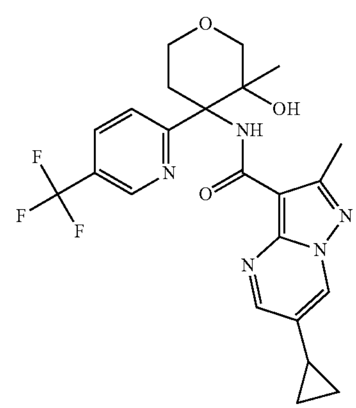 [SMILES: Cc1nn2cc(C3CC3)cnc2c1C(=O)NC1(c2ccc(C(F)(F)F)cn2)CCOCC1(C)O] |
| LXVI | 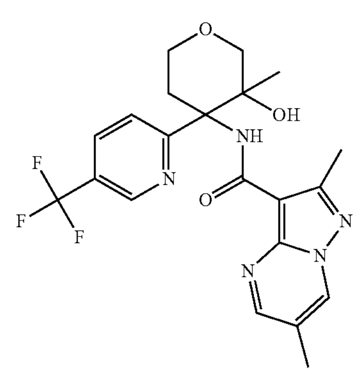 [SMILES: Cc1cnc2c(C(=O)NC3(c4ccc(C(F)(F)F)cn4)CCOCC3(C)O)c(C)nn2c1] |

| No. | Structure |
|---|---|
| LXVII | 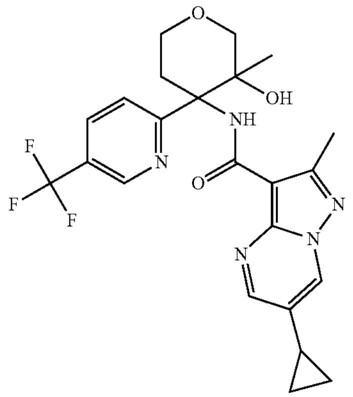 [SMILES: Cc1nn2cc(C3CC3)cnc2c1C(=O)NC1(c2ccc(C(F)(F)F)cn2)CCOCC1(C)O] |
| LXVIII | 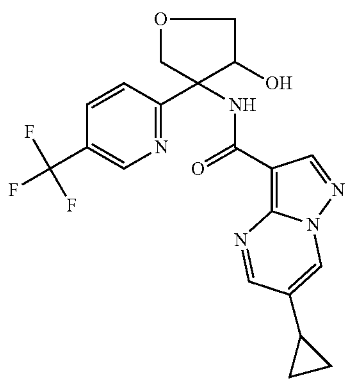 [SMILES: O=C(NC1(c2ccc(C(F)(F)F)cn2)COCC1O)c1cnn2cc(C3CC3)cnc12] |
| LXIX | 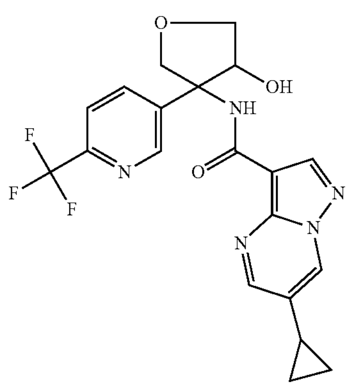 [SMILES: O=C(NC1(c2ccc(C(F)(F)F)nc2)COCC1O)c1cnn2cc(C3CC3)cnc12] |
| LXX | 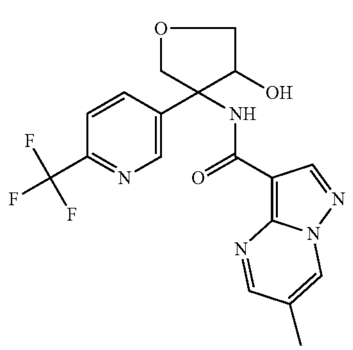 [SMILES: Cc1cnc2c(C(=O)NC3(c4ccc(C(F)(F)F)nc4)COCC3O)cnn2c1] |
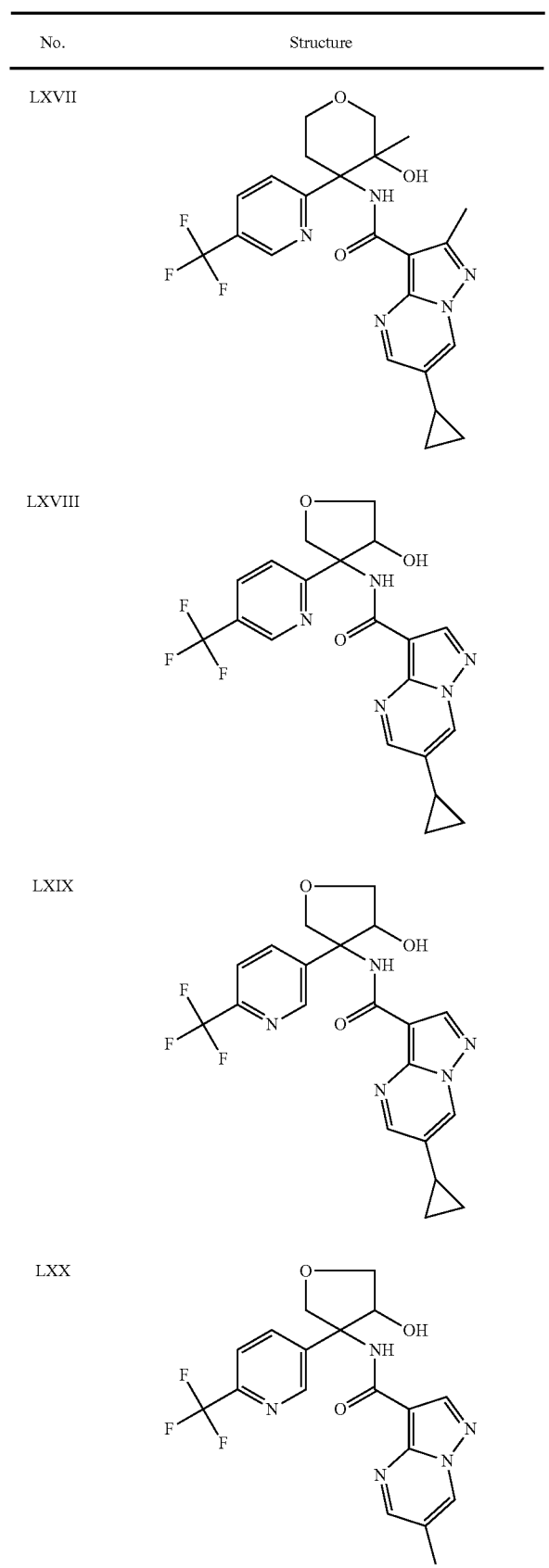
| No. | Structure |
|---|---|
| LXXI | 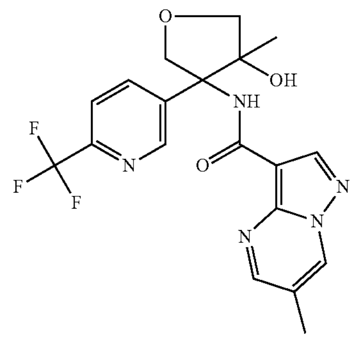 [SMILES: Cc1cnc2c(C(=O)NC3(c4ccc(C(F)(F)F)nc4)COCC3(C)O)cnn2c1] |
| LXXII | 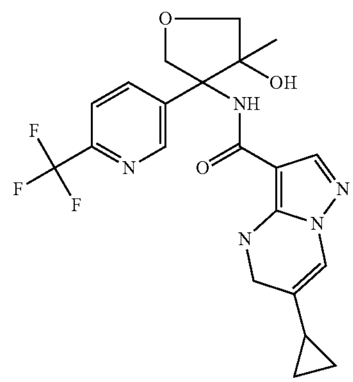 [SMILES: CC1(O)COCC1(NC(=O)c1cnn2c1NCC(C1CC1)=C2)c1ccc(C(F)(F)F)nc1] |
| LXXIII | 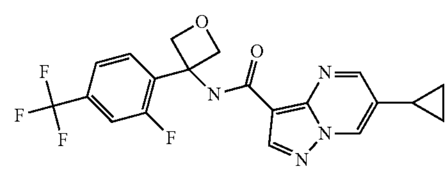 [SMILES: O=C(NC1(c2ccc(C(F)(F)F)cc2F)COC1)c1cnn2cc(C3CC3)cnc12] |
| LXXIV | 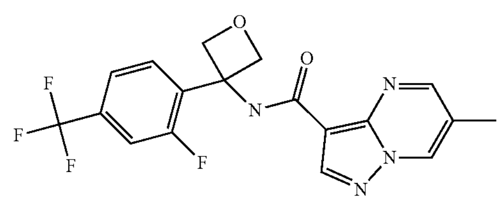 [SMILES: Cc1cnc2c(C(=O)NC3(c4ccc(C(F)(F)F)cc4F)COC3)cnn2c1] |
| LXXV | 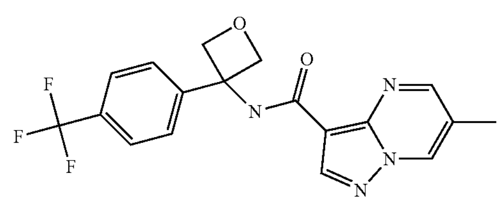 [SMILES: Cc1cnc2c(C(=O)NC3(c4ccc(C(F)(F)F)cc4)COC3)cnn2c1] |
| LXXVI | 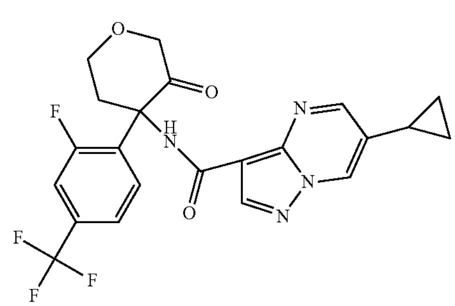 [SMILES: O=C(NC1(c2ccc(C(F)(F)F)cc2F)CCOCC1=O)c1cnn2cc(C3CC3)cnc12] |
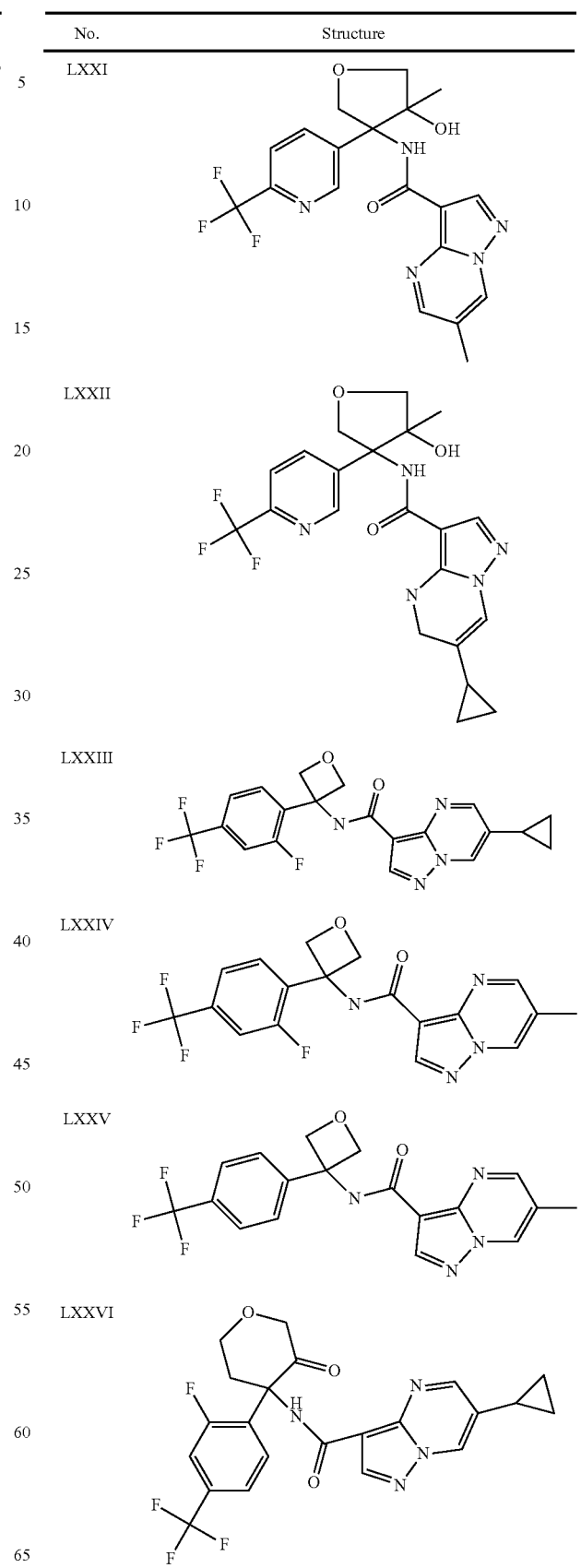

| No. | Structure |
|---|---|
| LXXVII | ![structure] | or the salts thereof.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core molecule or to the group to which the substituent is attached.

Within the present invention, the term "core molecule" is defined by the following structure:

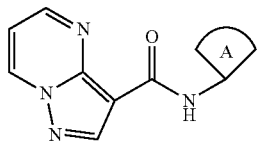

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond or attachment point which is connected to the core molecule, rest of the molecule or to the substituent to which it is bound as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" or "physiologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" or "physiologically acceptable salts" refer to derivatives of the disclosed compounds wherein the parent compound is modified by making acid or base salts thereof. Examples of pharmaceutically acceptable salts or physiologically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term "halogen" generally denotes fluorine (F), chlorine (CL), bromine (Br) and iodine (i).

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH (CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms.

In one embodiment the term "heteroaryl" means a mono- or bicyclic-ring system containing one to three heteroatoms selected from N, O or S(O)$_r$, wherein r=0, 1 or 2, consisting of 5 to 10 ring atoms wherein at least one of the heteroatoms is part of an aromatic ring.

Thus, the term "heteroaryl" includes the following exemplary structures which are not depicted as radicals as each form may be attached through a covalent bond to any atom so long as appropriate valences are maintained:

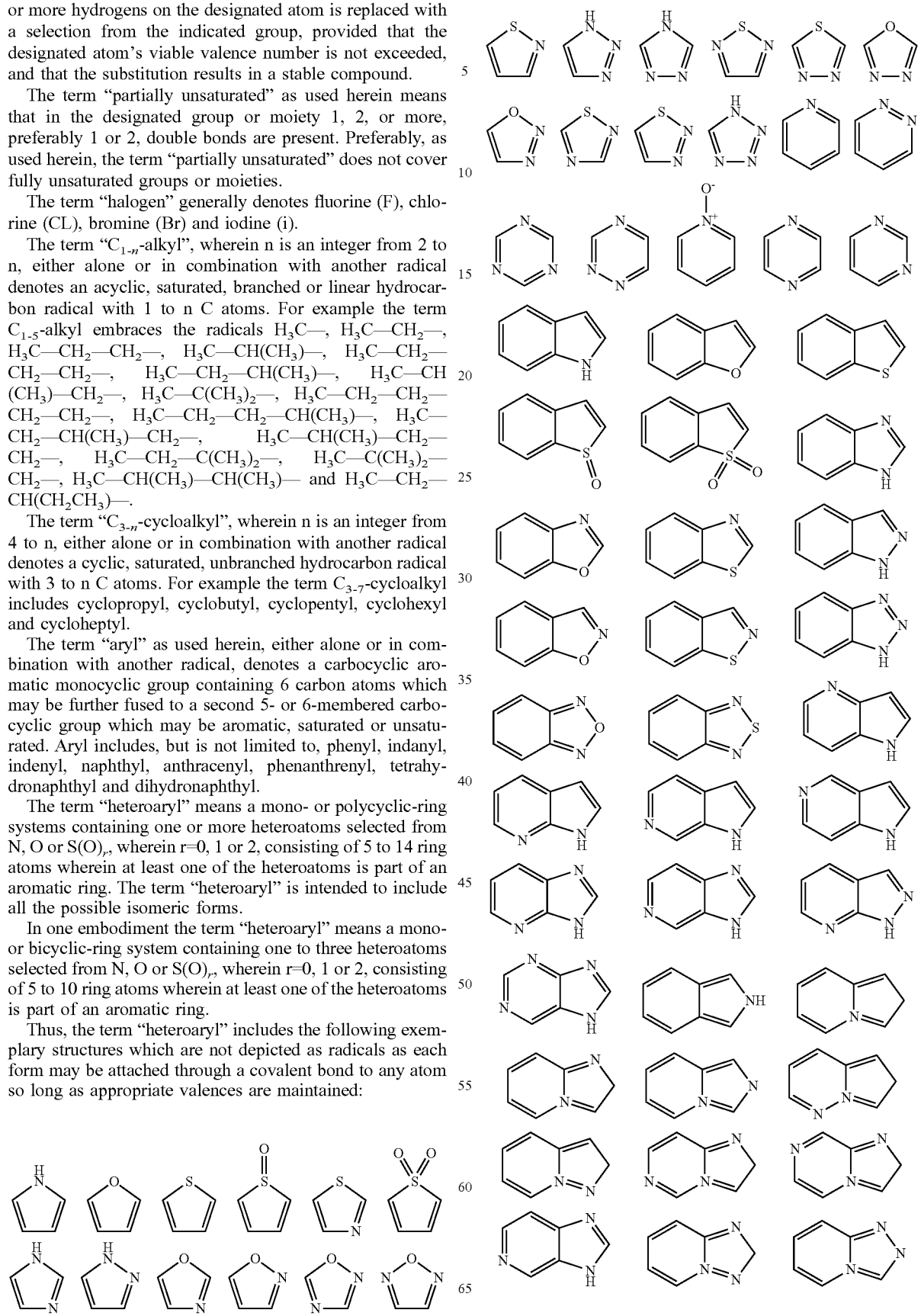

-continued

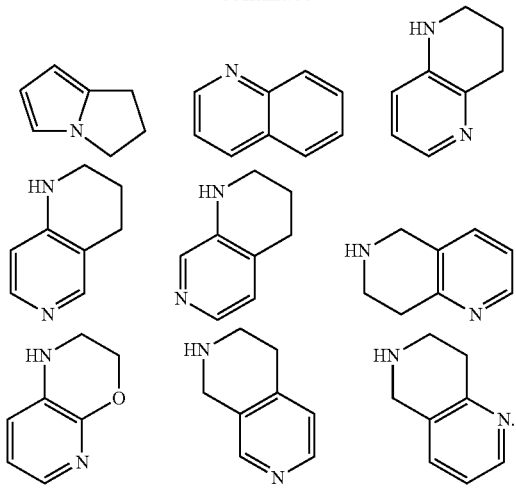

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

Preparation

The following Schemes shall illustrate generally how to manufacture the compounds of the present invention by way of example. The abbreviated substituents may be as defined above if not defined otherwise within the context of the schemes.

The preparation process might comprises:
a) Reacting a compound of formula (II)

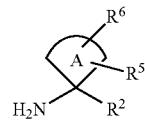

(II)

or a derivatives thereof, with a compound of formula (III)

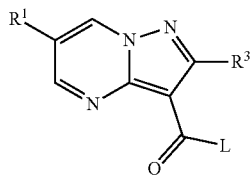

(III)

Wherein $R^1$, $R^2$, $R^3$, $R^5$, $R^6$ and A are as defined above and L is a suitable leaving group such as halogen atom (e.g. chlorine or bromine) or hydroxyl group.

In case of L=halogen, process a) typically comprises the reaction of a compound of formula (II) with a compound of formula (III) in an appropriate solvent such as acetonitrile or N,N-dimethylformamide in the presence of a base such as TEA or DIPEA at room temperature.

In case of L=OH, process a) typically comprises the reaction of a compound of formula (II) with a compound of formula (III) in an appropriate solvent such as N,N-dimethylformamide and in the presence of a suitable coupling agent (e.g. HATU or TBTU)

Compounds of formula (III) are either commercially available or can be prepared as described in the following Schemes, following known reported procedures.

Scheme 1

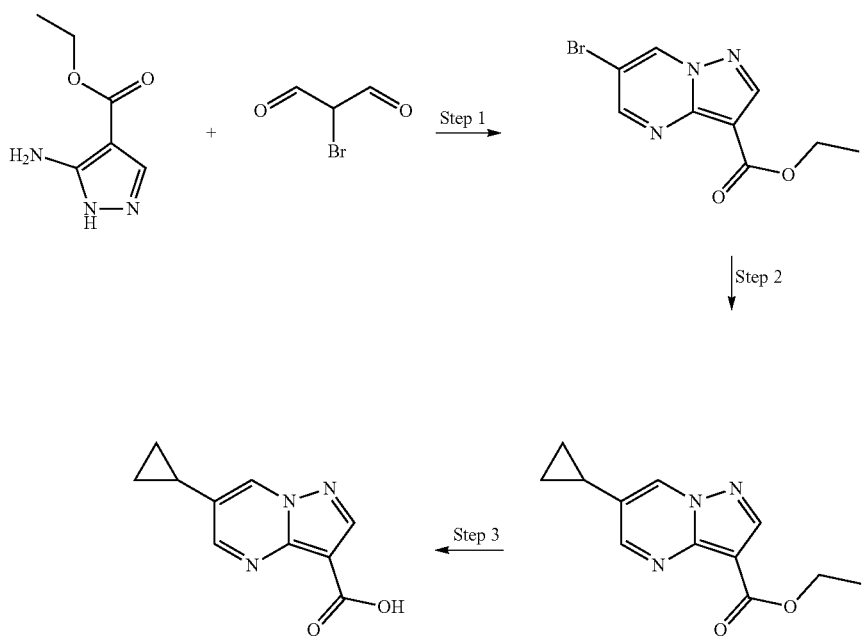

In Scheme 1, Step 1 typically involves reaction of commercially available amino pyrazole derivatives with 2-Bromo-malonaldehyde in the presence of acetic acid in a suitable solvent such as EtOH under heating. In Step 2, the cyclopropyl group is introduced by a cross coupling palladium catalyzed reaction using for example potassium cyclopropyltrifluoroborate, a suitable palladium catalyst such as Palladium(II) acetate and 2-dicyclohexylphosphino-2',6'-diisopropoxy 1,1'-biphenyl as ligand in an appropriate solvent such as toluene under heating. In Step 3 the ethyl ester is then hydrolyzed under basic conditions using sodium hydroxide or lithium hydroxide monohydrate in an appropriate solvent such as EtOH or a mixture of THF/water.

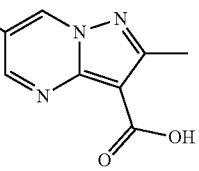

In Scheme 3, Step 1 typically involves reaction of commercially available amino pyrazole derivative with 1,1,3,3,-tetraethoxy-2-methyl-propane in the presence of hydrochloric acid in a suitable solvent such as EtOH under heating. Basic hydrolysis provides the desired carboxylic acid derivative Compounds of formula (II) are either commercially available or can be prepared as described in the following Schemes.

Scheme 2

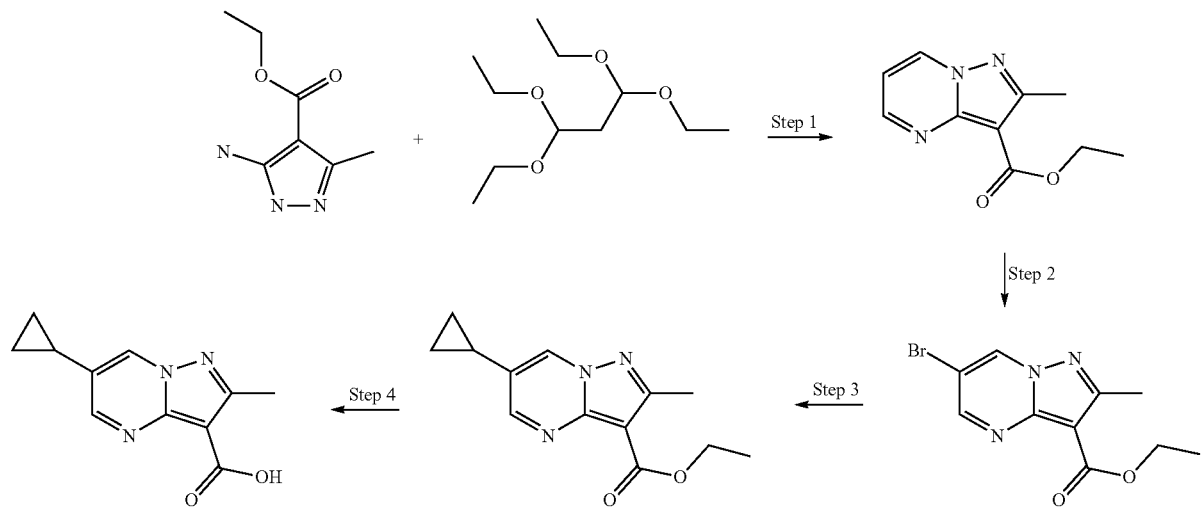

In Scheme 2, Step 1 typically involves reaction of commercially available amino pyrazole derivative with 1,1,3,3,-tetraethoxy-propane in the presence of hydrochloric acid in a suitable solvent such as EtOH under heating. Bromination using bromine in acetic acid as solvent at room temperature provides the bromo derivative and the cyclopropyl group is then introduced as described in Scheme 1.

Scheme 3

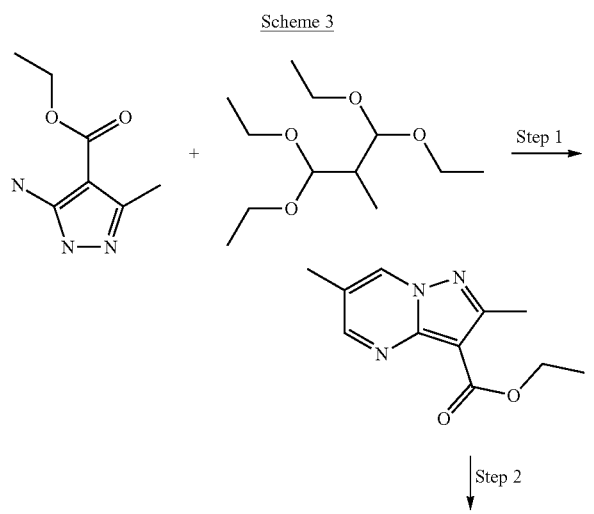

Scheme 4

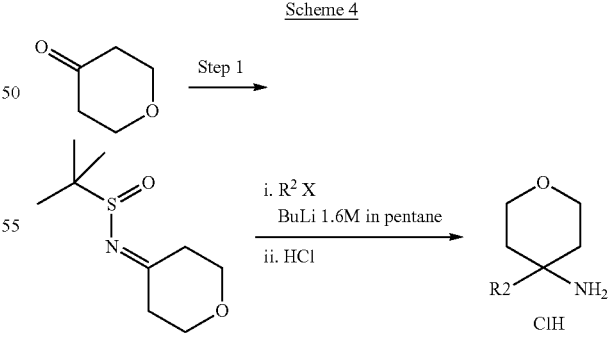

In Scheme 4, R² is aryl or heteroaryl

In Scheme 4, Step 1, commercially available ketone is converted in the corresponding 2-methyl-propane-2-sulfinyl-imine using titanium (IV) ethoxide and 2-Methyl-propane-2-sulfinic acid amide, as described in WO 2005087751.

The obtained intermediate is then added dropwise to a previously prepared solution of organo lithium derivatives of the appropriate halogen compounds (R²X, where X is bromine or iodine) prepared using for example commercially available solution of tert-butyllithium or n-buthyllithium in hexane or pentane at low temperature (−75° C.) in a suitable solvent such as toluene or THE. Cleavage of the resulting sulphinic amide by treatment with acid such as a 4N solution of HCl in a suitable solvent such as dioxane provides the desired intermediates amines.

The above described synthesis applies also for the analogues with 5 and 4 membered ring, starting from commercially available cyclopentanone and oxetane-3-one.

chloro palladium(II) as catalyst, potassium carbonate as base in an appropriate solvent such as a mixture of toluene/water under heating. The epoxidation step is performed using MCPBA as oxidating agent in DCM at room temperature. The desired amino alcohol intermediate is then obtained by opening the epoxide with a modified Ritter procedure using trifluoromethane sulfonic acid and acetonitrile followed by basic hydrolysis of the formed intermediate, in analogy to the procedure described in Tetrahedron Asymmetry, 1996, 5, 1501-1506.

The relative stereochemistry of the above described aminoalcohols is reported in the Experimental description.

Scheme 5

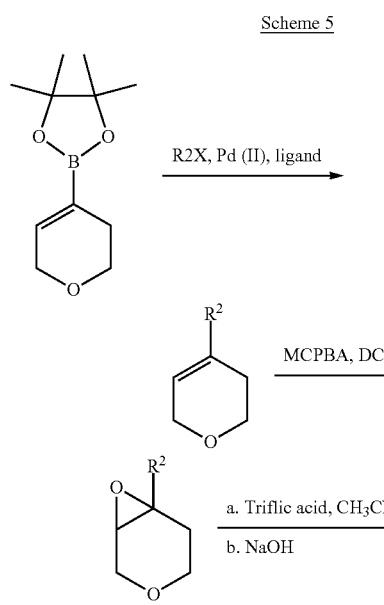

Scheme 6

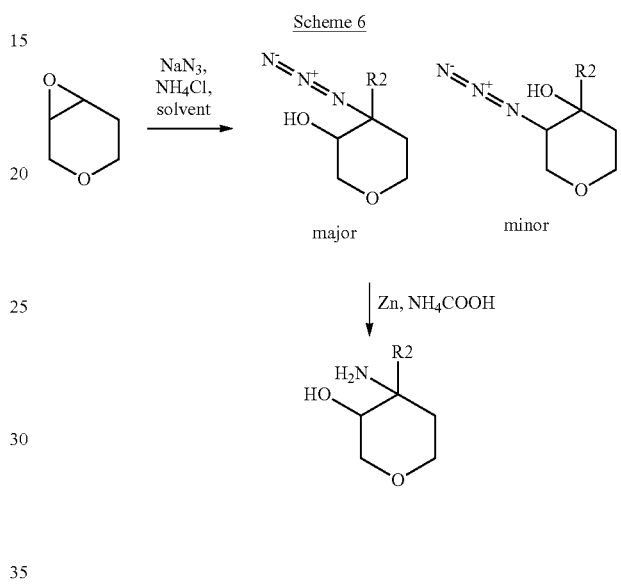

In Scheme 5, R² is aryl derivatives.

Step 1 involves a cross coupling Suzuky reaction with commercially available boronic acid or pinacol ester derivatives and the appropriate halogen derivatives (X=Br or I) using for example 1,1'-bis(diphenylphosphino)ferrocenedi- In Scheme 6, R² is aryl or heteroaryl.

In Scheme 6, the opening of the epoxide is performed using sodium azide in the presence of ammonium chloride under heating in a suitable solvent, such as dimethyl formamide. After separation of the two regioisomers, (see experimental), the azide group is then converted into amino group by reduction following well known reported procedure such as for example using zinc and ammonium formate in a suitable solvent such as methanol at room temperature.

The relative stereochemistry of the above described amino alcohols is reported in the Experimental description.

Scheme 7

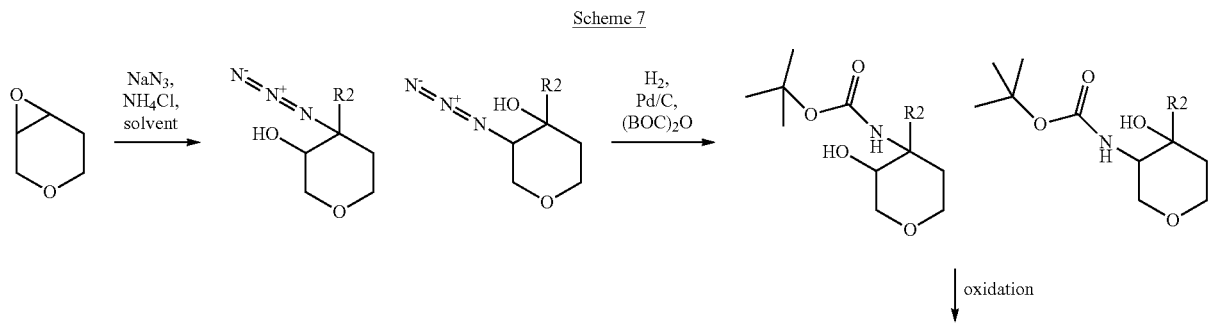

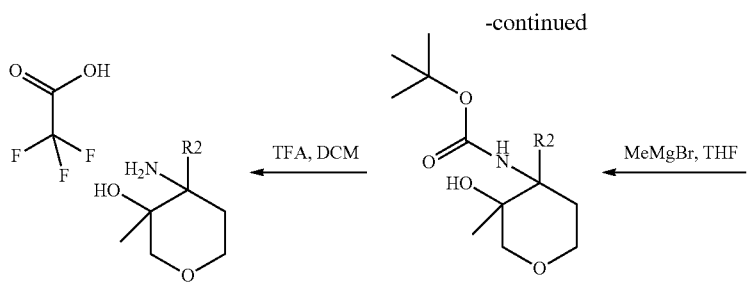

In Scheme 7, R² is aryl or heteroaryl

In Scheme 7, the regioisomeric mixture of azide intermediates, obtained following the approach described in Scheme 6, is reduced under catalytic hydrogenation conditions, using for example Pd/C in a suitable solvent such as ethanol and in the presence of di.tert-butyldicarbonate to obtain the protected amino alcohols derivatives. Oxidation to ketone is performed using Dess Martin periodinane in a suitable solvent such as DCM at room temperature or using Swern's procedure Formation of the tertiary alcohols is accomplished by addition of methyl magnesium chloride to the carbonyl group at low temperature (−20° C.) in a suitable solvent such as THF. The cleavage of the Boc protecting group is performed under acid conditions using for example trifluoroacetic acid in a suitable solvent such as DCM at room temperature.

The regioisomeric ratio of epoxide opening and the relative stereochemistry of the above described amino alcohols are reported in the Experimental description.

Scheme 8

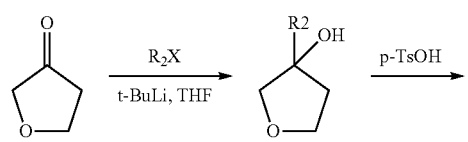

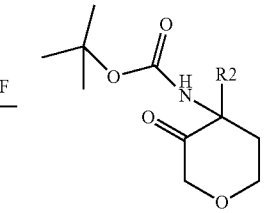

In Scheme 8 R² is aryl.

In Scheme 8, the desired tetrahydrofuran-3-ol-intermediates are obtained by addition of the appropriate lithium derivatives, prepared reacting a suitable halogen compounds (R²X, X=halogen) with commercially available solution of tert-butyllithium or n-buthyllithium in hexane or pentane at low temperature (−75° C.) in a suitable solvent such as toluene or THF, to the carbonyl group. Treatment with pTsOH in toluene under reflux provides the double bond derivatives which are transformed into the desired aminoalcohols following the approaches described in Scheme 5.

The relative stereochemistry of the aminoalcohols compounds are reported in the Experimental description.

Scheme 9

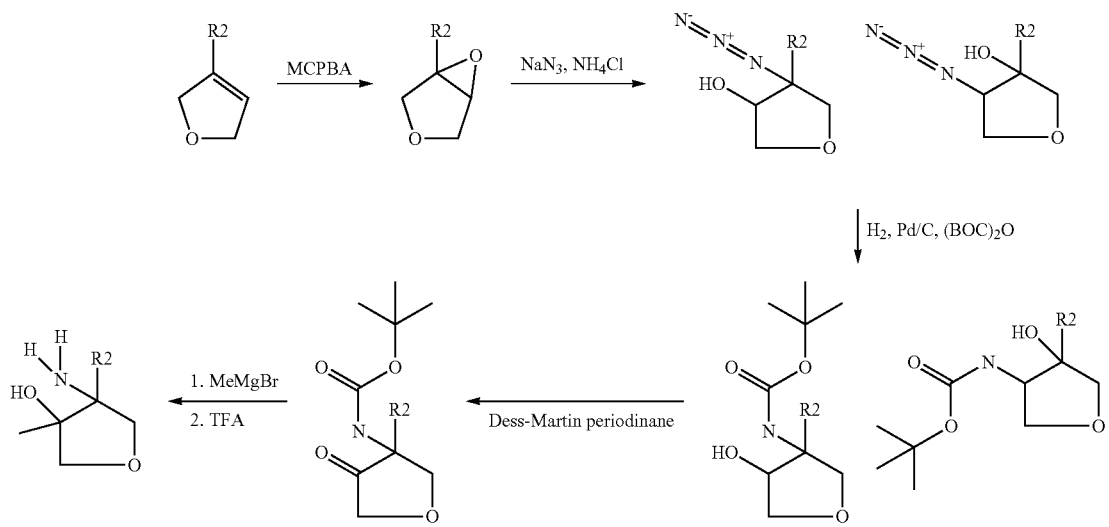

In Scheme 9, $R^2$ is aryl or heteroaryl.

The desired amino alcohols are obtained following the approaches described above in Scheme 6 and 7.

The regiochemistry ratio of the epoxide opening and the relative stereochemistry of the aminoalcohols compounds are reported in the Experimental description.

Biological Examples

In-Vitro Effect:

The in-vitro effect of the active compounds of the invention can be shown with the following biological assays.

a) Phosphodiesterase (PDE) 2A and 10 Assay with Fluorescent Substrate

Assay Principle:

The PDE reaction cleaves cAMP to AMP. The IMAP system (Molecular Device) using fluorescence polarization (FP) as detection principle was used to measure enzyme activity. A fluorescent labeled cAMP was used as substrate for the reaction, generating a labeled AMP. The fluorescent AMP binds specifically to the large M(III)-based nanoparticles which reduces the rotational speed of the substrate and thus increases its polarization.

Detailed Method:

The inhibition of PDE 2A or 10 enzyme activity was assessed using IMAP-Phosphodiesterase-cAMP fluorescence labeled substrate (Molecular Devices, Order No. R7506), IMAP TR-FRET screening express (Molecular Devices, Order No. R8160, the TR-FRET component will not be used) and PDE 2A or PDE10 protein expressed upon baculovirus infection in SF9 cells. The cells were incubated after infection for ~3 days and protein production was confirmed by Western Blot. The cells were collected by centrifugation and the pellet frozen in liquid nitrogen before it was resuspended in PBS containing 1% Triton X-100 and protease inhibitors. After 45 min incubation on ice, the cell debris was removed by centrifugation (13.000 rpm, 30 min). Since SF 9 cells do not express cAMP hydrolyzing enzymes to a high extent, no further purification of the protein was needed.

All reactions were performed in 384 well plates, Perkin Elmer black optiplates and IMAP reaction buffer with 0.1% Tween20 (kit component)

Compounds were serial diluted in DMSO. With an intermediate dilution step with reaction buffer DMSO concentration was reduced to achieve 1% DMSO in the assay reaction. Setup of the assay started with 10 µl enzyme (~10 ng/well, depending on prep. batch), 5 µl compound, reaction was started by addition of 5 µl labeled cAMP (30 nM, final concentration), immediately mixed for 15 seconds on a Eppendorf mixmate (2000 rpm) followed by an incubation at room temperature for 90 minutes in the dark. Reaction is stopped by adding of 60 µl binding buffer for FP/cAMP (kit component). After at least 90 min of further incubation (room temperature, dark) the assay was measured at 485 nm excitation/525 nm emission in an Envision multilabel reader (PerkinElmer).

Each assay plate contained wells with vehicle controls (1% DMSO) for the measurement of non-inhibited reaction (=100% control) and wells without enzyme as 0% controls.

The analysis of the data was performed by calculation of the percentage of inhibition in the presence of test compound compared to the vehicle control samples (100% control, no inhibition) and a low control (0% control, no enzyme).

IC50 values are calculated with Assay Explorer or other suited software based on curve fitting of results of at least 8 different compound concentrations. The compound concentrations may vary according to the needed range, but typically cover the range between 10 µM and 0.1 µM.

TABLE 3a

PDE2A Activity of the examples (Ex) compiled in the experimental part, based on above described assay (IMAP fluorescent).

| Ex. | PDE2 $IC_{50}$ [nM] |
|---|---|
| 1 | 14 |
| 2 | 22 |
| 3 | 266 |
| 4 | 48 |
| 5 | 258 |
| 6 | 199 |
| 7 | 77 |
| 8 | 69 |
| 9 | 117 |
| 10 | 80 |
| 11 | 297 |
| 12 | 1650 |
| 13 | 359 |
| 14 | 456 |
| 15 | 746 |
| 16 | 537 |
| 17 | 39 |
| 18 | 129 |
| 19 | 519 |
| 20 | 172 |
| 21 | 74 |
| 22 | 119 |
| 23 | 232 |
| 24 | 754 |
| 25 | 88 |
| 26 | 174 |
| 27 | 534 |
| 28 | 834 |
| 29 | 661 |
| 30 | 12 |
| 31 | 30 |
| 32 | 67 |
| 33 | 83 |
| 34 | 27 |
| 35 | 31 |
| 36 | 180 |
| 37 | 192 |
| 38 | 331 |
| 39 | 568 |
| 40 | 84 |
| 41 | 291 |
| 42 | 130 |
| 43 | 359 |
| 44 | 840 |
| 45 | 239 |
| 46 | 5.7 |
| 47 | 240 |
| 48 | 1.35 |
| 49 | 70 |
| 50 | 596 |
| 51 | 59 |
| 52 | 231 |
| 53 | 100 |
| 54 | 12 |
| 55 | 21 |
| 56 | 229 |
| 57 | 103 |
| 58 | 14 |
| 59 | 60 |
| 60 | 22 |
| 61 | 19 |
| 62 | 127 |
| 63 | 124 |
| 64 | 496 |
| 65 | 30 |
| 66 | 25 |
| 67 | 50 |
| 68 | 24 |
| 69 | 1740 |

TABLE 3a-continued

PDE2A Activity of the examples (Ex) compiled in the experimental part, based on above described assay (IMAP fluorescent).

| Ex. | PDE2 IC$_{50}$ [nM] |
|---|---|
| 70 | 1250 |
| 71 | 13 |
| 72 | 122 |
| 73 | 1142 |
| 74 | 2530 |
| 75 | 42 |
| 80b | 75 |
| 80a | 313 |
| 81a | 3.4 |
| 81b | 149 |
| 82a | 1.2 |
| 82b | 40 |
| 83a | 5.9 |
| 83b | 1820 |
| 84a | 120 |
| 84b | 2790 |
| 85a | 130 |
| 86a | 3.9 |
| 86b | 2550 |
| 87a | 1000 |
| 87b | 184 |
| 88a | 32 |
| 88b | 3030 |
| 89a | 1000 |
| 90a | 200 |
| 90b | 14 |
| 91a | 63 |
| 91b | 1590 |
| 92a | 93 |
| 92b | 712 |
| 93a | 11 |
| 93b | 1520 |

TABLE 3b

PDE10 Activity of the examples (Ex) compiled in the experimental part, based on above described assay (IMAP fluorescent).

| Ex. | PDE10 IC$_{50}$ [nM] |
|---|---|
| 1 | 10100 |
| 2 | >10000 |
| 3 | >10000 |
| 4 | 550 |
| 5 | 12200 |
| 6 | >10000 |
| 7 | 9110 |
| 8 | >10000 |
| 9 | >10000 |
| 10 | 9820 |
| 11 | 1470 |
| 12 | >10000 |
| 13 | 9910 |
| 14 | 8430 |
| 15 | >10000 |
| 16 | >10000 |
| 17 | 6940 |
| 18 | 8630 |
| 19 | >10000 |
| 20 | >10000 |
| 21 | >10000 |
| 22 | 9920 |
| 23 | >10000 |
| 24 | >10000 |
| 25 | 9070 |
| 26 | >10000 |
| 27 | >10000 |
| 28 | >10000 |
| 29 | 5930 |
| 30 | >10000 |
| 31 | >10000 |
| 32 | >10000 |
| 33 | >10000 |
| 34 | 10800 |
| 35 | >10000 |
| 36 | >10000 |
| 37 | >10000 |
| 38 | 6710 |
| 39 | >10000 |
| 40 | 5730 |
| 41 | 7950 |
| 42 | 5590 |
| 43 | 6860 |
| 44 | 9680 |
| 45 | 7850 |
| 46 | >10000 |
| 47 | >10000 |
| 48 | 6620 |
| 49 | >10000 |
| 50 | >10000 |
| 51 | 9040 |
| 52 | >10000 |
| 53 | >10000 |
| 54 | 9670 |
| 55 | >10000 |
| 56 | >10000 |
| 57 | >10000 |
| 58 | >10000 |
| 59 | >10000 |
| 60 | >10000 |
| 61 | 6650 |
| 62 | 7160 |
| 63 | >10000 |
| 64 | >10000 |
| 65 | 9760 |
| 66 | >10000 |
| 67 | >10000 |
| 68 | >10000 |
| 69 | >10000 |
| 70 | >10000 |
| 71 | >10000 |
| 72 | >10000 |
| 73 | >10000 |
| 74 | >10000 |
| 75 | >10000 |
| 80b | 5280 |
| 80a | 7760 |
| 81a | >10000 |
| 81b | >10000 |
| 82a | >10000 |
| 82b | 8461 |
| 83a | >10000 |
| 83b | >10000 |
| 84a | >10000 |
| 84b | >10000 |
| 85a | >10000 |
| 86a | >10000 |
| 86b | 9940 |
| 87a | >10000 |
| 87b | >10000 |
| 88a | 7560 |
| 88b | >10000 |
| 89a | >10000 |
| 90a | 8590 |
| 90b | 7350 |
| 91a | 7700 |
| 91b | 5670 |
| 92a | >10000 |
| 92b | >10000 |
| 93a | >10000 |
| 93b | >10000 |

In-Vivo Effect:
Animal Experiments and Sample Analysis (CSF):

Test compounds were administered to animals (rat) different routes at doses of 10.0 or 5 µmol/kg, (both oral and intravenous). CSF samples were carefully collected by puncture of the cisterna magna under anesthaesia. Immediately after CSF sampling, blood was taken by heart puncture and brains were dissected out. Blood was collected in EDTA-coated microvettes and plasma was prepared by centrifugation. Concentration of the test compounds in plasma, CSF or brain homogenate was determined using HPLC-MS-MS.

TABLE 4

Plasma, brain and CSF concentration

| Ex. | Time(*) (h) | conc plasma (nmol/L) | conc brain (nmol/L) | c(brain)/ c(plasma) | conc CSF (nmol/L) | c(CSF)/ c(plasma) |
|---|---|---|---|---|---|---|
| 1 | 0.5 | 243 | 471 | 1.96 | 11 | 0.04 |
| 21 | 0.5 | 1210 | 1320 | 1.17 | 106 | 0.09 |
| 25 | 0.5 | 1040 | 957 | 0.92 | 111 | 0.12 |
| 81a | 0.5 | 2460 | 1070 | 0.42 | 261 | 0.10 |
| 82a | 0.5 | 3320 | 1180 | 0.36 | 157 | 0.05 |
| 83a | 0.5 | 794 | 449 | 0.6 | 61 | 0.08 |

(*)Time between administration and CSF sampling

For the skilled in the art it is evident from the experimental results shown above that compounds of the present invention are not only potent phosphodiesterase 2 inhibitors but also reach high CSF concentrations and adequate CSF to plasma ratios.

Plasma Protein Binding (Determination of Human and Rat Plasma Protein Binding with Equilibrium Dialysis)

This equilibrium dialysis (ED) technique is used to determine the approximate in vitro fractional binding of test compounds to human and rat plasma proteins.

Dianorm Teflon dialysis cells (micro 0.2) are used. Each cell consists of a donor and an acceptor chamber, separated by an ultrathin semipermeable membrane with a 5 kDa molecular weight cutoff.

Stock solutions for each test compound are prepared in DMSO at 1 mM and diluted to a final concentration of 1.0 µM. The subsequent dialysis solutions are prepared in pooled human and rat plasma (with NaEDTA)

Aliquots of 200 µL dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 ml Acetonitril/water (80/20). Aliquots of 25 µL of the plasma dialysate are transferred into deep well plates and mixed with 25 µl Acetonitril/water (80/20), 25 µl buffer, 25 µL calibration solution and 25 µl Internal Standard solution. Protein precipitation is done by adding 200 µl Acetonitrile.

Aliquots of 50 µl of the buffer dialysate are transferred into deep well plates and mixed with 25 µl blank plasma, 25 µl Internal Standard solution and 200 µl Acetonitril.

Samples are measured on HPLC-MS/MS-Systems and evaluated with Analyst-Software.

Percent bound is calculated with the formula: % bound= (plasma concentration−buffer concentration/plasma concentration)×100 and % free is calculated as difference.

TABLE 4

PPB (Plasma Protein Binding) of compounds of the present invention in human and rat plasma.

| EX | PPB HUM % BINDING | PPB RAT % BINDING |
|---|---|---|
| 2 | 91.5 | 94.7 |
| 1 | 96 | 96.8 |
| 31 | 95.3 | 97.6 |
| 35 | 92.4 | 93.7 |
| 37 | 94.4 | 93.50 |
| 17 | 91.4 | 90.7 |
| 25 | 75.4 | 83.1 |
| 21 | 83.8 | 87.2 |
| 3 | 84.3 | — |
| 68 | 84.4 | — |
| 69 | 90.7 | — |
| 70 | 79.4 | — |
| 71 | 81.1 | — |
| 51 | 46.9 | — |
| 53 | 81.7 | — |
| 88b | 44.2 | — |
| 82a | 78.7 | 86.5 |
| 81a | 63.0 | 74.3 |
| 46 | 67.1 | 68.7 |
| 81b | 65.3 | 66.2 |
| 83a | 84.4 | 82.2 |
| 86a | 89.5 | 93.5 |

For the skilled in the art it is evident from the experimental results shown above that compounds of the present invention are not only potent phosphodiesterase 2 inhibitors but also have low plasma protein binding.

Assessment of Efflux in Madin-Darby Canine Kidney Cells Transfected with the Human MDR1 Gene (MDCK Assay)

Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 µm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$), 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, 0.25% BSA, pH 7.4) to prepare the transport solutions (0.1-300 µM compound, final DMSO <=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution. Efflux ratio is calculated dividing the Papp (b-a) values by the Papp (a-b) values.

TABLE 5

Papp (PEBA) and efflux of compounds of the present invention

| Ex. | Papp (a-b) mean [10-6 cm/s] | efflux ratio |
| --- | --- | --- |
| 1 | 78 | 0.6 |
| 2 | 84 | 0.6 |
| 37 | 86 | 0.5 |
| 17 | 85 | 0.6 |
| 25 | 100 | 0.8 |
| 21 | 94 | 0.6 |
| 3 | 97 | 0.7 |
| 69 | 25 | 1.3 |
| 70 | 20 | 2.1 |
| 71 | 23 | 1.9 |
| 53 | 15 | 1.8 |
| 82a | 59 | 1.0 |
| 51 | 11 | 5.0 |
| 81a | 60 | 1.4 |
| 46 | 60 | 1.4 |
| 81b | 64 | 1.2 |
| 83a | 34 | 1.4 |
| 84a | 31 | 2.2 |
| 84h | 23 | 2.2 |

For the skilled in the art it is evident from the experimental results shown above that compounds of the present invention are not only potent phosphodiesterase 2 inhibitors but also have good membrane permeability and low to moderate in vitro efflux.

Metabolic Stability

The metabolic stability of the compounds according to the invention has been investigated as follows:

The metabolic degradation of the test compound was assayed at 37° C. with pooled liver microsomes from various species. The final incubation volume of 100 µl per time point contains TRIS buffer pH 7.6 at room temperature (0.1 M), magnesium chloride (5 mM), microsomal protein (1 mg/mL for human and dog, 0.5 mg/mL for other species) and the test compound at a final concentration of 1 µM. Following a short preincubation period at 37° C., the reactions were initiated by addition of betanicotinamide adenine dinucleotide phosphate, reduced form (NADPH, 1 mM), and terminated by transferring an aliquot into solvent after different time points. After centrifugation (10000 g, 5 min), an aliquot of the supernatant was assayed by $LC_{10}$ MS/MS for the amount of parent compound. The half-life was determined by the slope of the semi-logarithmic plot of the concentration-time profile.

TABLE 4

Stability of compounds of the present invention in human liver microsomes.

| Ex. | Half-life—t1/2 [min] human |
| --- | --- |
| 1 | >130 |
| 2 | 120 |

TABLE 4-continued

Stability of compounds of the present invention in human liver microsomes.

| Ex. | Half-life—t1/2 [min] human |
| --- | --- |
| 37 | >130 |
| 17 | >130 |
| 25 | >130 |
| 21 | >130 |
| 3 | 72 |
| 68 | >130 |
| 69 | 53 |
| 70 | 63 |
| 71 | >130 |
| 51 | >130 |
| 53 | 120 |
| 88b | >130 |
| 82a | >130 |
| 81a | >130 |
| 46 | >130 |
| 81b | >130 |
| 83a | >130 |
| 86a | >130 |

For the skilled in the art it is evident from the experimental results shown above that compounds of the present invention are not only potent phosphodiesterase 2 inhibitors but also have good metabolic stability.

In view of their ability to inhibit the activity of phosphodiesterase 2 activity and their advantageous pharmacokinetics properties the compounds of general formula (I) according to the invention, or the physiologically acceptable salts thereof, are suitable for the treatment and/or preventative treatment of all those diseases or conditions which can be influenced by inhibition of PDE2 hyperactivity and/or cAMP and/or cGMP hypofunction. Therefore, compounds according to the invention, including the physiologically acceptable salts thereof, are particularly suitable for the prevention or treatment of diseases, particularly (1) disorders comprising the symptom of cognitive deficiency; (2) organic, including symptomatic, mental disorders, dementia; (3) mental retardation; (4) mood affective disorders; (5) neurotic, stress-related and somatoform disorders including anxiety disorders; (6) behavioural and emotional disorders with onset usually occurring in childhood and adolescence, attention deficit hyperactivity syndrome (ADHD) including Autism spectrum disorders; (7) disorders of psychological development, developmental disorders of scholastic skills; (8) schizophrenia and other psychotic disorders; (9) disorders of adult personality and behaviour; (10) mental and behavioural disorders due to psychoactive substance use; (11) extrapyramidal and movement disorders; (12) episodic and paroxysmal disorders, epilepsy; (13) Systemic atrophies primarily affecting the central nervous system, ataxia; (14) Behavioural syndromes associated with physiological disturbances and physical factors; (15) sexual dysfunction comprising excessive sexual drive; (16) factitious disorders; (17) obsessive-compulsive disorders; (18) depression; (19) neuropsychiatric symptoms (e.g. depressive symptoms in Alzheimer's disease); (20) mixed dementia; (21) cognitive impairment in schizoaffective disorder; (22) cognitive impairment in bipolar disorder and (23) cognitive impairment in major depressive disorder.

In addition, the compounds of the present invention can be used for the treatment, amelioration and/or prevention of cognitive impairment being related to perception, concentration, cognition, learning, attention or memory.

In addition, the compounds of the present invention can be used for the treatment amelioration and/or prevention of cognitive impairment being related to age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, schizophrenia with dementia or Korsakoff's psychosis.

In addition, the compounds of the present invention can be used for the treatment of Alzheimer's disease.

In addition compounds of the present invention can be used for the treatment of pain disorders, including but not limited to inflammatory, neuropathic and osteoarthritic pain.

In addition, the compounds of the present invention can be used for the treatment of sleep disorders, bipolar disorder, metabolic syndrome, obesity, diabetes mellitus, hyperglycemia, dyslipidemia, impaired glucose tolerance, or a disease of the testes, brain, small intestine, skeletal muscle, heart, lung, thymus or spleen.

Preferably the compounds according to the invention are suitable for the treatment of Alzheimer's Disease and for the treatment schizophrenia.

More preferably the compounds according to the invention are suitable for symptomatic treatment of Alzheimer's Disease and for the treatment of cognitive impairment associated with schizophrenia.

In particular the compounds according to the invention are suitable for symptomatic treatment of prodromal and mild-to-moderate Alzheimer's Disease and for the treatment of cognitive impairment associated with schizophrenia and symptomatic treatment of cognitive impairment associated with schizophrenia.

In a further aspect of the present invention the present invention relates to methods for the treatment or prevention of above mentioned diseases and conditions, which method comprises the administration of an effective amount of a compound of general formula (I), or the pharmaceutically acceptable salts thereof, to a human being.

The dose range of the compounds of general formula (I) applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I, including the pharmaceutically acceptable salts thereof, will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

The dosage for the combination partners mentioned above is usefully ⅕ of the lowest dose normally recommended up to 1/1 of the normally recommended dose.

Therefore, in another aspect, this invention relates to the use of a compound according to the invention or a pharmaceutically acceptable salt thereof combined with at least one of the active substances described above as a combination partner, for preparing a pharmaceutical composition which is suitable for the treatment or prevention of diseases or conditions which can be affected by inhibitors of phosphodiesterase 2. These are preferably pathologies related to PDE2 hyperactivity and/or cAMP and/or cGMP hypofunction, particularly one of the diseases or conditions listed above, most particularly prodromal and mild-to-moderate Alzheimer's Disease and cognitive impairment associated with schizophrenia. The use of the compound according to the invention in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a pharmaceutically acceptable salt thereof and at least one of the active substances described above as combination partners, optionally together with one or more inert carriers and/or diluents.

The compound according to the invention may both be present together in one formulation, for example a tablet or capsule, or separately in two identical or different formulations, for example as a so-called kit-of-parts.

EXAMPLES

The following examples are intended to illustrate the invention, without restricting its scope.

Chemical Manufacture

Abbreviations

ACN acetonitrile
APCI Atmospheric pressure chemical ionization
d day
Cy cyclohexane
DCM dichloromethane
DIPEA diisopropylethylamine
DMF dimethylformamide
ESI electrospray ionization (in MS)
EtOAc ethylacetate
EtOH ethanol
Exp. Example
GC gas chromatography
GC-MS coupled gas chromatography-mass spectrometry
h hour(s)
HATU O-(7-azabenzotriazol-1-yl)-N,N,N',N'-tetramethyl-uronium-Hexafluorophosphate
HCl hydrochloric acid
HPLC high performance liquid chromatography
HPLC-MS coupled high performance liquid chromatography-mass spectrometry
LC liquid chromatography
LC-MS liquid chromatography-mass spectrometry
M molar (mol/L)
MeOH methanol
min minute(s)
MS mass spectrometry
NaOH sodiumhydroxide
NMP 1-methyl-2-pyrrolidinone
NOE Nuclear Overhauser effect
PE petroleum ether
rt room temperature
$R_t$ retention time (in HPLC)
HATU 1-[Bis(dimethylamino)methylene]-1H-1,2,3-triazolo[4,5-b]pyridinium 3-oxidhexafluorophosphate
TBTU O-(benzotriazol-1-yl)-N,N,N',N'-tetramethyluroniumtetrafluoroborate
TEA triethylamine
TFA trifluoroacetic acid
THE tetrahydrofuran
TLC thin-layer chromatography
UPLC-MS ultra performance liquid chromatography-mass spectrometry Analytical Methods:
UPLC-MS, HPLC-MS, LC-MS:
Method 1:
Instrument: LC/MS ThermoFinnigan HPLC Surveyor DAD, MSQ single quadrupole
Column: Synergi Hydro RP100A, 2.5 μm, 3×50 mm
Mobile phase: A=H2O 90%+10% CH3CN+NH4COOH 10 mM
B=CH3CN 90%+H2O 10%+NH4COOH 10 mM

| Time in min: | % A | % B | Flow rate in mL/min |
|---|---|---|---|
| 0.00 | 100 | 0 | 1.2 |
| 0.50 | 100 | 0 | 1.2 |
| 6.50 | 0 | 100 | 1.2 |
| 7.50 | 0 | 100 | 1.2 |
| 8.00 | 100 | 0 | 1.2 |
| 9.00 | 100 | 0 | 1.2 |

Detection: UV 254 nm
Detection: Finnigan MSQ, single quadrupole
Ion source: APCI+/APCI−
Scan range: 100-900 amu
Method 2:
Instrument: LC/MS Waters Acquity UPLC System DAD, SQD single quadrupole
Column: BEH C18 1.7 m 2.1×50 mm, Temp 35° C.
Mobile phase: A=$H_2O$ 90%+$CH_3CN$ 10%+$NH_4COOH$ 5 mM
B=$CH_3CN$ 90%+$H_2O$ 10%

| Time in min: | % A | % B | Flow rate in mL/min |
|---|---|---|---|
| 0.00 | 100 | 0 | 0.7 |
| 1.20 | 0 | 100 | 0.7 |
| 1.45 | 0 | 100 | 0.7 |
| 1.55 | 100 | 0 | 0.7 |
| 1.75 | 100 | 0 | 0.7 |

Detection: UV 254 nm
Detection: SQD, single quadrupole
Ion source: ES+/ES−
Scan range: 90-900 amu
Method 3:
Instrument: LC/MS Waters Alliance 2695 HPLC System DAD, Quattro Micro Triple quadrupole
Column: Atlantis dC18 5 μm 4,6×50 mm, Temp 35° C.
Mobile phase: A=$H_2O$ 90%+10% $CH_3CN$+$CF_3COOH$ 0.05%
B=$CH_3CN$ 90%+10% $H_2O$

| Time in min: | % A | % B | Flow rate in mL/min |
| --- | --- | --- | --- |
| 0.00 | 100 | 0 | 1.3 |
| 0.70 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
METHOD 4:
Instrument: LC/MS Waters Alliance 2695 HPLC System DAD, Quattro Micro Triple quadrupole
Column: XBridge Phenyl 3.5 μm 3×30 mm, Temp 35° C.
Mobile phase: A=$H_2O$ 90%+10% $CH_3CN$+$NH_4HCO_3$ 5 mM
   B=$CH_3CN$ 90%+10% $H_2O$

| Time in min: | % A | % B | Flow rate in mL/min |
| --- | --- | --- | --- |
| 0.00 | 100 | 0 | 1.3 |
| 4.50 | 0 | 100 | 1.3 |
| 5.80 | 0 | 100 | 1.3 |
| 6.00 | 100 | 0 | 1.3 |

Detection: UV 254 nm
Detection: Quattro Micro, triple quadrupole
Ion source: ES+
Scan range: 90-1000 amu
Method 5:
Instrument: LC/MS Waters Acquity UPLC System DAD, SQD single quadrupole
Column: BEH C18 1.7 μm 2.1×50 mm, Temp 35° C.
Mobile phase: A=$H_2O$ 90%+$CH_3CN$ 10%+$NH_4HCO_3$ 5 mM
   B=$CH_3CN$ 90%+$H_2O$ 10%

| Time in min: | % A | % B | Flow rate in mL/min |
| --- | --- | --- | --- |
| 0.00 | 100 | 0 | 0.70 |
| 1.20 | 100 | 0 | 0.70 |
| 1.45 | 0 | 100 | 0.70 |
| 1.55 | 0 | 100 | 0.70 |
| 1.75 | 100 | 0 | 0.70 |

Detection: UV 254 nm
Detection: SQD, single quadrupole
Ion source: ES+/ES−
Scan range: 90-900 amu
Method 6:
Instrument: LC/MS Waters Acquity System DAD, SQD single quadrupole
Column: XBridge C18 2.5 μm 3.0×30 mm, Temp 60° C.
Mobile phase: A=$H_2O$+TFA 0.1%
   B=$CH_3CN$

| Time in min: | % A | % B | Flow rate in mL/min |
| --- | --- | --- | --- |
| 0.00 | 98 | 2 | 1.5 |
| 1.3 | 1 | 99 | 1.5 |
| 1.5 | 1 | 99 | 1.5 |
| 1.6 | 98 | 2 | 1.5 |

Method 7:
Instrument: LC/MS Waters Acquity System DAD, SQD single quadrupole
Column: XBridge C18 2.5 μm 3.0×30 mm, Temp 60° C.
Mobile phase: A=$H_2O$+$NH_4OH$ 0.1%
   B=$CH_3CN$

| Time in min: | % A | % B | Flow rate in mL/min |
| --- | --- | --- | --- |
| 0.00 | 95 | 5 | 1.5 |
| 1.3 | 1 | 99 | 1.5 |
| 1.5 | 1 | 99 | 1.5 |
| 1.6 | 95 | 5 | 1.5 |

Method 8:
Instrument: LC/MS Agilent 1100 System DAD
Column: Sunfire C18 2.5 μm 3.0×30 mm, Temp 60° C.
Mobile phase: A=$H_2O$+TFA 0.1%
   B=$CH_3CN$

| Time in min: | % A | % B | Flow rate in mL/min |
| --- | --- | --- | --- |
| 0.00 | 98 | 2.0 | 2.0 |
| 1.2 | 0.0 | 100 | 2.0 |
| 1.4 | 0.0 | 100 | 2.0 |

Method 10:
Instrument: LC/MS ThermoFinnigan HPLC Surveyor DAD, LCQFeet Ion Trap
Column: Xselect CSH, 2.5 μm, 4,6×50 mm
Mobile phase: A=$H_2O$ 90%+10% $CH_3CN$+HCOOH 0.1%
   B=$CH_3CN$ 90%+$H_2O$ 10%+HCOOH 0.1%

| Time in min: | % A | % B | Flow rate in mL/min |
| --- | --- | --- | --- |
| 0.00 | 100 | 0 | 1.4 |
| 4.00 | 0 | 100 | 1.4 |
| 5.30 | 0 | 100 | 1.4 |
| 5.50 | 100 | 0 | 1.4 |
| 6.00 | 100 | 0 | 1.4 |

Detection: UV 254 nm
Detection: Finnigan Fleet, Ion Trap
Ion source: ES+
Scan range: 100-900 amu
GC/MS Method
Method 9:
Instrument: GC/MS Thermo Scientific TRACE GC ULTRA, DSQ II MS single quadrupole
Column: Agilent DB-5MS, 25 m×0.25 mm×0.25 um
Carrier gas: Helium, 1 mL/min constant flow
Oven Program: 50° C., to 100° C. in 10° C./min, to 200° C. in 20° C./min, to 320° C. in 30° C./min (hold 10 min).
Detection: DSQ II MS single quadrupole
   Ion source: EI
   Scan range: 50-450 amu
Chiral HPLC Methods:
Instrument: HPLC Agilent 1100 (DAD equipped; UV Detection: 230 nm); flow rate: 1 mL/min; column temperature: 25° C.
Method C1
column: Daicel Chiralpack AD-H; eluent:Hexane:Isopropanol=70:30
Method C2
column: Daicel Chiralpack AD-H; eluent:Hexane:Isopropanol=60:40

Method C3
column: Daicel Chiralpack AD-H; eluent:Hexane:Isopropanol=80:20
Method C4
column: Daicel Chiralcel OJ-H; eluent:Hexane:EtOH=80:20
Method C5
column: Daicel Chiralcel OJ-H; eluent:Hexane:EtOH=85:15
Method C6
column: Daicel Chiralcel OJ-H; eluent:Hexane:EtOH=70:30
Method C7
column: Daicel Chiralcel AS-H; eluent:Hexane:EtOH=75:25

NMR Equipment:

The 1H NMR spectra were recorded on a Bruker Avance III (500 MHz) or a Varian 400 (400 MHz) or Varian Mercury (300 MHz) instrument using deuterated dimethylsulfoxide (DMSO-d6) as the solvent with tetramethylsilane (TMS) and residual solvent peak as an internal standard. Chemical shifts are reported in b values (ppm) relative to TMS.

Purification:

The most suitable purification techniques applied for the purification of compounds of the present invention are direct phase silica gel flash chromatography and reverse phase chromatography, unless otherwise specifically stated.

General Comment Concerning the Presentation of the Structures

Compounds with stereogenic centre(s): The structures depicted in the experimental section will not necessarily show all the stereochemical possibilities of the compounds but only one.

The structural presentation of the compounds in the experimental section will show a stereochemical bond only in case where the absolute stereochemistry is known.

The structural presentation of the compounds in the experimental section with unknown absolute stereochemistry will show a planar bond plus an additional comment that indicates if the described compound is a racemic mixture, a single stereoisomer and where applicable the relative stereochemistry.

Two examples are given below.

Example 1: The Presented Chemical Structure is Depicted as

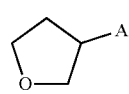

Racemic mixture

The added term racemic mixture points to the two stereochemical options and thus the manufactured compounds is a mixture of:

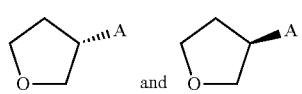

When racemic mixtures of above depicted structures are separated, the single stereoisomers are depicted as:

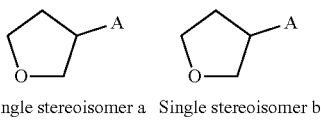

Single stereoisomer a    Single stereoisomer b

The added term 'single stereoisomer' and the planar bond indicates that the absolute configuration is unknown.

Single stereoisomer a is assigned to the first eluting isomer in chiral HPLC, single stereoisomer b is assigned to the second eluting isomer in chiral HPLC.

Example 2: The Presented Chemical Structure is Depicted as

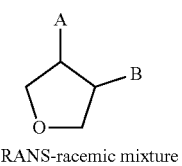

TRANS-racemic mixture

The added term 'TRANS-racemic mixture' points to the two stereochemical options and thus the manufactured compounds is a mixture of:

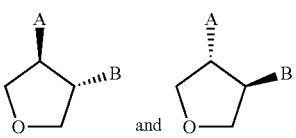

The same principles applies to 'CIS-racemic mixture'.

When racemic mixtures of above depicted structures are separated, the single stereoisomers are depicted as:

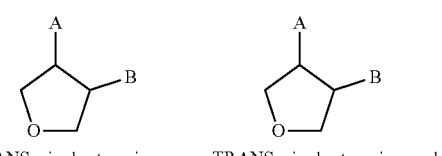

TRANS- single stereoisomer a    TRANS- single stereoisomer b

The added term 'TRANS-single stereoisomer' indicates a relative configuration known (trans) and the planar bond indicates the unknown absolute configuration. The same principles applies to 'CIS-single stereoisomer'.

Single stereoisomer a is assigned to the first eluting isomer in chiral HPLC, single stereoisomer b is assigned to the second eluting isomer in chiral HPLC.

Experimental

The following intermediates and examples are intended to illustrate the invention, without restricting its scope.

Intermediates

Intermediate 1

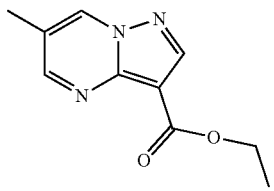

To a solution of 3-amino-4-carbethoxypyrazole (4 g, 25.27 mmol) in absolute EtOH (40 mL), 1,1,3,3-Tetra-ethoxy-2-methyl-propane (6.34 g, 26.53 mmol) was added followed by 13.90 mL of a 1M solution of HCl in dioxane. The mixture was heated at 80 C overnight. Solvents were evaporated, then DCM and water were added. Phases were separated, organics washed with a saturated solution of NaCl, dried over sodium sulphate and evaporated to obtain 5.17 g of the title compound LC-MS (Method 2): $R_t$=0.73 min
MS (ESI pos): m/z=206 (M+H)$^+$

Intermediate 2

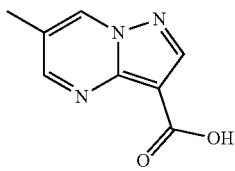

Intermediate 1 (5 g) was dissolved in a mixture of THF/water (1:1, 100 mL) and stirred at room temperature for 48 hrs. The resulting suspension was diluted with water and 70 mL of EtOAc were added. Phases were separated, aqueous phases were treated with a 4N solution of HCl (ca 20 mL). A white solid formed. The mixture was cooled at 0° C., then the white solid formed collected by filtration and dried under vacuum at 65° C. to obtain 3.50 g of the title compound.

LC-MS (Method 3): $R_t$=1.62 min
MS (ESI pos): m/z=178 (M+H)$^+$

Intermediate 3

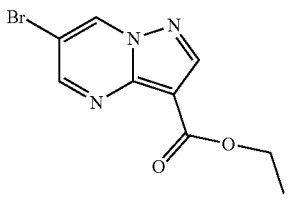

To a solution of 2-Bromo-malonaldehyde (9.73 g; 64 mmol) in EtOH (100 mL) at 70° C., 3-amino-4-carbethoxy-pyrazole (10 g, 64 mmol), and AcOH (100 mL) were added and the mixture stirred at 70° C. for 1 h. Solvents were evaporated, the residue treated with DCM (100 mL) and a 1N solution of NaOH (100 mL). Phases were separated, organics washed with a saturated solution of NaCl, dried over sodium sulphate and evaporated. The crude was purified flash chromatography (eluent 10:1 PE/EtOAc) to obtain 15 g of the title compound as white solid.

LC-MS (Method 2): $R_t$=0.98 min
MS (ESI pos): m/z=271 (M+H)$^+$

Intermediate 4

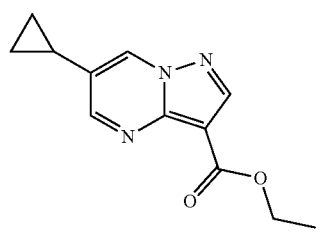 [SMILES: CCOC(=O)c1cnn2cc(C3CC3)cnc12]

Intermediate 3 (5 g, 18.5 mmol) was suspended in dry toluene (50 mL) and 5 mL of water were added. To this mixture, potassium cyclopropyltrifluoroborate (4 g, 28 mmol) was added followed by 2-dicyclohexylphosphino-2',6'-di isopropoxy 1,1'-biphenyl (0.864 g, 1.85 mmol), palladium acetate (0.208 g, 0.93 mmol) and potassium carbonate (7.7 g, 55 mmol). Mixture was refluxed at 130° C. for 3 hrs, then cooled to room temperature, filtered over celite and washed with AcOEt and then EtOH. Solvent was evaporated under vacuum and the crude used in the next step without further purification.

LC-MS (Method 2): $R_t$=0.9 min
MS (ESI pos): m/z=232 (M+H)$^+$

Intermediate 5

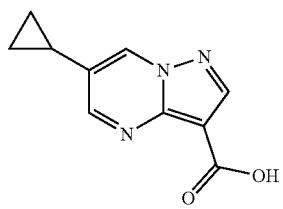 [SMILES: O=C(O)c1cnn2cc(C3CC3)cnc12]

Intermediate 4 (4 g, 17.5 mmol) was suspended in 50 ml of EtOH, 8 ml of 4N NaOH and 30 ml of water and stirred overnight. EtOH was evaporated and a 4 N solution of HCl added. The solid formed was filtered, washed with water and dried under vacuum at 70° C. overnight to obtain 3.6 g of the title compound.

LC-MS (Method 3): $R_t$=2.75 min
MS (ESI pos): m/z=204 (M+H)$^+$

Intermediate 6

Intermediate 6 was prepared as described in WO 2010/007074 starting from commercially available (Z) 3-(diethylamino)-2-fluoroprop-2-enal (1.34 mL, 9.0 mmol) and 3-amino-4-carbethoxypyrazole (2.1 g, 13.6 mmol) to obtain 0.53 g of the title compound.

$^1$H NMR (300 MHz, CDCl3): δ ppm 1.44-1.39 (t, 3H), 4.47-4.40 (q 2H) 8.57 (s, 1H) 8.7 (m, 1H), 8.8 (d, 1H)

Intermediate 7

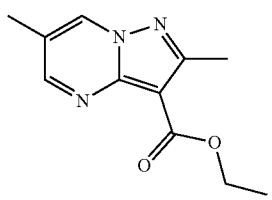 [SMILES: CCOC(=O)c1c(C)nn2cc(C)cnc12]

To a solution of 5-amino-3-methyl-1H-pirazole-4-carboxylic acid ethyl ester (1 g, 5.91 mmol) in absolute EtOH (25 mL), 1,1,3,3-Tetraethoxy-2-methyl-propane (1.4 g, 6.2 mmol) was added followed by 1.63 mL of a 4N solution of HCl in dioxane. Mixture was heated at 80° C. for 5 hrs, left at room temperature overnight and then solvents were evaporated to dryness. The violet solid obtained was dissolved in DCM, water was added and the phases separated.

The organic phases were dried over sodium sulfate and concentrated under vacuum to obtain 1.26 g of title compound used for next step without further purification.

LC-MS (Method 2): $R_f$=0.79 min
MS (ESI pos): m/z=224 (M+H)$^+$

Intermediate 8

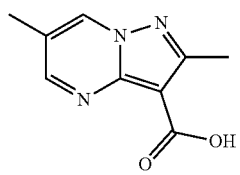

To a solution of intermediate 7 (1.26 g, 5.75 mmol) in THF (25 mL) and water (25 mL) 1.5 mL of a 1N solution of sodium hydroxide were added and the mixture heated at heated at 60° C. for 2 h. Solvent was evaporated, water was added and 30 ml of a 12N solution of HCl added until pH 2. The solid formed was filtered, washed with water and dried at 70° C. under vacuum to obtain 0.9 g of title compound as white solid.

LC-MS (Method 1): $R_f$=0.27 min
MS (APCI): m/z=192 (M+H)$^+$

Intermediate 9

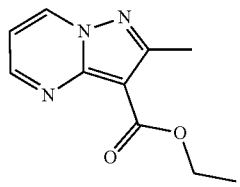

To a solution of 5-amino-3-methyl-1H-pyrazole-4-carboxiic acid ethyl ester (4 g, 23.64 mmol) in absolute EtOH (80 mL), 1,1,3,3-tetraethoxypropane (5.96 mL, 23.64 mmol) and 5.9 mL of a 4N solution of HCl in dioxane were added. The resulting mixture was heated at 80° C. 3 hrs. Solvents were evaporated, the residue was diluted with DCM and water. Organic layer was separated, dried over sodium sulphate and evaporated to obtain the title compound as white solid (3.6 g)

LC-MS (Method 1): $R_f$=263 min
MS (APCI): m/z=206 (M+H)$^+$

Intermediate 10

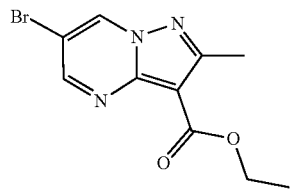 [SMILES: CCOC(=O)c1c(C)nn2cc(Br)cnc12]

To a solution of intermediate 9 (3.6 g, 17.54 mmol) in AcOH (70 mL) bromine (2.26 mL) was added drowpwise. The mixture was stirred at room temperature overnight then carefully poured into 500 mL of water and extracted with EtOAc (3×100 mL). Organic phases were collected and washed with 100 mL of a 5% solution of Na2S2O3 and then with 100 mL of a saturated solution of NaCl, dried over sodiumsulphate and concentrated under vacuum.

Crude was purified by flash chromatography (eluent: DCM/EtOAc; gradient from 100% to 70%) to obtain the title compound as white solid (2.1 g)

LC-MS (Method 1): $R_f$=3.52 min
MS (APCI): m/z=284 (M+H)$^+$

Intermediate 11

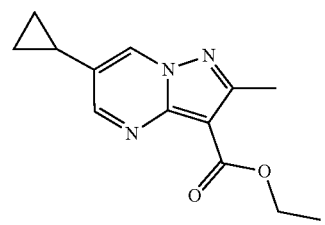 [SMILES: CCOC(=O)c1c(C)nn2cc(C3CC3)cnc12]

To a solution of intermediate 10 (2.05 g, 7.22 mmol) in toluene (40 mL) water (4 mL) was added followed by potassium cyclopropyltrifluroborate (1.6 g, 10.82 mmol), palladium(II) acetate (0.08 g, 0.36 mmol), dicyclohexylphosphino-2',6'-di-i-propoxy dl-1,1'-biphenyl (RUPHOS, 0.34 g, 0.72 mmol) and potassium carbonate (3 g, 21.65 mmol). Mixture was heated at 130° C. for 3 hrs then cooled to room temperature, filtered over celite and washed with AcOEt. Organic layer was dried and evaporated to obtain the title compound (1.5 g) used for the next step without further purification.

LC-MS (Method 2): $R_t$=0.92 min
MS (ESI pos): m/z=246 (M+H)$^+$

Intermediate 12

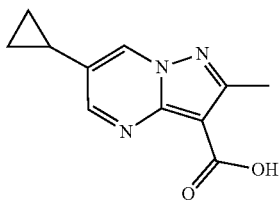 [SMILES: Cc1nn2cc(C3CC3)cnc2c1C(=O)O]

To a solution of intermediate 11 (1.5 g, 6.2 mmol) in absolute EtOH (30 mL) water (10 mL) was added followed by 7.7 mL of a 8N solution of NaOH. Mixture was stirred at room temperature overnight, then solvent evaporated and a 4N solution of HCl added until pH=1. The solid formed was filtered, washed with water and dried under vacuum at 70° C. overnight (1.5 g).

LC-MS (Method 1): $R_t$=0.6 min
MS (APCI): m/z=218 (M+H)$^+$

Intermediate 13

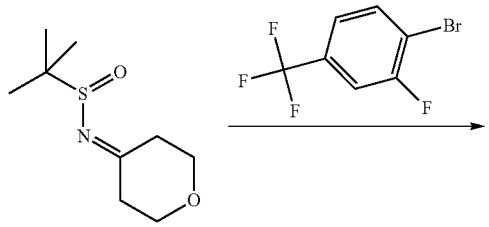

-continued

To a solution of 4-bromo-3-fluoro-benzotrifluoride (585 mg, 2.36 mmol) in 15 mL of THF, stirred at −75° C. under nitrogen atmosphere, 1.53 mL (2.6 mmol) of a 1.7M solution of tert-butyllithium in pentane were added dropwise. The reaction mixture was stirred at −60° C. for 15 minutes then a solution of 2-methyl-propane-2-sulfinic acid-(tetrahydro-pyran-4-ylidene)-amide (400 mg, 1.97 mmol; prepared as described in literature: WO2005/87751 A2) in 10 mL of THF was added dropwise. The reaction mixture was allowed to reach room temperature and stirred for 1 hr. A saturated ammonium chloride solution was added and the reaction mixtures was extracted with ethyl acetate. The organic phases were collected, dried over sodium sulfate and concentrated under vacuum. The crude obtained was purified by flash chromatography (eluent: cyclohexane/AcOEt; gradient from 12% to 100% of AcOEt).

The oil obtained was diluted in 2 mL of 1,4-dioxane, 0.4 mL of a 4 M solution of hydrochloric acid in 1,4-dioxane were added, the reaction mixture was stirred at room temperature for 1 hr and then concentrated under vacuum to obtain 100 mg of the title compound as white solid.

LC-MS (Method 2): $R_t$=0.90 min
MS (ESI pos): m/z=264 (M+H)$^+$

The following Amine Intermediates were prepared in analogy to Intermediate 13 starting from the corresponding commercially available bromo-aryl/heteroaryl or iodo-aryl/heteroaryl derivative:

| Starting | | Amine intermediate | MS m/z | $R_t$ (min) | Method |
|---|---|---|---|---|---|
| 4-Chloro-2-fluoro-iodobenzene | 14 | 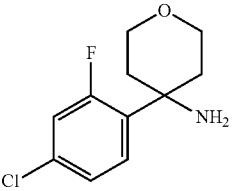 [SMILES: NC1(c2ccc(Cl)cc2F)CCOCC1] | 230, 232 (M + H)+ | 0.79 | Method 2 |

-continued
| Starting | Amine intermediate | | MS m/z | R$_t$ (min) | Method |
|---|---|---|---|---|---|
| 4-Iodo-benzo-trifluoride | 15 | 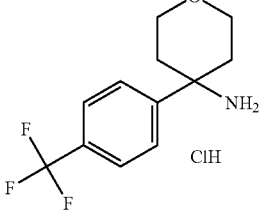 | 246 (M + H)+ | 0.66 | Method 2 |
| — | 16 Commercially available from ENAMINE-BB (Cat. Number EN300-185595) | 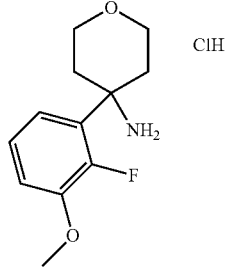 [SMILES: COc1cccc(C2(N)CCOCC2)c1F ; Cl] | — | — | — |
| 2-Bromo-quinoline | 17 | 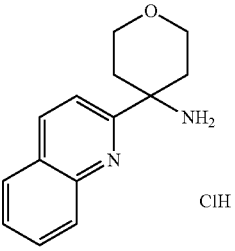 [SMILES: NC1(c2ccc3ccccc3n2)CCOCC1 ; Cl] | 229 (M + H)+ | 0.69 | Method 2 |
| — | 18 Commercially available from ENAMINE-BB (Cat. Number EN300-50665) | 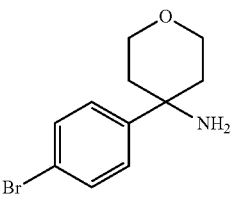 [SMILES: NC1(c2ccc(Br)cc2)CCOCC1] | — | — | — |
| 4-Bromo-1-(difluorometh-oxy)-2-fluorobenz-ene | 19 | 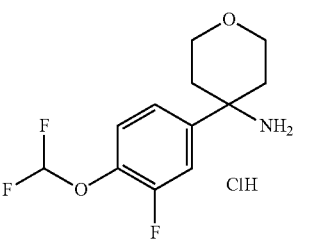 [SMILES: NC1(c2ccc(OC(F)F)c(F)c2)CCOCC1 ; Cl] | 262 (M + H)+ | 0.68 | Method 2 |
| 4-Chloro-3-fluoro-iodobenzene | 20 | 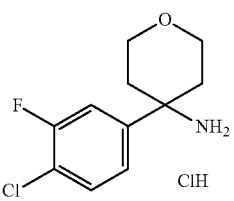 [SMILES: NC1(c2ccc(Cl)c(F)c2)CCOCC1 ; Cl] | 230, 232 (M + H)+ | 0.77 | Method 2 |

-continued
| Starting | Amine intermediate | | MS m/z | R_t (min) | Method |
|---|---|---|---|---|---|
| 2-Bromo-3-fluoro-5-(trifluoromethyl)pyridine | 21 | 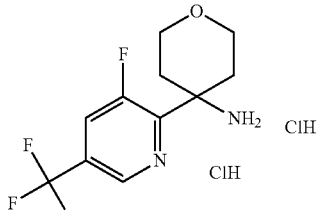 | 265 (M + H)+ | 0.83 | Method 2 |
| 2-Iodo-5-(trifluoromethyl)pyridine | 22 | 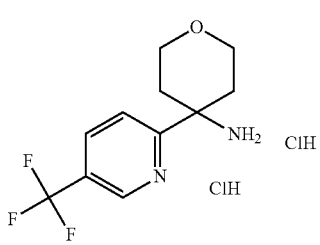 [SMILES: NC1(c2ccc(C(F)(F)F)cn2)CCOCC1 ; Cl ; Cl] | 247 (M + H)+ | 0.75 | Method 2 |
| 5-Iodo-2-(trifluoromethyl)pyridine | 23 | 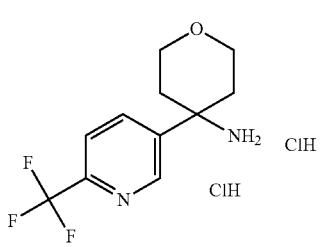 [SMILES: NC1(c2ccc(C(F)(F)F)nc2)CCOCC1 ; Cl ; Cl] | 247 (M + H)+ | 0.71 | Method 2 |
| 5-Bromo-3-fluoro-2-(trifluoromethyl)pyridine | 24 | 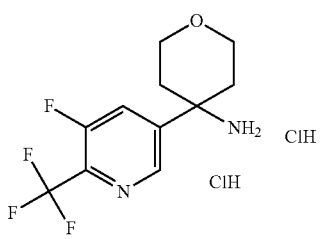 [SMILES: NC1(c2cnc(C(F)(F)F)c(F)c2)CCOCC1 ; Cl ; Cl] | 265 (M + H)+ | 0.81 | Method 2 |
| 2-Chloro-4-fluoro-iodobenzene | 25 | 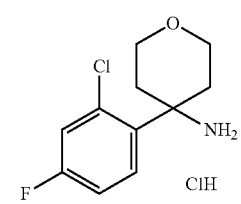 [SMILES: NC1(c2ccc(F)cc2Cl)CCOCC1 ; Cl] | 230, 232 (M + H)+ | 0.59 | Method 2 |

Intermediate 26

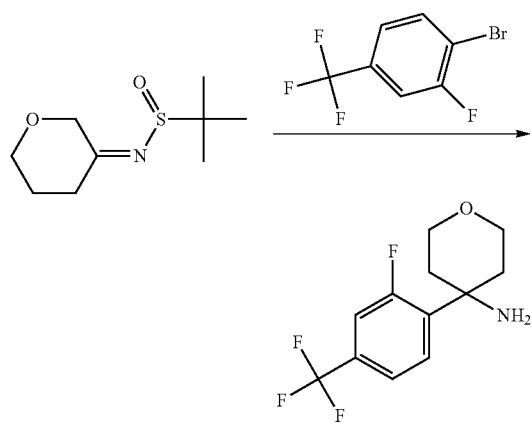

Intermediate 29

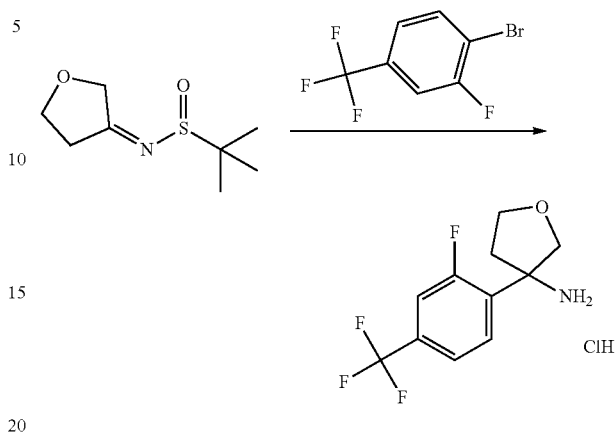

Intermediate 26 was prepared as described for Intermediate 13 starting from commercially available 4-bromo-3-fluoro-benzotrifluoride (560 mg, 2.30 mmol) and 2-methyl-propane-2-sulfinic acid [dihydro-pyran-(3Z)-ylidene]-amide (390 mg, 1.92 mmol; prepared in analogy to 2-methyl-propane-2-sulfinic acid-(tetrahydro-pyran-4-ylidene)-amide, described in WO2005/87751 A2) to obtain 120 mg of the title compound, as racemic mixture.

LC-MS (Method 2): $R_t$=1.00 min
MS (ESI pos): m/z=264 (M+H)$^+$

The following Amine Intermediates were prepared in analogy to Intermediate 26 starting from the corresponding commercially available bromo-aryl derivative:

Intermediate 29 was prepared as described for Intermediate 13 starting from commercially available 4-bromo-3-fluoro-benzotrifluoride (462 g, 1.90 mmol) and 2-methyl-propane-2-sulfinic acid [dihydro-furan-(3Z)-ylidene]-amide (300 mg, 1.58 mmol; prepared in analogy to 2-methyl-propane-2-sulfinic acid-(tetrahydro-pyran-4-ylidene)-amide, described in WO2005/87751 A2) to obtain 50 mg of the title compound, as racemic mixture.

LC-MS (Method 2): $R_t$=0.90 min
MS (ESI pos): m/z=250 (M+H)$^+$

The following Amine Intermediates were prepared in analogy to Intermediate 29 starting from the corresponding commercially available bromo-aryl/heteroaryl or iodo-aryl/heteroaryl derivative:

| Starting | Amine intermediate | | MS m/z | $R_t$ (min) | Method |
|---|---|---|---|---|---|
| 4-Bromo-benzotrifluoride | 27 | Racemic mixture | 246 (M + H)+ | 0.92 | Method 2 |
| 1-Bromo-4-(trifluoromethoxy)benzene | 28 | Racemic mixture | 262 (M + H)+ | 0.95 | Method 2 |

| Starting | Amine intermediate | | MS m/z | $R_t$ (min) | Method |
|---|---|---|---|---|---|
| 4-Iodobenzo-trifluoride | 30 Racemic mixture | [structure: 4-(trifluoromethoxy)phenyl-tetrahydrofuran-3-amine·HCl] | 232 (M + H)+ | 0.83 | Method 2 |
| 4-Chloro-2-fluoroiodo-benzene | 31 Racemic mixture | [structure: 4-chloro-2-fluorophenyl-tetrahydrofuran-3-amine·HCl] | 216, 218 (M + H)+ | 0.75 | Method 2 |
| 2-Bromo-3-fluoro-5-(trifluoromethyl)pyridine | 32 Racemic mixture | [structure: 3-fluoro-5-(trifluoromethyl)pyridin-2-yl tetrahydrofuran-3-amine·2ClH] | 251 (M + H)+ | 0.76 | Method 2 |
| 5-Iodo-2-(trifluoromethyl)pyridine | 33 Racemic mixture | [structure: 6-(trifluoromethyl)pyridin-3-yl tetrahydrofuran-3-amine·ClH] | 233 (M + H)+ | 0.68 | Method 2 |
| 2-Iodo-5-(trifluoromethyl)pyridine | 34 Racemic mixture | [structure: 5-(trifluoromethyl)pyridin-2-yl tetrahydrofuran-3-amine·2ClH] | 233 (M + H)+ | 0.70 | Method 2 |

Intermediate 35

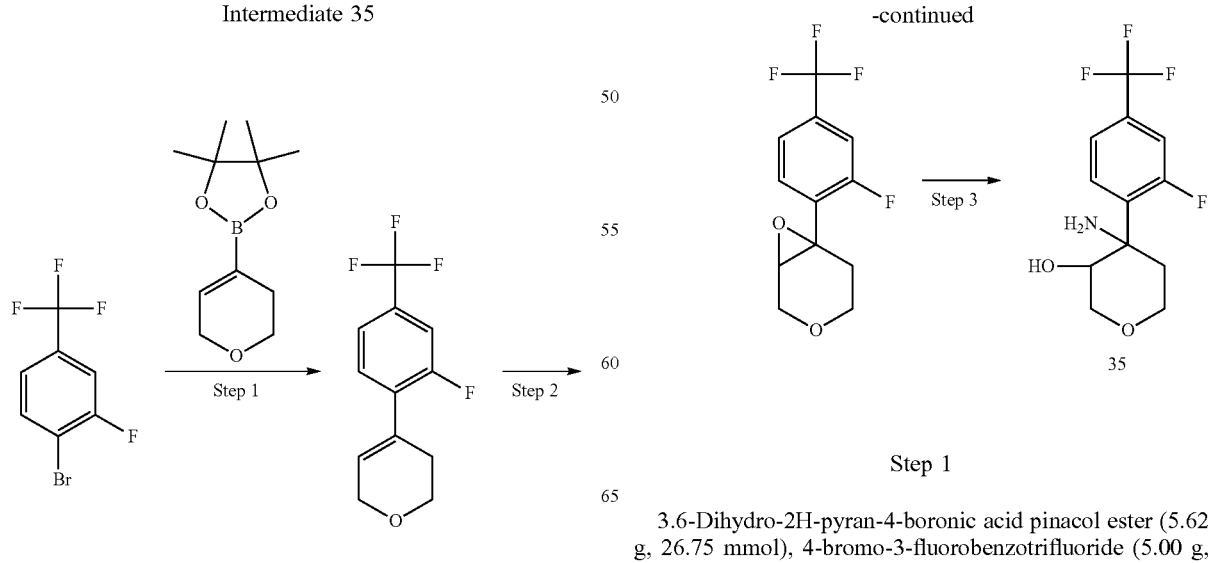

Step 1

3.6-Dihydro-2H-pyran-4-boronic acid pinacol ester (5.62 g, 26.75 mmol), 4-bromo-3-fluorobenzotrifluoride (5.00 g, 20.58 mmol), potassium carbonate (8.53 g, 61.73 mmol) and 1,1′-bis(diphenylphosphino)ferrocenedichloro palladium(II) (753 mg, 1.03 mmol) were suspended in 50 mL of 1,4-dioxane and 10 mL of water. The reaction mixture was refluxed for 3 hrs, solvents were evaporated and the crude was extracted with ethyl acetate (50 mL) and water (50 mL). Organic layer was separated, dried over sodium sulfate and evaporated. The crude obtained was purified by flash chromatography (eluent: cyclohexane/AcOEt; gradient from 40% to 100% of AcOEt) to obtain 4.0 g of the title compound as clear oil.

GC-MS (Method 9): $R_t$=7.76 min
MS: m/z=246 (M)+

Step 2

To a solution of 4-(2-Fluoro-4-trifluoromethyl-phenyl)-3,6-dihydro-2H-pyran (obtained as described in Step 1; 7.0 g, 25.18 mmol) in 150 mL of dichloromethane, stirred at 0° C., 3-chloroperoxybenzoic acid (11.3 g, 50.37 mmol) was added portionwise. The reaction mixture was allowed to reach room temperature and stirred overnight. The reaction mixture was cooled to 0° C. and the precipitate formed was filtered off. The organic solution was washed twice with an aqueous saturated solution of potassium carbonate, dried over sodium sulfate and concentrated under vacuum. The crude obtained was purified by flash chromatography (eluent: cyclohexane/AcOEt; gradient from 50% to 100% of AcOEt) to obtain 4.2 g of the title compound.

GC-MS (Method 9): $R_t$=7.68 min
MS: m/z=262 (M)+

Step 3

To a solution of 6-(2-Fluoro-4-trifluoromethyl-phenyl)-3,7-dioxa-bicyclo[4.1.0]heptane (obtained as described in Step 2; 1.64 g, 6.25 mmol) in 10 mL of acetonitrile, stirred under nitrogen atmosphere at −45° C., trifluoromethane sulfonic acid (1.88 g, 12.5 mmol) was added dropwise. The reaction mixture was allowed to reach room temperature and stirred for 2.5 hrs. 10 mL of water were added, the reaction mixture was warmed to 100° C. and acetonitrile was distilled out. The reaction mixture was stirred at 100° C. for 5 hrs, then cooled to room temperature and stirred overnight. The reaction mixture was diluted with dichloromethane and phases were separated. The aqueous phase was treated with a 4M solution of NaOH until basic pH and extracted with dichloromethane. The organic phase was dried over sodium sulfate and concentrated under vacuum to give 290 mg of the final compound (crude colorless oil), 4-Amino-4-(2-fluoro-4-trifluoromethyl-phenyl)-tetrahydro-pyran-3-ol, as racemic mixture (TRANS/CIS diastereoisomeric ratio 85:15, determined by NMR).

The crude was used in the next step without any further purification.

LC-MS (METHOD 2): $R_t$=0.77 min
MS (ESI pos): m/z=280 (M+H)+
1H NMR (500 MHz, DMSO-d6) δ 7.59-7.47 (m, 3H), 4.74 (d, J=5.8 Hz, 1H), 4.04 (dd, J=11.7, 1.5 Hz, 1H), 3.90 (ddd, J=12.5, 11.0, 2.0 Hz, 1H), 3.74 (d, J=5.8 Hz, 1H), 3.67 (dd, J=11.1, 4.1 Hz, 1H), 3.56-3.51 (m, 1H), 2.51-2.44 (m, 1H), 2.09 (br s, 1H), 1.56 (m, 1H).

NOE: 2.09 (NH2): 3.74; 4.04, 4.74 (OH): 3.55; 2.45

The following Amino-alcohol Intermediate were prepared in analogy to Intermediate 34 starting from the corresponding commercially available bromo-heteroaryl:

| Starting | Amino-alcohol intermediate | | MS m/z | $R_t$ (min) | Method |
|---|---|---|---|---|---|
| 5-Bromo-2-(trifluoromethyl)pyridine | 36 Trans racemate | (structure) | 263 (M + H)+ | 0.90 | Method 1 |

Relative stereochemistry of intermediate 36 assigned by NMR and NOE:

1H NMR (500 MHz, DMSO-d6) δ 8.87 (d, J=2.3 Hz, 1H, 13), 8.10 (ddd, J=8.3, 2.4, 0.8 Hz, 1H), 7.81 (dd, J=8.3, 0.8 Hz, 1H), 4.78 (d, J=5.9 Hz, 1H), 4.05 (dd, J=11.6, 1.5 Hz, 1H), 3.91 (td, J=11.7, 2.3 Hz, 1H), 3.68 (ddd, J=11.1, 4.9, 2.2 Hz, 1H), 3.56 (dd, J=11.7, 2.4 Hz, 1H), 3.47 (d, J=5.9 Hz, 1H), 2.49-2.44 (m, 1H), 2.12 (s, 2H), 1.49 (dd, J=13.1, 1.9 Hz, 1H).

NOE: 2.12 (NH2): 3.47; 3.91; 4.05, 4.78 (OH): 3.56; 2.48

Intermediate 37

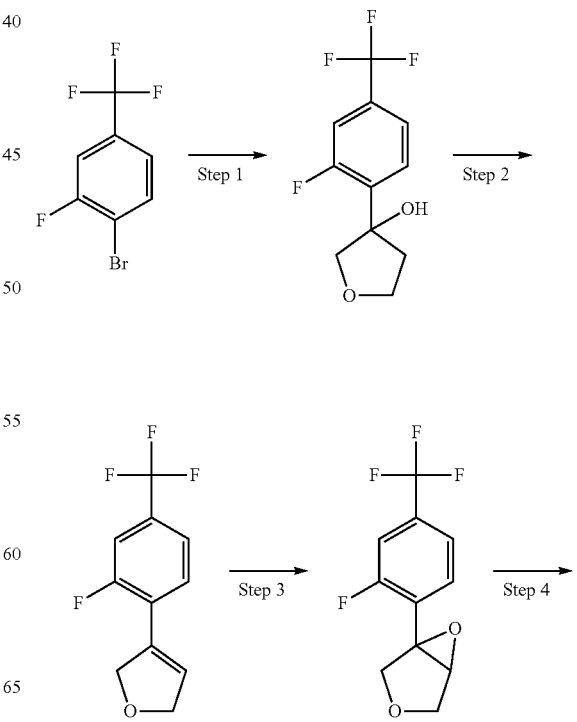

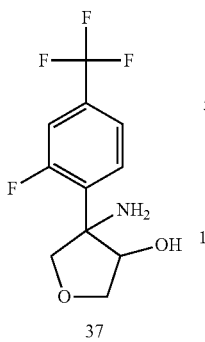

37

Step 1 tert-Butyllithium (21.8 mL, 1.7M in pentane, 37.0 mmol) was added dropwise to 4-bromo-3-fluorobenzotrifluoride (5.00 g, 20.58 mmol) in THF (50 mL) at −70° C. After 1 h, 3-oxotetrahydrofuran (1.78 g, 20.58 mmol) in THF was added dropwise. The reaction mixture was warmed to −10° C. mixture and quenched with $NH_4Cl$ saturated solution. Ethyl acetate was added, the organic layer was separated, dried over sodium sulfate and evaporated. The crude obtained was purified by flash chromatography (eluent: cyclohexane/AcOEt; gradient from 0% to 80% of AcOEt) to obtain 1.6 g of the 3-(2-fluoro-4-trifluoromethyl-phenyl)-tetrahydro-furan-ol.

GC-MS (Method 9): $R_t$=7.58 min
MS: m/z=250 (M)+

Step 2 p-Toluenesulfonic acid monohydrate (1.75 g, 9.19 mmol) was added to 3-(2-fluoro-4-trifluoromethyl-phenyl)-tetrahydro-furan-ol (obtained as described in Step 1; 2.3 g, 9.19 mmol) in toluene (20 mL). After refluxing for 1 h, volatiles were evaporated, DCM and water were added, the organic layer was separated, dried over sodium sulfate and evaporated to obtain 2.0 g (77% content) of crude 3-(2-fluoro-4-trifluoromethyl-phenyl)-2,5-dihydro-furan, that was used without further purification.

GC-MS (Method 9): $R_t$=7.12-7.21 min
MS: m/z=232 (M)+

Step 3

To a solution of 3-(2-fluoro-4-trifluoromethyl-phenyl)-2,5-dihydro-furan (obtained as described in Step 2; 2.0 g 77% content, 6.63 mmol) in 50 mL of dichloromethane, stirred at 0° C., 3-chloroperoxybenzoic acid (2.63 g, 15.26 mmol) was added portionwise. The reaction mixture was allowed to reach room temperature and stirred overnight. The reaction mixture was cooled to 0° C. and the precipitate formed was filtered off. The organic solution was washed twice with an aqueous saturated solution of potassium carbonate, dried over sodium sulfate and concentrated under vacuum. The crude obtained was purified by flash chromatography (eluent: cyclohexane/AcOEt; gradient from 50% to 100% of AcOEt) to obtain 1.2 g (98% content) of 1-(2-fluoro-4-trifluoromethyl-phenyl)-3,6-dioxa-bicyclo[3.1.0]hexane.

$^1$H NMR (300 MHz, DMSO-$d_6$): δ ppm 3.91-3.95 (m, 2H), 4.06-4.19 (m, 3H) 7.37 (dd, J=10.2, 1.3 Hz, 1H), δ 7.47 (dd, J=8.4, 1.1 Hz, 1H), 7.59 (m, 1H)

Step 4

To a solution of 1-(2-fluoro-4-trifluoromethyl-phenyl)-3,6-dioxa-bicyclo[3.1.0]hexane (obtained as described in Step 3; 1.20 g, 98% content, 4.74 mmol) in 20 mL of acetonitrile, stirred under nitrogen atmosphere at −40° C., trifluoromethane sulfonic acid (0.84 mL, 9.48 mmol) was added dropwise. The reaction mixture was allowed to reach room temperature and stirred for 2.5 hrs. 20 mL of water were added, the reaction mixture was warmed to 100° C. and acetonitrile was distilled out. The reaction mixture was stirred at 100° C. for 20 hrs, then cooled to room temperature and stirred overnight. The reaction mixture was diluted with dichloromethane and phases were separated. The aqueous phase was treated with a 4M solution of NaOH until basic pH and extracted with dichloromethane. The organic phase was dried over sodium sulfate and concentrated under vacuum to give 200 mg of 4-amino-4-(2-fluoro-4-trifluoromethyl-phenyl)-tetrahydro-furan-3-ol, as racemic mixture (TRANS/CIS diastereoisomeric ratio 88/12, determined by NMR).

The crude was used in the next step without any further purification.

LC-MS (METHOD 1): $R_t$=2.52-3.04 min
MS (ESI pos): m/z=266 (M+H)$^+$
1H NMR (400 MHz, DMSO-$d_6$) δ 7.59-7.54 (m, 1H), 7.52-7.45 (m, 2H), 5.08 (d, J=4.8 Hz, 1H), 4.29 (q, J=3.8 Hz, 1H), 4.25 (dd, J=8.8, 3.8 Hz, 1H), 4.14 (d, J=7.6 Hz, 1H), 3.95 (dd, J=8.0, 2.2 Hz, 1H), 3.65 (d, J=8.8 Hz, 1H), 2.06 (s, 2H).
NOE: 2.06 (NH2): 3.95; 4.29; 4.25, 5.08 (OH): 4.14; 3.65

Intermediate 38

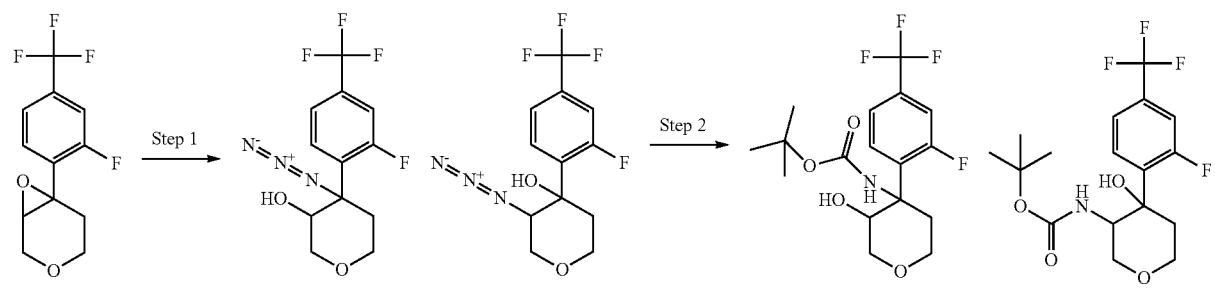

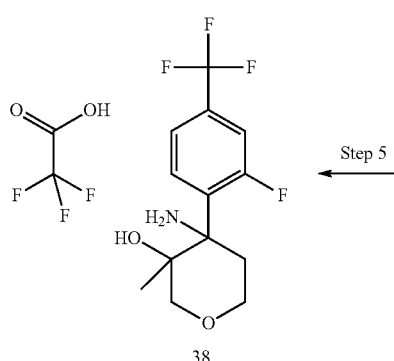
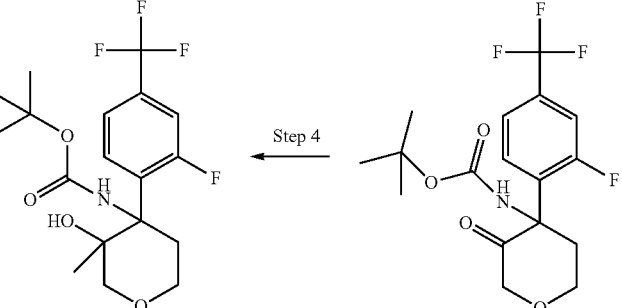

Step 1

6-(2-Fluoro-4-trifluoromethyl-phenyl)-3,7-dioxa-bicyclo[4.1.0]heptane (obtained as described in Step 2 in the preparation of Intermediate 34; 4.20 g, 16.02 mmol), sodium azide (2.08 g, 32.04 mmol) and ammonium chloride (1.72 g, 32.04 mmol) were suspended in 50 mL of methanol and 10 mL of water. The reaction mixture was stirred at reflux for 18 hrs. Solvents were removed, the crude was suspended in water and extracted twice with ethyl acetate. The organic layer was dried over sodium sulfate and concentrated under vacuum to give 4.70 g of the final compound as a mixture of the desired regioisomer 4-Azido-4-(2-fluoro-4-trifluoromethyl-phenyl)-tetrahydro-pyran-3-ol and the undesired regioisomer 3-azido-4-(2-fluoro-4-trifluoromethyl-phenyl)-tetrahydro-pyran-4-ol in a regioisomeric ratio of 76/24 determined by NMR. The regioisomeric mixture was used in the next step without separation.

GC-MS (METHOD 9): $R_t$=9.57 min
MS: m/z=248 (M)+
1H NMR (500 MHz, DMSO-$d_6$) δ 7.77-7.74 (m, 1H), 7.72 (d, J=7.9 Hz, 1H), 7.67-7.64 (m, 1H), 5.37 (d, J=6.0 Hz, 1H), 3.93-3.89 (m, 1H), 3.85-3.80 (m, 1H), 3.78 (dd, J=12.3, 1.5 Hz, 1H), 3.74-3.66 (m, 2H), 2.65 (ddd, J=13.8, 11.9, 4.8 Hz, 1H), 2.02-1.95 (m, 1H).

Step 2

A mixture of 4-Azido-4-(2-fluoro-4-trifluoromethyl-phenyl)-tetrahydro-pyran-3-ol and 3-azido-4-(2-fluoro-4-trifluoromethyl-phenyl)-tetrahydro-pyran-4-ol (obtained as described in Step 1, 2.0 g, 6.55 mmol), Pd/C (300 mg, 2.82 mmol) and di-tert-butyldicarbonate (1.86 g, 8.52 mmol) were suspended in 150 mL of ethanol. The reaction mixture was stirred at room temperature under hydrogen atmosphere (2.5 bar) for 1 hr. The reaction mixture was filtered on a celite pad and the organic solution was concentrated under vacuum. The crude obtained was purified by flash chromatography (eluent: cyclohexane/AcOEt; gradient from 10% to 100% of AcOEt) to obtain 1.75 g of the title compound (yellow solid) as a mixture of the desired regioisomer [4-(2-fluoro-4-trifluoromethyl-phenyl)-3-hydroxy-tetrahydro-pyran-4-yl]-carbamic acid tert-butyl ester and the undesired regioisomer [4-(2-Fluoro-4-trifluoromethyl-phenyl)-4-hydroxy-tetrahydro-pyran-3-yl]-carbamic acid tert-butyl ester in a regioisomeric ratio of 85/15 determined by NMR. The regioisomeric mixture was used in the next step without separation.

GC-MS (METHOD 9): $R_t$=10.92-10.99 min
MS: m/z=323 (M)+

Step 3

A mixture of [4-(2-Fluoro-4-trifluoromethyl-phenyl)-3-hydroxy-tetrahydro-pyran-4-yl]-carbamic acid tert-butyl ester and 4-(2-Fluoro-4-trifluoromethyl-phenyl)-4-hydroxy-tetrahydro-pyran-3-yl]-carbamic acid tert-butyl ester (obtained as described in Step 2, 3.7 g, 7.30 mmol) was dissolved in 20 mL of dichlorometane, Dess-Martin periodinane (2.18 g, 9.5 mmol) was added portionwise and the reaction mixture was stirred at room temperature for 2 hrs. The reaction mixture was diluted with dichloromethane, washed with aqueous bicarbonate saturated solution, washed with aqueous sodium bisulfite saturated solution, the organic layer was separated, dried over sodium sulfate and concentrated under vacuum. The crude obtained was purified by flash chromatography (eluent: dichloromethane/AcOEt; gradient from 0% to 70% of AcOEt) to give 2.4 g of the desired compound.

LC-MS (METHOD 1): $R_t$=4.23-4.83 min
MS (ESI pos): m/z=278 (fragment) (M+H)$^+$

Step 4

[4-(2-Fluoro-4-trifluoromethyl-phenyl)-3-oxo-tetrahydro-pyran-4-yl]-carbamic acid tert-butyl ester (obtained as described in Step 3; 340 mg, 0.9 mmol) was suspended in 10 mL of dry THF. The reaction mixture was stirred at −20° C. and 0.29 mL of a 3.4M solution of methylmagnesium bromide in methyl-tetrahydrofurane was added dropwise. The reaction mixture was stirred at −20° C. for 1 hr, then quenched with aqueous saturated ammonium chloride solution. Organic layer was separated, dried over sodium sulfate and concentrated under vacuum. The crude obtained was purified by flash chromatography (eluent: dichloromethane/AcOEt; gradient from 0% to 30% of AcOEt) to give 200 mg of the title compound, 4-(2-fluoro-4-trifluoromethyl-phenyl)-3-hydroxy-3-methyl-tetrahydro-pyran-4-yl]-carbamic acid tert-butyl ester, as racemic mixture (TRANS/CIS diastereoisomeric ratio 82/12, determined by NMR).

GC-MS (METHOD 9): $R_t$=11.01 min
MS: m/z=292 (fragment) (M)+
1H NMR (500 MHz, DMSO-$d_6$) δ 7.58-7.53 (m, 1H), 7.52-7.48 (m, 1H), 7.45 (d, J=12.8 Hz, 1H), 6.92 (s, 1H), 4.78 (s, 1H), 3.88 (d, J=12.2 Hz, 1H), 3.70 (t, J=6.7 Hz, 1H), 3.60 (q, J=12.8, 12.2 Hz, 1H), 3.28-3.26 (d, J=12.2 Hz, 1H), 2.88 (t, J=11.4 Hz, 1H), 1.33 (s, 9H), 0.9 (s, 3H).
NOE: 6.92 (NH): 0.90; 3.88, 4.78 (OH): 2.88; 3.27

Step 5

4-(2-Fluoro-4-trifluoromethyl-phenyl)-3-hydroxy-3-methyl-tetrahydro-pyran-4-yl]-carbamic acid tert-butyl ester (obtained as described in Step 4, as preferred diastereoisomer; 200 mg, 0.51 mmol) was dissolved in 5 mL of dichloromethane. Trifluoroacetic acid (0.39 mL, 5.1 mmol) was added, the reaction mixture was stirred at room temperature for 1 hr and then concentrated under vacuum. The crude obtained was stripped twice with ethyl ether to give 198 mg of the title compound, 4-amino-4-(2-fluoro-4-trifluoromethyl-phenyl)-3-methyl-tetrahydro-pyran-3-ol trifluoroacetate salt as racemic mixture (TRANS/CIS diastereoisomeric ratio 85/15, determined by NMR).

LC-MS (METHOD 1): $R_t$=3.35 min
MS (ESI pos): m/z=294 (M+H)$^+$
1H NMR (500 MHz, DMSO-d$_6$) δ 8.61 (s, 3H), 7.96 (t, J=8.2 Hz, 1H), 7.81 (dd, J=13.3, 2.0 Hz, 1H), 7.70-7.66 (m, 1H), 5.40 (s, 1H), 3.98 (ddd, J=13.3, 10.7, 2.8 Hz, 1H), 3.92-3.85 (m, 1H), 3.62 (d, J=12.6 Hz, 1H), 3.40-3.38 (d, J=12.6 Hz, 1H), 2.99 (ddd, J=14.4, 10.7, 5.2 Hz, 1H), 1.79 (dt, J=14.4, 3.0 Hz, 1H), 1.11 (d, J=1.8 Hz, 3H).

Intermediate 39

Step 2

Step 2 was performed in analogy to Step 2 in the preparation of Intermediate 35, starting from 2-(3,6-Dihydro-2H-pyran-4-yl)-3-fluoromethyl-pyridine (5.7 g, 23.06 mmol) to obtain 2-(3,7-dioxa-bicyclo[4.1.0]hept-6-yl)-3-fluoro-5-trifluoromethyl-pyridine (3.25 g).

LC-MS (METHOD 2): $R_t$=0.95 min
MS (ESI pos): m/z=264 (M+H)$^+$

Step 3

Step 3 was performed in analogy to Step 1 in the preparation of Intermediate 38, starting from 2-(3,7-Dioxa-bicyclo[4.1.0]hept-6-yl)-3-fluoro-5-trifluoromethyl-pyridine (250 mg, 0.95 mmol) to obtain after purification by flash chromatography (eluent: cyclohexane/EtOAc; gradient from 0% to 30% of EtOAc), 4-azido-4-(3-fluoro-5-trifluoromethyl-pyridin-2-yl)-tetrahydro-pyran-3-ol (160 mg) as major regioisomer LC-MS (METHOD 2): $R_t$=1.05 min
MS (ESI pos): m/z=307 (M+H)$^+$
1H NMR (500 MHz, DMSO-d$_6$) δ 8.90 (dq, J=2.0, 0.9 Hz, 1H), 8.39 (ddd, J=11.5, 1.9, 0.7 Hz, 1H), 5.42 (s, 1H),

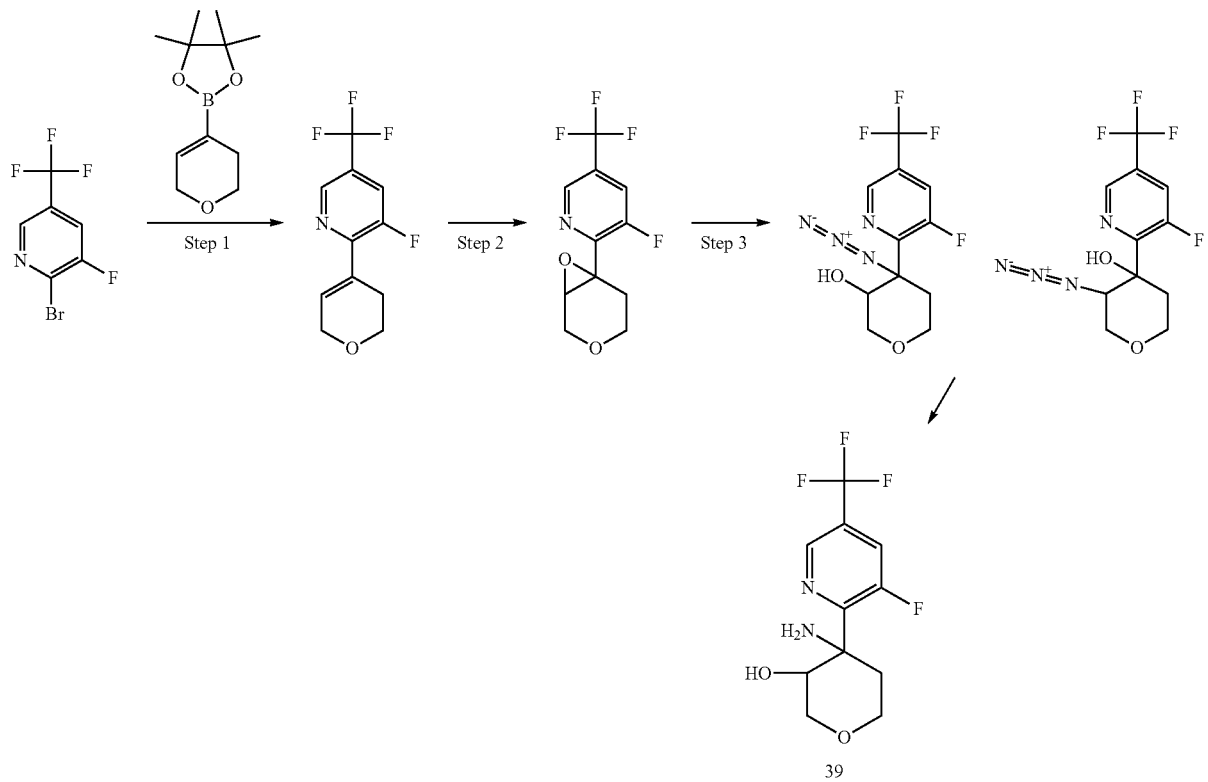

4.01 (s, 1H), 3.93-3.86 (m, 1H), 3.78-3.64 (m, 3H), 2.73 (ddd, J=14.6, 12.6, 4.9 Hz, 1H), 2.02 (dq, J=14.7, 2.0 Hz, 1H).

The minor regioisomer, 3-Azido-4-(3-fluoro-5-trifluoromethyl-pyridin-2-yl)-tetrahydro-pyran-4-ol, was also isolated (40 mg).

LC-MS (METHOD 2): $R_t$=1.04 min
MS (ESI pos): m/z=307 (M+H)$^+$

Step 1

Step 1 was performed in analogy to Step 1 in the preparation of Intermediate 35, starting from 2-bromo-3-fluoro-5-(trifluoromethyl)pyridine (5 g, 20.49 mmol) to obtain 2-(3,6-dihydro-2H-pyran-4-yl)-3-fluoromethyl-pyridine (5.7 g).

LC-MS (METHOD 2): $R_t$=1.17 min
MS (ESI pos): m/z=248 (M+H)$^+$

Step 4

To a solution of 4-azido-4-(3-fluoro-5-trifluoromethyl-pyridin-2-yl)-tetrahydro-pyran-3-ol (160 mg, 0.52 mmol) in 5 mL of methanol stirred under nitrogen atmosphere, ammonium formate (165 mg, 2.61 mmol) and zinc (51.2 mg, 0.78 mmol) were added. The reaction mixture was stirred at room temperature overnight and concentrated. A saturated ammonium chloride water solution was added and the reaction mixture was extracted with dichloromethane. The organic phase was separated, washed with brine, dried over sodium sulfate and concentrated under vacuum to give 115 mg of 4-Amino-4-(3-fluoro-5-trifluoromethyl-pyridin-2-yl)-tetrahydro-pyran-3-ol, as TRANS-racemic mixture.

LC-MS (METHOD 5): $R_t$=0.71 min
MS (ESI pos): m/z=281 (M+H)$^+$
1H NMR (500 MHz, DMSO-d6) δ 8.75 (dq, J=2.0, 1.0 Hz, 1H), 8.18-8.12 (m, 1H), 4.80 (d, J=5.6 Hz, 1H), 4.01 (dd, J=11.7, 1.5 Hz, 1H), 3.89-3.83 (m, 1H), 3.78 (dt, J=5.5, 1.9 Hz, 1H), 3.74-3.66 (m, 1H), 3.55 (dd, J=11.7, 1.7 Hz, 1H), 2.71-2.61 (m, 1H), 2.09 (s, 2H), 1.65-1.58 (m, 1H).
NOE: 2.09 (NH2): 3.55; 3.70; 3.78 4.80 (OH): 1.61; 3.78

The following intermediate was prepared in analogy to Intermediate 39, starting from 2-Bromo-5-trifluoromethyl-pyridine

| Starting | | Amino-alcohol intermediate | MS m/z | $R_t$ (min) | Method |
|---|---|---|---|---|---|
| 2-Bromo-5-trifluoromethyl pyridine | 40 | ![structure] | 263 | 0.68 | METHOD 2 |

1H NMR (500 MHz, DMSO-d6) δ 8.89 (dq, J=2.6, 0.9 Hz, 1H), 8.13 (ddd, J=8.4, 2.5, 0.8 Hz, 1H), 7.69 (dt, J=8.4, 0.8 Hz, 1H), 4.69 (d, J=5.6 Hz, 1H), 4.05 (dd, J=11.4, 1.7 Hz, 1H), 3.84 (td, J=11.3, 2.4 Hz, 1H), 3.72 (ddd, J=10.9, 4.7, 2.7 Hz, 1H), 3.60 (ddd, J=5.7, 2.8, 1.4 Hz, 1H), 3.54 (dd, J=11.5, 2.8 Hz, 1H), 2.56-2.51 (m, 1H), 2.02 (s, 2H), 1.62-1.52 (m, 1H).
NOE: 2.09 (NH2): 3.55; 3.70; 3.78 4.80 (OH): 1.61; 3.78

Intermediate 41

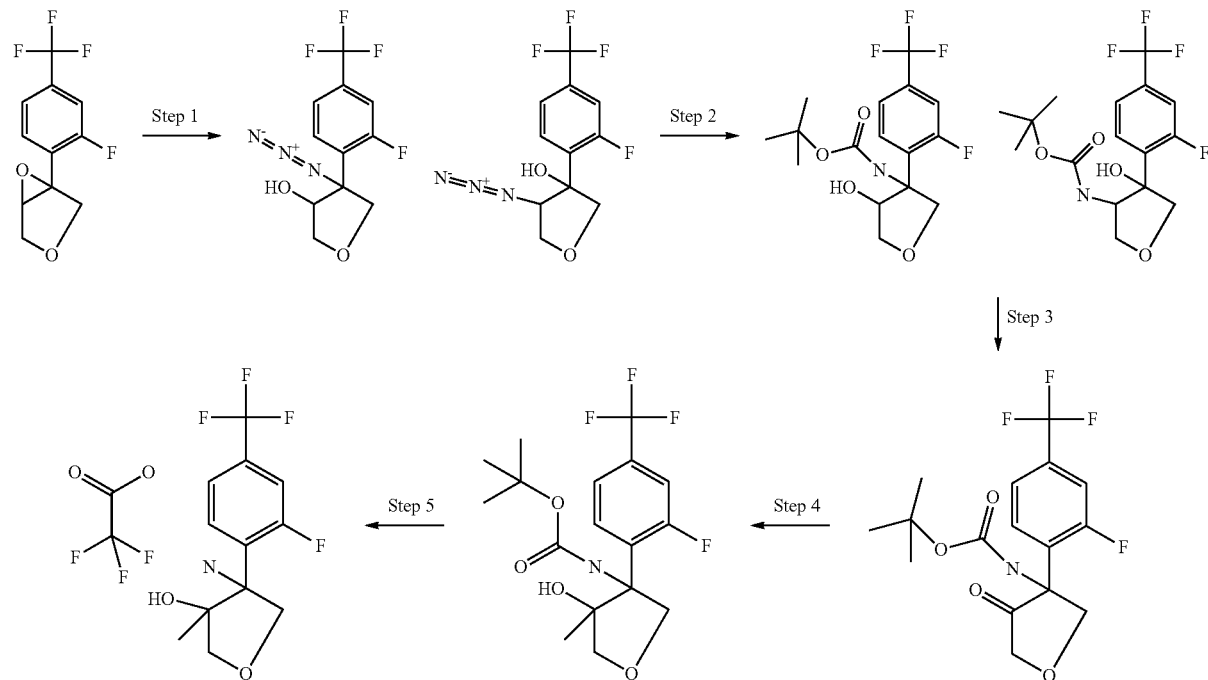

41

Step 1

Step 1 was performed in analogy to Step 1 in the preparation of Intermediate 38, starting from 1-(2-fluoro-4-trifluoromethyl-phenyl)-3,6-dioxa-bicyclo[3.1.0]hexane (750, 3.02 mmol, prepared as described in Step 3 in the preparation of Intermediate 37) to obtain 4-azido-4-(2-fluoro-4-trifluoromethyl-phenyl)-tetrahydro-furan-3-ol as major regioisomer and 4-Azido-3-(2-fluoro-4-trifluoromethyl-phenyl)-tetrahydro-furan-3-ol as minor regioisomer. (900 mg, regioisomer ratio 82/18 determined by NMR) GC-MS (METHOD 9): $R_t$=9.22 min MS: m/z=190 (fragment) (M)+

1H NMR (500 MHz, DMSO-$d_6$) δ 7.82-7.77 (m, 1H), 7.66-7.60 (m, 2H), 5.72 (d, J=5.4 Hz, 1H), 4.59-4.55 (m, 1H), 4.39 (dd, J=9.7, 1.8 Hz, 1H), 4.23 (d, J=9.7 Hz, 1H), 4.18 (dd, J=9.6, 4.1 Hz, 1H), 3.79-3.75 (d, 1H).

Step 2

Step 2 was performed in analogy to Step 1 in the preparation of Intermediate 38, starting from the regioisomeric mixture, to obtain [3-(2-fluoro-4-trifluoromethyl-phenyl)-4-hydroxy-tetrahydro-furan-3-yl]-carbamic acid tert-butyl ester as preferred regioisomer and 4-(2-Fluoro-4-trifluoromethyl-phenyl)-4-hydroxy-tetrahydro-furan-3-yl]-carbamic acid tert-butyl ester (670 mg) (regioisomer ratio 80/20 determined by NMR).

GC-MS (METHOD 9): $R_t$=10.67 min

MS: m/z=265 (fragment) (M)+

Step 3

Step 3 was performed in analogy to Step 3 in the preparation of Intermediate 38, starting from the regioisomeric mixture of [3-(2-fluoro-4-trifluoromethyl-phenyl)-4-hydroxy-tetrahydro-furan-3-yl]-carbamic acid tert-butyl ester and 4-(2-Fluoro-4-trifluoromethyl-phenyl)-4-hydroxy-tetrahydro-furan-3-yl]-carbamic acid tert-butyl ester (670 mg, 1.47 mmol), to obtain [3-(2-fluoro-4-trifluoromethyl-phenyl)-4-oxo-tetrahydro-furan-3-yl]-carbamic acid tert-butyl ester (455 mg).

GC-MS (METHOD 9): $R_t$=10.15 min

MS: m/z=249 (fragment) (M)+

Step 4

Step 4 was performed in analogy to Step 4 in the preparation of Intermediate 38, starting from [3-(2-fluoro-4-trifluoromethyl-phenyl)-4-oxo-tetrahydro-furan-3-yl]-carbamic acid tert-butyl ester (455 mg, 1.23) to obtain [3-(2-fluoro-4-trifluoromethyl-phenyl)-4-hydroxy-4-methyl-tetrahydro-furan-3-yl]-carbamic acid tert-butyl ester as-racemic mixture (TRANS/CIS diastereoisomeric ratio 91/9, determined by NMR). (365 mg).

LC-MS (METHOD 10): $R_t$=3.46-3.62 min

MS (ESI pos): m/z=280 (fragment) (M+H)+

1H NMR (500 MHz, DMSO-d6) δ 7.64 (t, J=7.9 Hz, 1H), 7.51 (d, J=9.5 Hz, 2H), 7.04 (s, 1H), 4.98 (s, 1H), 4.72-4.65 (m, 1H), 4.13 (d, J=8.4 Hz, 1H), 3.94 (d, J=8.8 Hz, 1H), 3.60 (d, J=8.8 Hz, 1H), 1.31 (s, 12H).

NOE: 7.04 (NH): 3.94; 4.13; 1.31 4.98 (OH): 1.31; 4,68 1.31 (Me): 7.04; 4.13; 4.98

Step 5

Step 5 was performed in analogy to Step 5 in the preparation of Intermediate 38, starting from [3-(2-fluoro-4-trifluoromethyl-phenyl)-4-hydroxy-4-methyl-tetrahydro-furan-3-yl]-carbamic acid tert-butyl ester (365 mg, 1.0 mmol) to obtain 4-amino-4-(2-fluoro-4-trifluoromethyl-phenyl)-3-methyl-tetrahydro-furan-3-ol trifluoroacetate, as racemic mixture (TRANS/CIS diastereoisomeric ratio 90/10, determined by NMR). (378 mg)

LC-MS (METHOD 1): $R_t$=2.91-3.19 min

MS (ESI pos): m/z=280 (M+H)+

1H NMR (500 MHz, DMSO-d6) δ 8.67 (s, 3H), 7.88-7.79 (m, 2H), 7.70 (dd, J=8.5, 1.9 Hz, 1H), 5.62 (s, 1H), 4.62 (dd, J=10.0, 1.1 Hz, 1H), 4.19 (dd, J=10.0, 1.5 Hz, 1H), 3.98 (d, J=9.6 Hz, 1H), 3.80 (d, J=9.6 Hz, 1H), 1.48 (d, J=1.3 Hz, 3H).

Intermediate 42

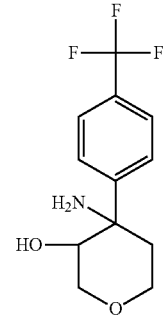 [SMILES: NC1(c2ccc(C(F)(F)F)cc2)CCOCC1O]

Intermediate 42 was prepared in analogy to Intermediate 35, starting from 4-iodobenzotrifluoride (3 g, 10.7 mmol) to obtain, after chromatographic purification in the third step (eluent: cyclohexane/EtOAc; gradient from 0% to 100% of EtOAc), 105 mg the title compound, as racemic mixture (TRANS/CIS diastereoisomeric ratio 93/7, determined by NMR).

LC-MS (METHOD 5): $R_t$=0.77 min

MS (ESI pos): m/z=262 (M+H)+

1H NMR (500 MHz, DMSO-d6) δ 7.71-7.67 (m, 2H), 7.65-7.61 (m, 2H), 4.58 (d, J=5.9 Hz, 1H), 4.05 (dd, J=11.5, 1.5 Hz, 1H), 3.92-3.86 (m, 1H), 3.67 (ddd, J=11.1, 4.9, 2.3 Hz, 1H), 3.57-3.52 (m, 1H), 3.48 (dq, J=5.7, 1.5 Hz, 1H), 2.49-2.41 (m, 1H), 1.97 (s, 2H), 1.49-1.42 (m, 1H).

NOE 1.97 (NH2): 3.48; 4.05; 1.47 4.58 (OH): 2.46; 3.55 3.48 (CH): 1.97; 3.89

Intermediate 43

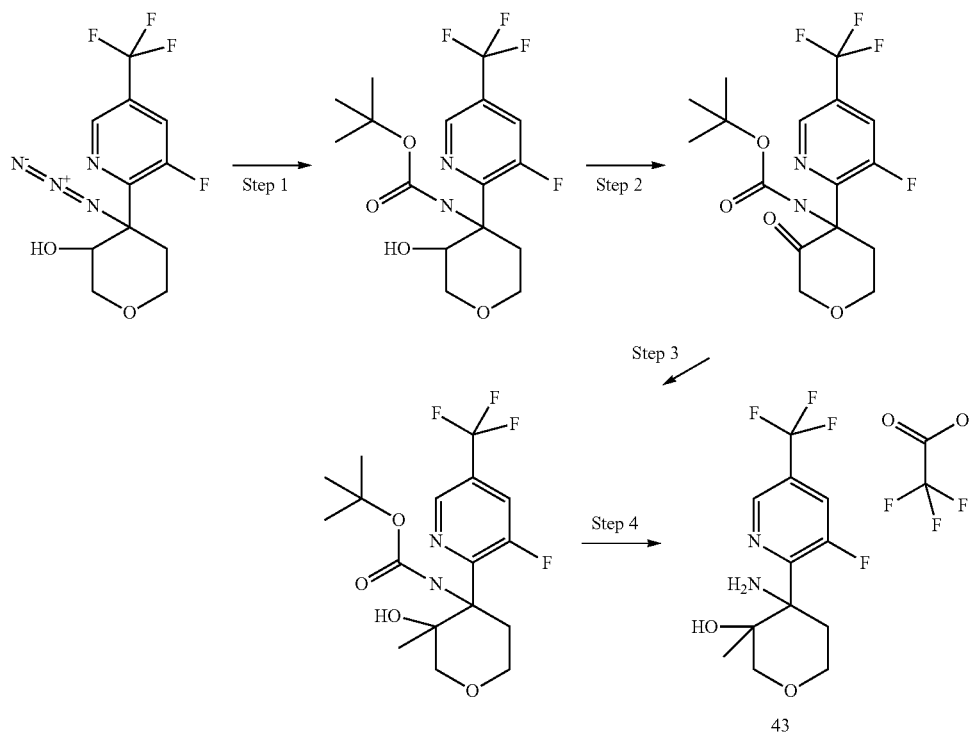

Step 1

Step 1 was performed in analogy to Step 2 in the preparation of Intermediate 38, starting from 4-Azido-4-(3-fluoro-5-trifluoromethyl-pyridin-2-yl)-tetrahydro-pyran-3-ol (1.7 g, 4.77 mmol) to obtain after filtration on silica, 1.3 g of the title compound as TRANS-racemic mixture LC-MS (METHOD 1): $R_t$=3.93 min
MS (APCI): m/z=381 (M+H)$^+$

Step 2

To a solution of oxalylchloride (0.25 mL, 2.6 mmol) in dry DCM (20 mL) at −55° C., DMSO (0.37 mL, 0.51 mmol) was added dropwise. After 20 min, a solution of (3-fluoro-5-trifluoromethyl-pyridin-2-yl)-3-hydroxy-tetrahydro-pyran-4-yl]-carbamic acid tert-butyl ester (1.0 g, 2.37 mmol) dissolved in 3 mL of dry DCM was added dropwise. Mixture is stirred for 1 h at −70° C., then TEA was added dropwise, stirred for 1.30 hrs at −40° C. and then allowed to reach room temperature. Mixture was stirred at room temperature for 48 hrs. Solvent was evaporated, residue diluted with 50 ml of ethyl acetate and washed with 3×10 ml of water. Organic phase was separated, dried over sodium sulfate to obtain 0.92 g of the desired compound used in the next step without further purification.

LC-MS (METHOD 1): $R_t$=3.79 min
MS (APCI): m/z=475 (M+H)$^+$

Step 3

Step 3 was performed in analogy to Step 4 in the preparation of Intermediate 38, starting from 4-(3-fluoro-5-trifluoromethyl-pyridin-2-yl)-3-oxo-tetrahydro-pyran-4-yl]-carbamic acid tert-butyl ester (0.92 g, 2.41 mmol) to obtain after chromatographic purification (eluent: cyclohexane/EtOAc; gradient from 100% to 40% of EtOAc), 0.190 g of CIS stereoisomer and 0.35 g of TRANS stereoisomer, both as racemic mixture.

LC-MS (METHOD 9): $R_t$=10.49 min (CIS stereoisomer)
MS (ESI): m/z=394 (M+H)$^+$
1H NMR (500 MHz, DMSO-$d_6$) δ ppm 0.88 (s, 3H) 1.22-1.38 (m, 9H) 2.26-2.42 (m, 1H) 2.80 (td, J=13.54, 4.65 Hz, 1H) 3.25-3.29 (m, 1H) 3.54-3.63 (m, 2H) 3.78 (br dd, J=11.37, 3.42 Hz, 1H) 5.31 (s, 1H) 6.40 (br s, 1H) 8.18 (br d, J=11.61 Hz, 1H) 8.81-8.86 (m, 1H)
NOE: 6.40 (NH): 5.31 5.31 (OH): 6.40
LC-MS (METHOD 9): $R_t$=10.76 min (TRANS stereoisomer)
MS (ESI): m/z=394 (M+H)$^+$
1H NMR (500 MHz, DMSO-$d_6$) δ ppm 1.03 (d, J=2.93 Hz, 3H) 1.10-1.44 (m, 9H) 1.96-2.03 (m, 1H) 3.06-3.18 (m, 1H) 3.24 (d, J=11.98 Hz, 1H) 3.54-3.69 (m, 1H) 3.72-3.86 (m, 2H) 4.71 (s, 1H) 7.01 (br s, 1H) 8.09 (br d, J=11.74 Hz, 1H) 8.79 (s, 1H)
NOE: 7.01 (NH): 1.02; 3.62; 3.77 4.71 (OH): 3.12; 3.24

Step 4

Step 4 was performed in analogy to Step 5 in the preparation of Intermediate 38, starting from TRANS [(R)-4-(3-Fluoro-5-trifluoromethyl-pyridin-2-yl)-3-hydroxy-3-methyl-tetrahydro-pyran-4-yl]-carbamic acid tert-butyl ester (0.350 g, 0.89 mmol) to obtain 0.25 g of desired intermediate 42, 4-Amino-4-(3-fluoro-5-trifluoro methyl-pyridin-2-yl)-3-methyl-tetrahydro-pyran-3-ol, as trifloroacetate salt.

LC-MS (METHOD 1): $R_t$=2.90 min
MS (APCI): m/z=295 (M+H)$^+$

1H NMR (500 MHz, DMSO-d$_6$) δ ppm 1.00 (s, 3H) 1.87-1.93 (m, 1H) 3.14 (ddd, J=14.49, 9.72, 4.65 Hz, 1H) 3.39-3.43 (m, 1H) 3.66-3.69 (m, 1H) 3.81-3.88 (m, 1H) 4.04 (dt, J=11.86, 4.34 Hz, 1H) 5.48 (br s, 1H) 8.43-8.48 (m, 1H) 8.72 (br s, 3H) 8.94 (s, 1H)

NOE: 8.72 (NH3+): 1.00; 1.90; 3.68; 3.84 1.0 (Me): 8.72; 1.89; 3.66

Intermediate 44

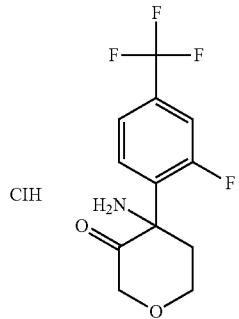 [SMILES: "CIH" ; NC1(c2ccc(C(F)(F)F)cc2F)CCOCC1=O]

[4-(2-Fluoro-4-trifluoromethyl-phenyl)-3-oxo-tetrahydro-pyran-4-yl]-carbamic acid tert-butyl ester (obtained from Step 3 in the preparation of Intermediate 38; 90 mg, 0.23 mmol) was dissolved in 1 mL of 1.4-dioxane. 1.67 mL of a 1.4M solution of hydrogen chloride in 1.4-dioxane was added, the reaction mixture was stirred at room temperature for 1 hr and then concentrated under vacuum. The crude obtained was stripped twice with ethyl ether to give 70 mg of the title compound, used in the next step without further purification.

LC-MS (METHOD 1): R$_t$=3.70 min
MS (ESI pos): m/z=278 (M+H)$^+$

EXAMPLE COMPOUNDS

Example 1

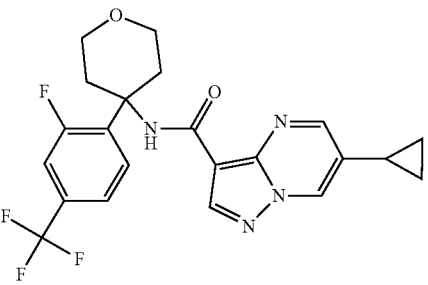 [SMILES: O=C(NC1(c2ccc(C(F)(F)F)cc2F)CCOCC1)c1cnn2cc(C3CC3)cnc12]

To a suspension of Intermediate 5 (40.68 mg, 0.20 mmol) in 1.0 mL of dry DMF, HATU (82.47 mg, 1.3 mmol) and DIPEA (0.11 mL 0.67 mmol) were added and the reaction mixture was stirred at room temperature. A solution of Intermediate 13 (50 mg, 0.17 mmol) in 1.0 mL of dry DMF was added, and the reaction mixture was stirred at room temperature overnight. The reaction mixture was treated with basic alumina and concentrated under vacuum. The crude obtained was purified by flash chromatography (eluent: water/acetonitrile; gradient from 10% to 100% of acetonitrile) to give 62 mg of the desired compound.

LC-MS (METHOD 1): R$_t$=4.78 min
MS (ESI pos): m/z=463 (M+H)$^+$

The following Examples were prepared in analogy to Example 1 and purified applying the most suitable purification technique, starting from the corresponding Acid and the corresponding Amine Intermediates:

| Starting Acid | Starting Amine | Ex. | Structure | MS m/z [M + H]$^+$ | R$_t$ (min) | Method |
|---|---|---|---|---|---|---|
| 2 | 13 | 2 | 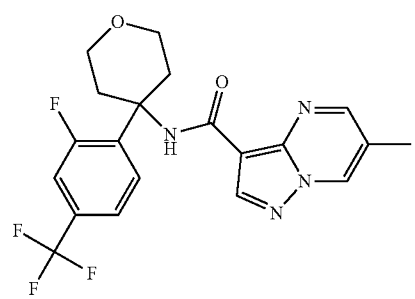 [SMILES: Cc1cnc2c(C(=O)NC3(c4ccc(C(F)(F)F)cc4F)CCOCC3)cnn2c1] | 423 | 4.53 | METHOD 1 |
| 6 | 13 | 3 | 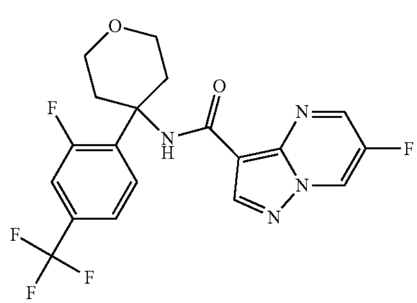 [SMILES: O=C(NC1(c2ccc(C(F)(F)F)cc2F)CCOCC1)c1cnn2cc(F)cnc12] | 427 | 3.50 | METHOD 10 |

-continued

| Starting Acid | Starting Amine | Ex. | Structure | MS m/z [M + H]+ | R$_t$ (min) | Method |
|---|---|---|---|---|---|---|
| 8 | 14 | 4 | 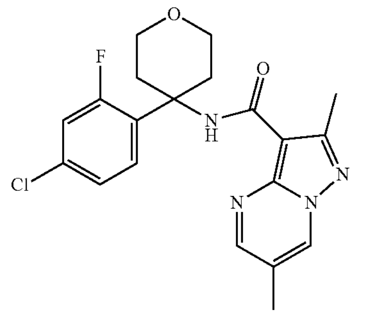 [SMILES: Cc1cnc2c(C(=O)NC3(c4ccc(Cl)cc4F)CCOCC3)c(C)nn2c1] | 403 | 0.90 | METHOD 6 |
| 2 | 14 | 5 | 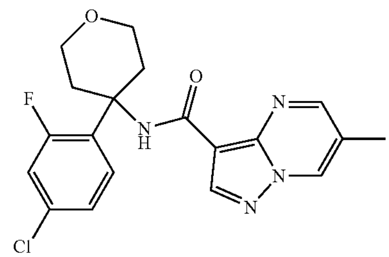 [SMILES: Cc1cnc2c(C(=O)NC3(c4ccc(Cl)cc4F)CCOCC3)cnn2c1] | 389 | 4.28 | METHOD 1 |
| 5 | 25 | 6 | | 415 | 4.67 | METHOD 1 |
| 5 | 14 | 7 | | 415 | 4.78 | METHOD 1 |
| 5 | 15 | 8 | | 431 | 4.98 | METHOD 1 |

-continued

| Starting Acid | Starting Amine | Ex. | Structure | MS m/z [M + H]+ | R$_t$ (min) | Method |
|---|---|---|---|---|---|---|
| 2 | 15 | 9 | | 405 | 4.40 | METHOD 1 |
| 5 | 16 | 10 | | 411 | 0.80 | METHOD 7 |
| 12 | 17 | 11 | 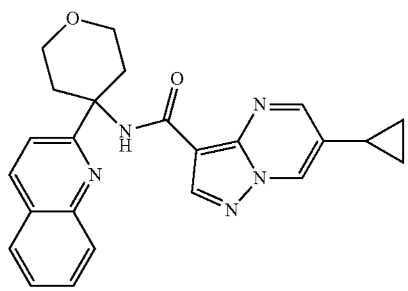 [SMILES: O=C(NC1(c2ccc3ccccc3n2)CCOCC1)c1cnn2cc(C3CC3)cnc12] | 428 | 3.21 | METHOD 10 |
| 2 | 17 | 12 | | 388 | 2.86 | METHOD 10 |
| 5 | 18 | 13 | | 441 | 0.87 | METHOD 8 |

-continued
| Starting Acid | Starting Amine | Ex. | Structure | MS m/z [M + H]+ | R_t (min) | Method |
|---|---|---|---|---|---|---|
| 5 | 19 | 14 | 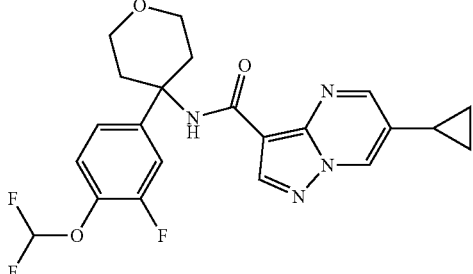 | 447 | 3.54 | METHOD 10 |
| 2 | 19 | 15 | 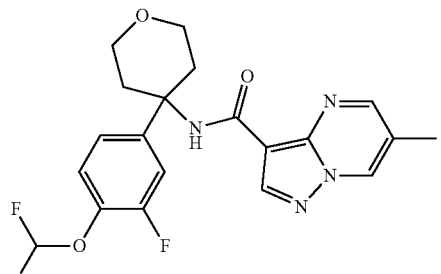 | 421 | 3.26 | METHOD 10 |
| 5 | 20 | 16 | 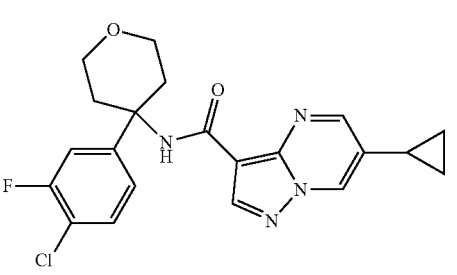 [SMILES: O=C(NC1(c2ccc(Cl)c(F)c2)CCOCC1)c1cnn2cc(C3CC3)cnc12] | 415 | 4.70 | METHDO 1 |
| 12 | 21 | 17 | 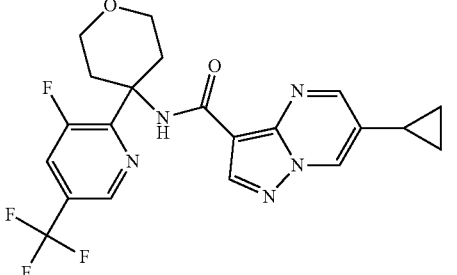 | 464 | 4.93 | METHOD 1 |
| 8 | 21 | 18 | 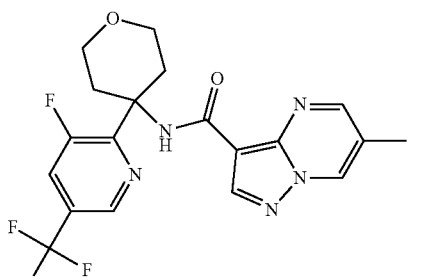 | 438 | 3.38 | METHOD 10 |

-continued

| Starting Acid | Starting Amine | Ex. | Structure | MS m/z [M + H]+ | R_t (min) | Method |
|---|---|---|---|---|---|---|
| 2 | 21 | 19 | 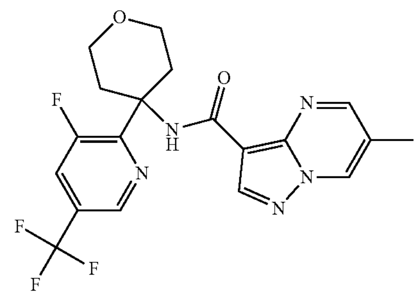 [SMILES: Cc1cnc2c(C(=O)NC3(c4ncc(C(F)(F)F)cc4F)CCOCC3)cnn2c1] | 424 | 3.27 | METHOD 10 |
| 5 | 21 | 20 | | 450 | 3.59 | METHOD 10 |
| 12 | 22 | 21 | 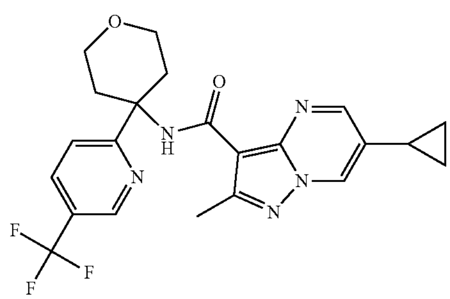 [SMILES: Cc1nn2cc(C3CC3)cnc2c1C(=O)NC1(c2ccc(C(F)(F)F)cn2)CCOCC1] | 446 | 4.52 | METHOD 1 |
| 8 | 22 | 22 | 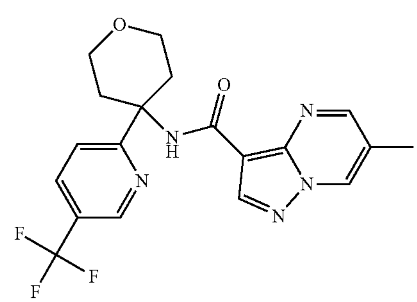 | 420 | 3.23 | METHOD 10 |
| 5 | 22 | 23 | | 432 | 3.45 | METHOD 10 |

-continued

| Starting Acid | Starting Amine | Ex. | Structure | MS m/z [M + H]+ | R_t (min) | Method |
|---|---|---|---|---|---|---|
| 2 | 22 | 24 | | 406 | 3.12 | METHDO 10 |
| 12 | 23 | 25 | 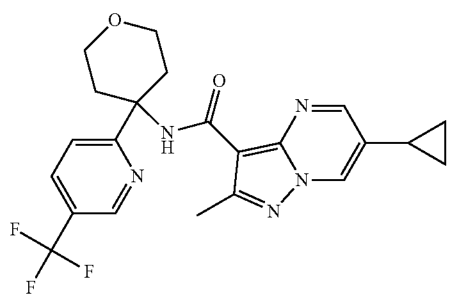 [SMILES: Cc1nn2cc(C3CC3)cnc2c1C(=O)NC1(c2ccc(C(F)(F)F)cn2)CCOCC1] | 446 | 4.75 | METHOD 1 |
| 8 | 23 | 26 | 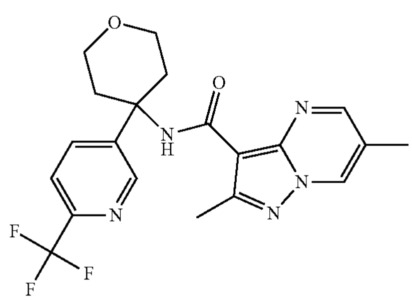 [SMILES: Cc1cnc2c(C(=O)NC3(c4ccc(C(F)(F)F)nc4)CCOCC3)c(C)nn2c1] | 420 | 3.13 | METHOD 10 |
| 5 | 23 | 27 | 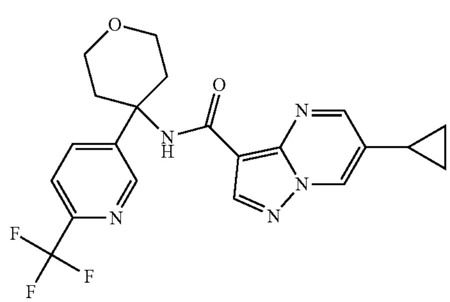 [SMILES: O=C(NC1(c2ccc(C(F)(F)F)nc2)CCOCC1)c1cnn2cc(C3CC3)cnc12] | 432 | 3.32 | METHOD 10 |
| 2 | 23 | 28 | | 406 | 3.01 | METHOD 10 |

-continued
| Starting Acid | Starting Amine | Ex. | Structure | MS m/z [M + H]+ | R_t (min) | Method |
|---|---|---|---|---|---|---|
| 12 | 24 | 29 | 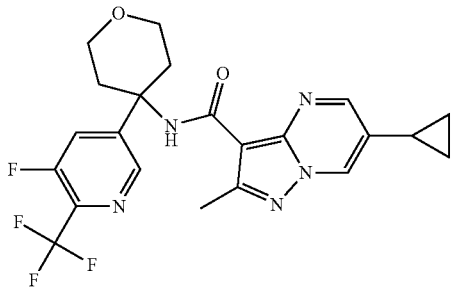 [SMILES: Cc1nn2cc(C3CC3)cnc2c1C(=O)NC1(c2cnc(C(F)(F)F)c(F)c2)CCOCC1] | 464 | 3.70 | METHOD 10 |
| 5 | 26 | 30 Racemic mixture | 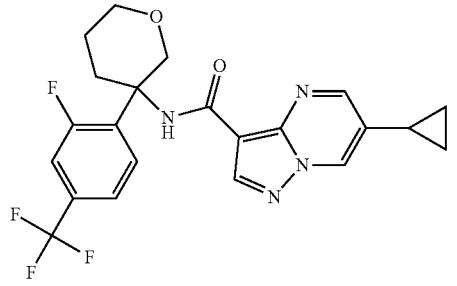 [SMILES: O=C(NC1(c2ccc(C(F)(F)F)cc2F)CCCOC1)c1cnn2cc(C3CC3)cnc12] | 449 | 3.87 | METHOD 10 |
| 2 | 26 | 31 Racemic mixture | 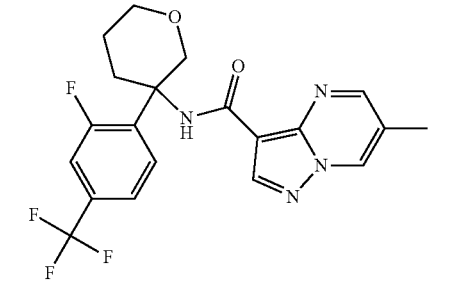 [SMILES: Cc1cnc2c(C(=O)NC3(c4ccc(C(F)(F)F)cc4F)CCCOC3)cnn2c1] | 423 | 3.60 | METHOD 10 |
| 5 | 27 | 32 Racemic mixture | 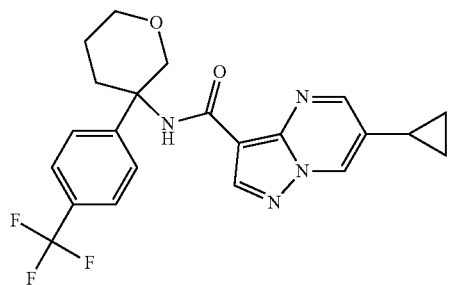 [SMILES: O=C(NC1(c2ccc(C(F)(F)F)cc2)CCCOC1)c1cnn2cc(C3CC3)cnc12] | [M + Na]+ 453 | 4.78 | METHOD 3 |
| 5 | 28 | 33 Racemic mixture | 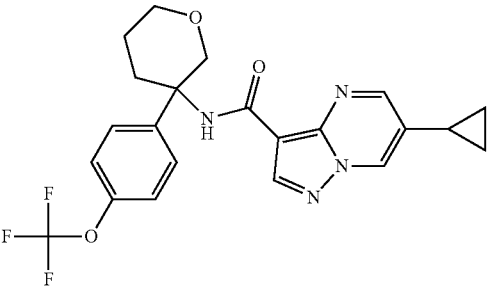 [SMILES: O=C(NC1(c2ccc(OC(F)(F)F)cc2)CCCOC1)c1cnn2cc(C3CC3)cnc12] | 447 | 4.83 | METHOD 3 |

-continued

| Starting Acid | Starting Amine | Ex. | Structure | MS m/z [M + H]+ | R$_t$ (min) | Method |
|---|---|---|---|---|---|---|
| 5 | 29 | 34 Racemic mixture | | 435 | 4.92 | METHOD 1 |
| 2 | 29 | 35 Racemic mixture | | 409 | 3.44 | METHOD 10 |
| 2 | 30 | 36 Racemic mixture | | 391 | 3.36 | METHOD 10 |
| 5 | 30 | 37 Racemic mixture | | 417 | 4.77 | METHOD 1 |
| 5 | 31 | 38 Racemic mixture | | 401 | 4.71 | METHOD 1 |
| 2 | 31 | 39 Racemic mixture | | [M + Na]+ 397 | 2.81 | METHOD 4 |

| Starting Acid | Starting Amine | Ex. | Structure | MS m/z [M + H]+ | R_t (min) | Method |
|---|---|---|---|---|---|---|
| 12 | 32 | 40 Racemic mixture | | 450 | 3.63 | METHOD 10 |
| 8 | 32 | 41 Racemic mixture | | 424 | 3.32 | METHOD 10 |
| 12 | 33 | 42 Racemic mixture | | 432 | 3.47 | METHOD 10 |
| 8 | 33 | 43 Racemic mixture | | 406 | 3.14 | METHOD 10 |

-continued

| Starting Acid | Starting Amine | Ex. | Structure | MS m/z [M + H]⁺ | R_t (min) | Method |
|---|---|---|---|---|---|---|
| 8 | 34 | 44 Racemic mixture | 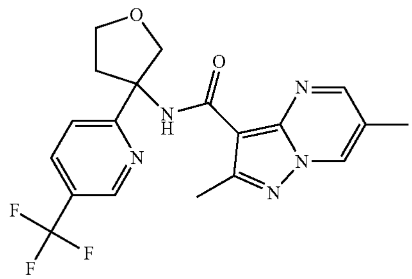 [SMILES: Cc1cnc2c(C(=O)NC3(c4ccc(C(F)(F)F)cn4)CCOC3)c(C)nn2c1] | 406 | 3.25 | METHOD 10 |
| 12 | 34 | 45 Racemic mixture | 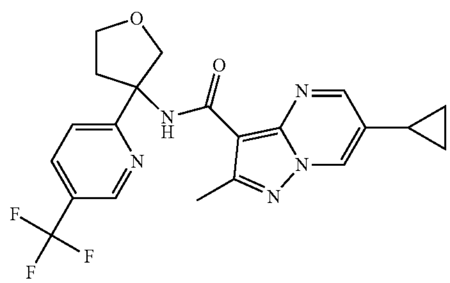 [SMILES: Cc1nn2cc(C3CC3)cnc2c1C(=O)NC1(c2ccc(C(F)(F)F)cn2)CCOC1] | 432 | 3.53 | METHOD 10 |

Example 46

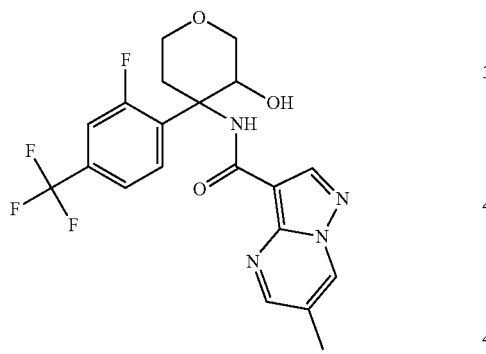

Example 47

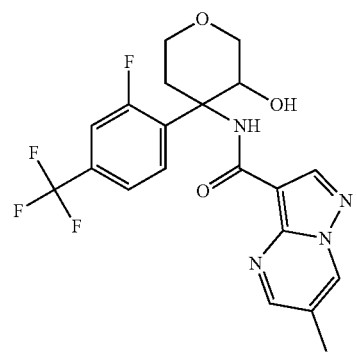 [SMILES: Cc1cnc2c(C(=O)NC3(c4ccc(C(F)(F)F)cc4F)CCOCC3O)cnn2c1]

Example 46 was synthesized in analogy to Example 1, starting from acid Intermediate 2 (34.6 mg, 0.2 mmol) and amino alcohol Intermediate 35 (65 mg, 0.19 mmol) to give, after flash chromatographic purification (eluent: water/acetonitrile; gradient from 10% to 100% of acetonitrile), 27 mg of the title compound, as TRANS-racemic mixture.

LC-MS (METHOD 1): R_t=3.70 min

MS (ESI pos): m/z=439 (M+H)⁺

1H NMR (500 MHz, DMSO-d_6) δ ppm 2.40 (d, J=1.00 Hz, 3H) 2.59-2.73 (m, 2H) 3.62-3.71 (m, 1H) 3.79-3.85 (m, 2H) 3.82 (br d, J=11.62 Hz, 2H) 4.02 (br d, 1H) 4.10 (m, 1H) 5.33 (br s, 1H) 7.46-7.50 (m, 1H) 7.55 (d, J=7.99 Hz, 1H) 7.73 (t, J=8.19 Hz, 1H) 8.34 (s, 1H) 8.42 (s, 1H) 8.81 (d, J=2.08 Hz, 1H) 9.19 (dd, J=1.96, 1.10 Hz, 1H)

NOE: 8.42 (NH): 4.10; 4.03; 3.65; 3.82 5.33 (OH): 4.10; 3.70

Further elution from the column in the preparation of Example 46 gave 5 mg of the title compound, as CIS-racemic mixture.

LC-MS (METHOD 1): R_t=3.97 min

MS (ESI pos): m/z=439 (M+H)⁺

1H NMR (500 MHz, DMSO-d_6) δ ppm 2.35-2.48 (m, 4H) 3.12 (br d, J=14.18 Hz, 1H) 3.47 (br t, J=11.86 Hz, 1H) 3.58 (t, J=10.76 Hz, 1H) 3.72 (br dd, J=11.62, 2.57 Hz, 1H) 3.74-3.84 (m, 1H) 4.10 (dd, J=10.03, 5.14 Hz, 1H) 5.66 (s, 1H) 7.47-7.59 (m, 2H) 7.61-7.67 (m, 1H) 8.49 (s, 1H) 8.62 (s, 1H) 8.76 (d, J=1.96 Hz, 1H) 9.21 (dd, J=2.08, 1.10 Hz, 1H)

NOE: 8.62 (NH): 4.10; 5.66; 2.49; 3.78; 3.12 5.66 (OH): 8.62; 4.10; 3.78; 3.12

The following Examples were prepared in analogy to Example 46 and Example 47 starting from the corresponding acid and amino alcohol Intermediates:

| Starting Acid | Starting Amino-alcohol | Ex. | Structure | MS m/z [M + H]+ | R$_t$ (min) | Method |
|---|---|---|---|---|---|---|
| 5 | 35 | 48 TRANS-Racemic mixture | | 465 | 4.12 | METHOD 1 |
| 5 | 35 | 49 CIS-Racemic mixture | | 465 | 4.33 | METHOD 1 |

Relative Stereochemistry Assigned by NMR:

| Example | | Relative stereochemistry | 1H-NMR | NOE |
|---|---|---|---|---|
| 48 | | TRANS Racemic mixture | 1H NMR (500 MHz, DMSO-d6) δ ppm 0.94-1.11 (m, 4 H) 2.11 (tt, J = 8.47, 5.10 Hz, 1 H) 2.56-2.76 (m, 2 H) 3.66 (td, J = 11.68, 2.08 Hz, 1 H) 3.81 (br d, J = 11.25 Hz, 2 H) 4.03 (d, J = 11.74 Hz, 1 H) 4.09 (m, 1 H) 5.33 (br s, 1 H) 7.46-7.50 (m, 1 H) 7.54 (d, J = 8.03 Hz, 1 H) 7.73 (t, J = 7.98 Hz, 1 H) 8.33 (s, 1 H) 8.40 (s, 1 H) 8.77 (d, J = 2.20 Hz, 1 H) 9.13 (d, J = 2.20 Hz, 1 H) | 8.40 (NH): 4.09 5.33 (OH): 4.09 |

| Example | | Relative stereochemistry | 1H-NMR | NOE |
|---|---|---|---|---|
| 49 | (structure shown) | CIS-Racemic mixture | 1H NMR (500 MHz, DMSO-d6) δ ppm 0.86-1.07 (m, 4 H) 2.06-2.16 (m, 1 H) 2.42-2.48 (m, 1 H) 3.12 (br d, J = 14.18 Hz, 1 H) 3.26-3.29 (m, 1 H) 3.47 (br t, J = 11.98 Hz, 1 H) 3.58 (t, J = 10.76 Hz, 1 H) 3.65-3.75 (m, 1 H) 3.78 (dd, J = 11.49, 5.14 Hz, 1 H) 4.09 (dd, J = 10.27, 5.14 Hz, 1 H) 5.66 (br s, 1 H) 7.48-7.60 (m, 2 H) 7.60-7.65 (m, 1 H) 8.48 (s, 1 H) 8.58 (s, 1 H) 8.71 (d, J = 2.20 Hz, 1 H) 9.14 (d, J = 1.71 Hz, 1 H) | 8.58 (NH): 5.66; 3.58; 3.47; 3.12 5.66 (OH): 8.58; 3.77 4.09 (CH): 2.46 |

Example 50

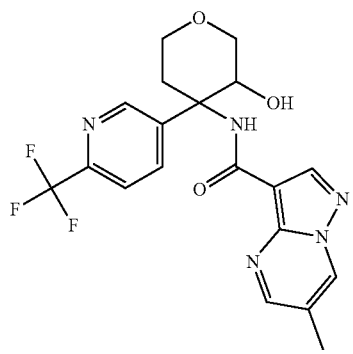 [SMILES: Cc1cnc2c(C(=O)NC3(c4ccc(C(F)(F)F)nc4)CCOCC3O)cnn2c1]

Example 50 was synthesized in analogy to Example 1, starting from acid Intermediate 2 (100 mg, 0.56 mmol) and amino alcohol Intermediate 36 (171.4 mg, 0.62 mmol) to give, after flash chromatographic purification (eluent: water/acetonitrile; gradient from 0% to 60% of acetonitrile), 209 mg of the title compound, as TRANS-racemic mixture.

LC-MS (METHOD 1): $R_t$=3.04 min

MS (ESI pos): m/z=422 (M+H)$^+$

1H NMR (400 MHz, DMSO-$d_6$) δ ppm 2.41 (s, 3H) 2.45-2.48 (m, 1H) 2.64-2.74 (m, 1H) 3.63-3.75 (m, 1H) 3.76-3.87 (m, 2H) 3.94 (br d, J=4.89 Hz, 1H) 4.08 (d, J=11.74 Hz, 1H) 5.30 (d, J=5.67 Hz, 1H) 7.83 (d, J=8.22 Hz, 1H) 8.10 (dd, J=8.31, 1.66 Hz, 1H) 8.38 (s, 1H) 8.44 (s, 1H) 8.82 (d, J=1.96 Hz, 1H) 8.85 (d, J=1.76 Hz, 1H) 9.20 (dd, J=1.96, 0.98 Hz, 1H)

NOE: 8.44 (NH): 4.08; 3,94; 3.68; 2.48 5.32 (OH): 8.58; 3.78, 2.68 3.94 (CH): 8.44; 2.48

The following Examples were prepared in analogy to Example 50 starting from the corresponding acid and amino alcohol Intermediates:

| Starting Acid | Starting Amino-alcohol | Ex. | Structure | MS m/z [M + H]$^+$ | $R_t$ (min) | Method |
|---|---|---|---|---|---|---|
| 12 | 36 | 51 TRANS-Racemic mixture | (structure shown) | 462 | 3.87 | METHOD 1 |

-continued

| Starting Acid | Starting Amino-alcohol | Ex. | Structure | MS m/z [M + H]+ | R$_t$ (min) | Method |
|---|---|---|---|---|---|---|
| 5 | 36 | 52 TRANS-Racemic mixture | 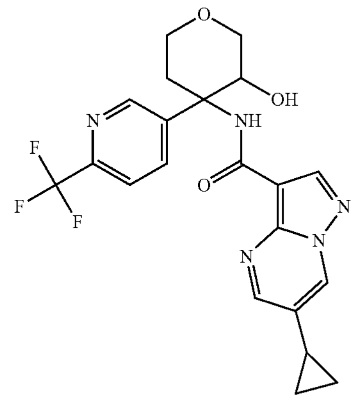 [SMILES: O=C(NC1(c2ccc(C(F)(F)F)nc2)CCOCC1O)c1cnn2cc(C3CC3)cnc12] | 448 | 3.58 | METHOD 1 |

Relative Stereochemistry Assigned by NMR:

| Example | | Relative stereochemistry | 1H-NMR |
|---|---|---|---|
| 51 | | TRANS Racemic mixture | 1H NMR (400 MHz, DMSO-d6) δ ppm 0.86-1.07 (m, 4 H) 2.03-2.17 (m, 1 H) 2.47 (s, 3 H) 2.49-2.5 (m, 1H) 2.68 (td, J = 12.57, 4.40 Hz, 1 H) 3.64- 3.72 (m, 1 H) 3.77-3.88 (m, 3 H) 4.10 (d, J = 12.13 Hz, 1 H) 5.28 (d, J = 5.67 Hz, 1 H) 7.83 (d, J = 8.22 Hz, 1 H) 8.08 (d, J = 7.73 Hz, 1 H) 8.65 (s, 1 H) 8.71 (d, J = 1.96 Hz, 1 H) 8.83 (s, 1 H) 9.03 (d, J = 1.96 Hz, 1 H) |
| 52 | | TRANS Racemic mixture | 1H NMR (400 MHz, DMSO-d6) δ ppm 0.91-1.09 (m, 4 H) 2.08-2.15 (m, 1 H) 2.46 (s, 1 H) 2.59-2.78 (m, 1 H) 3.64-3.75 (m, 1 H) 3.76-3.86 (m, 2 H) 3.92 (br d, J = 4.21 Hz, 1 H) 4.08 (d, J = 11.93 Hz, 1 H) 5.29 (d, J = 5.77 Hz, 1 H) 7.83 (d, J = 8.31 Hz, 1 H) 8.10 (dd, J = 8.12, 2.15 Hz, 1 H) 8.37 (s, 1 H) 8.43 (s, 1 H) 8.77 (d, J = 2.15 Hz, 1 H) 8.84 (d, J = 1.96 Hz, 1 H) 9.14 (d, J = 2.15 Hz, 1 H) |

Example 53

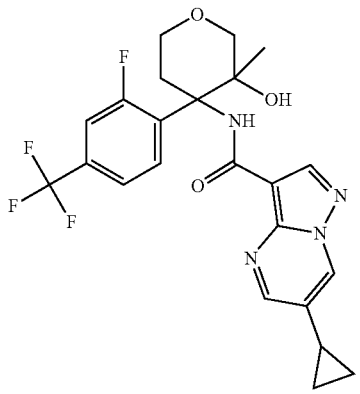 [SMILES: CC1(O)COCCC1(NC(=O)c1cnn2cc(C3CC3)cnc12)c1ccc(C(F)(F)F)cc1F]

Example 53 was synthesized in analogy to Example 1, starting from acid Intermediate 5 (98 mg, 0.48 mmol) and amino alcohol Intermediate 38 (198 mg, 0.48 mmol) to give, after flash chromatographic purification (eluent: water/acetonitrile; gradient from 10% to 80% of acetonitrile), 7 mg of the title compound, as CIS-racemic mixture.

LC-MS (METHOD 1): $R_t$=4.45 min
MS (ESI pos): m/z=479 (M+H)$^+$
1H NMR (500 MHz, DMSO-d$_6$) δ ppm 0.94-1.07 (m, 4H) 1.12 (s, 3H) 2.12 (tt, J=8.38, 5.20 Hz, 1H) 2.72 (br t, J=11.98 Hz, 1H) 2.98 (br d, J=13.69 Hz, 1H) 3.47 (d, J=11.25 Hz, 1H) 3.56 (br t, J=11.74 Hz, 1H) 3.72-3.76 (m, 1H) 3.76-3.87 (m, 1H) 5.38 (s, 1H) 7.46-7.56 (m, 2H) 7.70 (t, J=8.07 Hz, 1H) 8.35 (s, 1H) 8.72 (d, J=2.20 Hz, 1H) 8.88-8.95 (m, 1H) 9.12 (d, J=2.20 Hz, 1H)
NOE: 8.92 (NH): 5.38; 3.80 5.38 (OH): 8.92; 3.80

Example 54

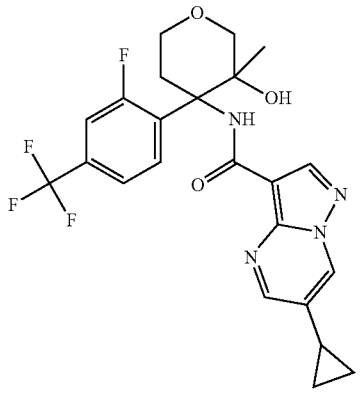 [SMILES: CC1(O)COCCC1(NC(=O)c1cnn2cc(C3CC3)cnc12)c1ccc(C(F)(F)F)cc1F]

Further elution from the column in the preparation of Example 53 gave 29 mg of the title compound, as racemic mixture (TRANS/CIS diastereoisomeric ratio 92/8 determined by NMR).

LC-MS (METHOD 1): $R_t$=4.45 min
MS (ESI pos): m/z=479 (M+H)$^+$
1H NMR (500 MHz, DMSO-d$_6$) δ ppm 0.95-1.07 (m, 4H) 1.10 (d, 3H) 2.12 (tt, J=8.44, 5.14 Hz, 1H) 2.51-2.56 (m, 1H) 3.03 (td, J=12.65, 4.28 Hz, 1H) 3.53-3.65 (m, 2H) 3.74-3.76 (m, 1H) 3.88 (d, J=12.23 Hz, 1H) 5.10 (s, 1H) 7.44-7.48 (dd, 1H) 7.53 (d, J=8.27 Hz, 1H) 7.66 (t, J=8.05 Hz, 1H) 8.38 (s, 1H) 8.48 (s, 1H) 8.79 (d, J=2.20 Hz, 1H) 9.16 (d, J=2.20 Hz, 1H)
NOE: 8.48 (NH): 1.09; 3.88; 2.53 5.10 (OH): 3.04, 3.57 1.09 (Me): 8.48; 3.57; 2.53; 3.88

Example 55

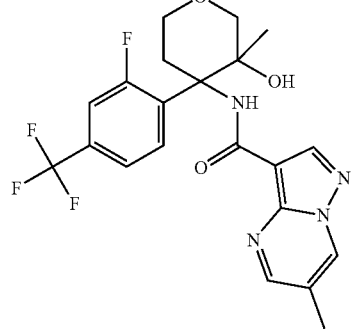

Example 55 was synthesized in analogy to Example 1, starting from acid Intermediate 2 (304 mg, 1.68 mmol) and amino alcohol Intermediate 38 (700 mg, 1.68 mmol) to give, after flash chromatographic purification (eluent: water/acetonitrile; gradient from 10% to 100% of acetonitrile), 300 mg of the title compound, as racemic mixture (TRANS/CIS diastereoisomeric ratio 96/4 determined by NMR).

LC-MS (METHOD 1): $R_t$=4.02 min MS (ESI pos): m/z=453 (M+H)$^+$
1H NMR (500 MHz, DMSO-d$_6$) δ ppm 1.10 (d, J=1.00 Hz, 3H) 2.41 (d, J=0.86 Hz, 3H) 2.52-2.58 (m, 1H) 3.03 (br d, J=4.16 Hz, 1H) 3.46-3.66 (m, 2H) 3.72-3.82 (m, 1H) 3.88 (d, J=12.23 Hz, 1H) 5.10 (s, 1H) 7.46 (br d, J=12.72 Hz, 1H) 7.50-7.57 (m, 1H) 7.67 (t, J=8.23 Hz, 1H) 8.35-8.39 (m, 1H) 8.50 (s, 1H) 8.83 (d, J=1.96 Hz, 1H) 9.18-9.24 (m, 1H)
NOE: 8.50 (NH): 1.10; 3.89; 3.64 5.10 (OH): 3.03, 3.58 1.10 (Me): 8.50; 3.56; 3.89

Example 56

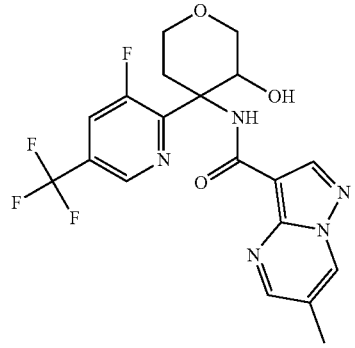

Example 56 was synthesized in analogy to Example 1, starting from acid Intermediate 2 (36 mg, 0.21 mmol) and amino alcohol Intermediate 39 (55 mg, 0.2 mmol) to give, after flash chromatographic purification (eluent: water/acetonitrile; gradient from 10% to 65% of acetonitrile), 52 mg of the title compound, as TRANS-racemic mixture.

LC-MS (METHOD 1): R$_t$=3.57 min
MS (ESI pos): m/z=440 (M+H)$^+$
1H NMR (400 MHz, DMSO-d$_6$) δ ppm 2.40 (s, 3H) 2.42-2.48 (m, 1H) 2.89 (td, J=13.35, 4.40 Hz, 1H) 3.65 (br t, J=11.30 Hz, 1H) 3.79-3.89 (m, 2H) 4.01 (d, J=12.42 Hz, 1H) 4.09 (s, 1H) 5.35 (br s, 1H) 8.11 (d, J=11.84 Hz, 1H) 8.35 (s, 1H) 8.46 (s, 1H) 8.81 (d, J=1.76 Hz, 2H) 9.20 (s, 1H)

Example 57

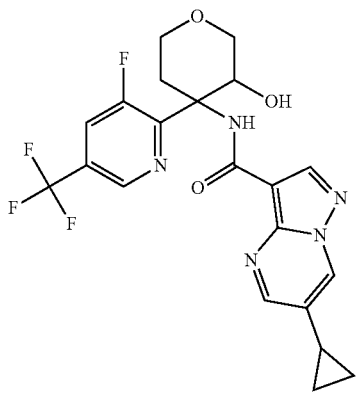 [SMILES: O=C(NC1(c2ncc(C(F)(F)F)cc2F)CCOCC1O)c1cnn2cc(C3CC3)cnc12]

Example 57 was synthesized in analogy to Example 1, starting from acid Intermediate 5 (42 mg, 0.21 mmol) and amino alcohol Intermediate 39 (55 mg, 0.2 mmol) to give, after flash chromatographic purification (eluent: water/acetonitrile; gradient from 10% to 70% of acetonitrile), 48 mg of the title compound, as TRANS-racemic mixture.
LC-MS (METHOD 1): R$_t$=4.00 min
MS (ESI pos): m/z=466 (M+H)$^+$
1H NMR (400 MHz, DMSO-d$_6$) δ ppm 0.87-1.11 (m, 4H) 2.07-2.15 (m, 1H) 2.47 (m, 1H) 2.89 (td, J=13.11, 4.11 Hz, 1H) 3.64 (br t, J=11.54 Hz, 1H) 3.78-3.89 (m, 2H) 4.01 (d, J=12.52 Hz, 1H) 4.09 (br s, 1H) 5.35 (br s, 1H) 8.11 (d, J=11.93 Hz, 1H) 8.34 (s, 1H) 8.44 (s, 1H) 8.77 (s, 1H) 8.81 (s, 1H) 9.14 (d, J=1.96 Hz, 1H)

Example 58

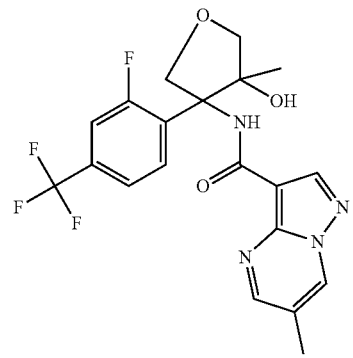 [SMILES: Cc1cnc2c(C(=O)NC3(c4ccc(C(F)(F)F)cc4F)COCC3(C)O)cnn2c1]

Example 58 was synthesized in analogy to Example 1, starting from acid Intermediate 2 (187 mg, 1.06 mmol) and amino alcohol Intermediate 41 (378 mg, 0.96 mmol) to give, after flash chromatographic purification (eluent: dichloromethane/MeOH; gradient from 0% to 60% of MeOH), 22 mg of the title compound, as racemic mixture (TRANS/CIS diastereoisomeric ratio 91/9)

LC-MS (METHOD 10): R$_t$=3.16 min
MS (ESI pos): m/z=439 (M+H)$^+$
1H NMR (500 MHz, DMSO-d$_6$) δ ppm 1.56 (s, 3H) 2.40 (d, J=0.73 Hz, 4H) 3.78 (d, J=9.05 Hz, 1H) 3.90 (d, J=9.05 Hz, 1H) 4.39 (d, J=8.80 Hz, 1H) 4.90 (d, J=8.80 Hz, 1H) 5.31 (s, 1H) 7.48-7.56 (m, 2H) 7.71 (t, J=8.07 Hz, 1H) 8.37 (s, 1H) 8.67 (s, 1H) 8.82 (d, J=1.96 Hz, 1H) 9.09-9.26 (m, 1H) 9.21 (dd, J=2.08, 1.10 Hz, 1H)
NOE: 8.67 (NH): 1.56; 3,90; 4.38 5.31 (OH): 3.78, 4.90 1.56 (Me): 8.67

Example 59

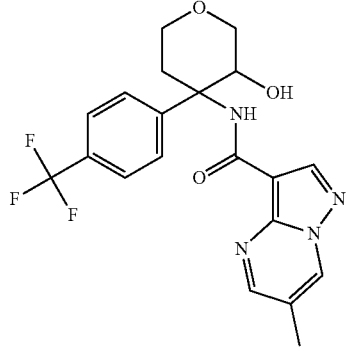

Example 59 was synthesized in analogy to Example 1, starting from acid Intermediate 2 (35.6 mg, 0.20 mmol) and amino alcohol Intermediate 42 (50 mg, 0.19 mmol) to give, after flash chromatographic purification (eluent: water/acetonitrile; gradient from 10% to 65% of acetonitrile), 42 mg of the title compound, as TRANS-racemic mixture.
LC-MS (METHOD 1): R$_t$=3.77 min
MS (ESI pos): m/z=421 (M+H)$^+$
1H NMR (500 MHz, DMSO-d$_6$) δ ppm 2.40 (d, J=0.98 Hz, 3H) 2.51-2.54 (m, 1H) 2.62-2.70 (m, 1H) 3.67 (td, J=11.68, 1.83 Hz, 1H) 3.75-3.82 (m, 2H) 3.82-3.89 (m, 1H) 4.06 (d, J=11.49 Hz, 1H) 5.14 (br d, J=4.16 Hz, 1H) 7.62-7.70 (m, 4H) 8.35 (s, 1H) 8.37 (s, 1H) 8.80 (d, J=1.96 Hz, 1H) 9.19 (dd, J=2.08, 1.10 Hz, 1H)

Example 60

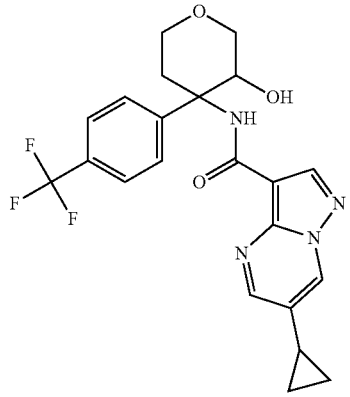

Example 60 was synthesized in analogy to Example 1, starting from acid Intermediate 5 (40.8 mg, 0.2 mmol) and amino alcohol Intermediate 42 (50 mg, 0.19 mmol) to give, after flash chromatographic purification (eluent: water/acetonitrile; gradient from 10% to 70% of acetonitrile), 39 mg of the title compound, as TRANS-racemic mixture.

LC-MS (METHOD 1): $R_t$=4.07 min

MS (ESI pos): m/z=424 (M+H)$^+$

1H NMR (500 MHz, DMSO-$d_6$) δ ppm 0.86-1.06 (m, 4H) 2.07-2.14 (m, 1H) 2.51-2.53 (m, 1H) 2.62-2.70 (m, 1H) 3.66 (td, J=11.74, 1.71 Hz, 1H) 3.75-3.87 (m, 3H) 4.07 (d, J=11.25 Hz, 1H) 5.14 (d, J=5.62 Hz, 1H) 7.62-7.70 (m, 4H) 8.35 (s, 1H) 8.36 (s, 1H) 8.76 (d, J=2.20 Hz, 1H) 9.13 (d, J=2.20 Hz, 1H)

Example 61

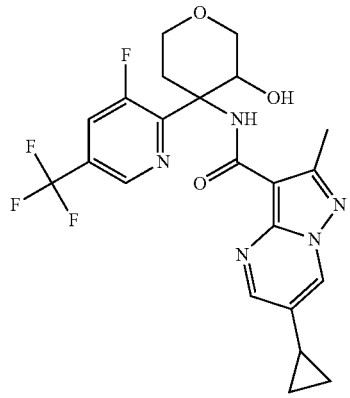 [SMILES: Cc1nn2cc(C3CC3)cnc2c1C(=O)NC1(c2ncc(C(F)(F)F)cc2F)CCOCC1O]

Example 61 was synthesized in analogy to Example 1, starting from acid Intermediate 12 (82 mg, 0.29 mmol) and amino alcohol Intermediate 39 (66.7 mg, 0.31 mmol) to give, after flash chromatographic purification (eluent: water/acetonitrile; gradient from 10% to 70% of acetonitrile), 110 mg of the title compound, as TRANS-racemic mixture.

LC-MS (METHOD 1): $R_t$=4.22 min

MS (ESI pos): m/z=480 (M+H)$^+$

1H NMR (500 MHz, DMSO-$d_6$) δ ppm 0.90-1.06 (m, 4H) 2.09 (tt, J=8.44, 5.14 Hz, 1H) 2.45 (s, 3H) 2.47 (m, 1H) 2.88 (td, J=13.27, 4.28 Hz, 1H) 3.59-3.67 (m, 1H) 3.77-3.88 (m, 2H) 4.01-4.05 (m, 1H) 4.08 (br d, J=5.14 Hz, 1H) 5.32 (d, J=5.62 Hz, 1H) 8.11 (dd, J=11.86, 1.59 Hz, 1H) 8.69 (s, 1H) 8.71 (d, J=2.36 Hz, 1H) 8.81 (s, 1H) 9.03 (d, J=2.20 Hz, 1H)

NOE: 8.69 (NH): 4.08; 2.47 3.64 5.32 (OH): 3.82, 2.88 4.08 (CH): 8.69; 2.47

Example 62

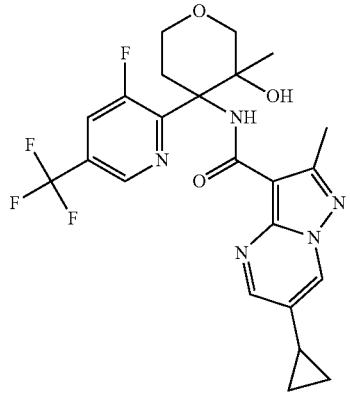 [SMILES: Cc1nn2cc(C3CC3)cnc2c1C(=O)NC1(c2ncc(C(F)(F)F)cc2F)CCOCC1(C)O]

Example 62 was synthesized in analogy to Example 1, starting from acid Intermediate 12 (103 mg, 0.6 mmol) and amino alcohol Intermediate 43 (250 mg, 0.6 mmol) to give, after flash chromatographic purification (eluent: water/acetonitrile; gradient from 10% to 70% of acetonitrile), 115 mg of the title compound, as TRANS-racemic mixture.

LC-MS (METHOD 1): $R_t$=4.40 min

MS (ESI pos): m/z=494 (M+H)$^+$

1H NMR (500 MHz, DMSO-$d_6$) δ ppm 0.92-1.06 (m, 4H) 1.21 (d, J=3.18 Hz, 3H) 2.10 (tt, J=8.47, 5.23 Hz, 1H) 2.30-2.36 (m, 1H) 2.47-2.49 (m, 3H) 3.22-3.29 (m, 1H) 3.49-3.54 (m, 1H) 3.62 (br t, J=10.88 Hz, 1H) 3.76-3.88 (m, 2H) 4.96 (s, 1H) 8.08 (dd, J=11.98, 1.47 Hz, 1H) 8.72 (d, J=1.96 Hz, 1H) 8.78 (s, 1H) 8.84 (s, 1H) 9.05 (d, J=2.20 Hz, 1H)

NOE: 8.78 (NH): 1.21; 2.34; 3.62 4.96 (OH): 3.51, 3.35 1.21 (Me): 8.78; 2.34

Example 63

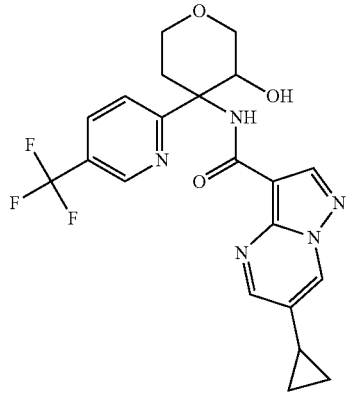 [SMILES: O=C(NC1(c2ccc(C(F)(F)F)cn2)CCOCC1O)c1cnn2cc(C3CC3)cnc12]

Example 63 was synthesized in analogy to Example 1, starting from acid Intermediate 5 (45 mg, 0.22 mmol) and amino alcohol Intermediate 40 (55 mg, 0.21 mmol) to give, after flash chromatographic purification (eluent: water/acetonitrile; gradient from 10% to 70% of acetonitrile), 55 mg of the title compound, as TRANS-racemic mixture.

LC-MS (METHOD 1): $R_t$=3.82 min

MS (ESI pos): m/z=448 (M+H)$^+$

1H NMR (500 MHz, DMSO-d$_6$) δ ppm 0.91-1.08 (m, 4H) 2.06-2.17 (m, 1H) 2.41-2.48 (m, 1H) 2.76-2.84 (m, 1H) 3.65-3.76 (m, 2H) 3.92 (dt, J=11.23, 3.58 Hz, 1H) 3.95-4.00 (m, 1H) 4.04 (br s, 1H) 5.24 (d, J=4.03 Hz, 1H) 7.75 (d, J=8.44 Hz, 1H) 8.11 (dd, J=8.50, 2.02 Hz, 1H) 8.33 (s, 1H) 8.43 (s, 1H) 8.76 (d, J=2.08 Hz, 1H) 8.88 (dd, J=1.53, 0.79 Hz, 1H) 9.13 (d, J=2.20 Hz, 1H) NOE 8.43 (NH): 4.04; 2.44; 3.98 5.24 (OH): 3.66, 2.80 4.04 (CH): 8.43; 2.44

Example 64

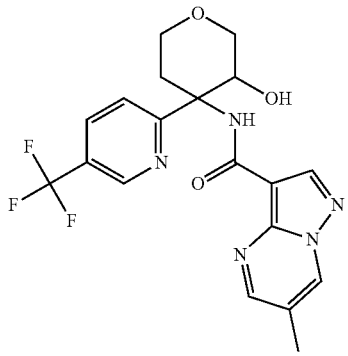 [SMILES: Cc1cnc2c(C(=O)NC3(c4ccc(C(F)(F)F)cn4)CCOCC3O)cnn2c1]

Example 64 was synthesized in analogy to Example 1, starting from acid Intermediate 2 (39 mg, 0.22 mmol) and amino alcohol Intermediate 40 (55 mg, 0.21 mmol) to give, after flash chromatographic purification (eluent: water/acetonitrile; gradient from 10% to 65% of acetonitrile), 31 mg of the title compound, as TRANS-racemic mixture.

LC-MS (METHOD 10): R$_t$=2.66 min
MS (ESI pos): m/z=422 (M+H)$^+$
1H NMR (500 MHz, DMSO-d$_6$) δ ppm 2.40 (s, 3H) 2.42 (br s, 1H) 2.76-2.85 (m, 1H) 3.64-3.77 (m, 2H) 3.90-3.95 (m, 1H) 3.97 (br d, J=12.23 Hz, 1H) 4.05 (br s, 1H) 5.24 (d, J=5.56 Hz, 1H) 7.75 (d, J=8.44 Hz, 1H) 8.11 (dd, J=8.47, 2.11 Hz, 1H) 8.33 (s, 1H) 8.45 (s, 1H) 8.80 (d, J=1.90 Hz, 1H) 8.88 (s, 1H) 9.19 (s, 1H)
NOE: 8.45 (NH): 4.05; 2.44; 3.98; 3.68 5.24 (OH): 3.72; 3.97; 2.80 4.05 (CH): 8.45; 2.44

Example 65

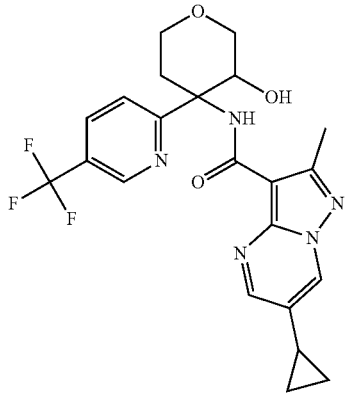

Example 65 was synthesized in analogy to Example 1, starting from acid Intermediate 12 (78 mg, 0.36 mmol) and amino alcohol Intermediate 40 (90 mg, 0.34 mmol) to give, after flash chromatographic purification (eluent: water/acetonitrile; gradient from 10% to 70% of acetonitrile), 110 mg of the title compound, as TRANS-racemic mixture.

LC-MS (METHOD 1): R$_t$=4.07 min
MS (ESI pos): m/z=462 (M+H)$^+$
1H NMR (500 MHz, DMSO-d$_6$) δ ppm 0.90-1.07 (m, 4H) 2.09 (tt, J=8.59, 4.98 Hz, 1H) 2.42-2.47 (m, 4H) 2.79 (ddd, J=13.66, 11.34, 4.34 Hz, 1H) 3.64-3.76 (m, 2H) 3.91 (dt, J=11.28, 3.59 Hz, 1H) 3.99 (d, J=12.35 Hz, 1H) 3.98-3.99 (m, 1H) 4.02 (br s, 1H) 5.21 (d, J=4.52 Hz, 1H) 7.73 (d, J=8.44 Hz, 1H) 8.12 (dd, J=8.50, 2.14 Hz, 1H) 8.69 (d, J=10.11 Hz, 2H) 8.88 (dd, J=1.47, 0.73 Hz, 1H) 9.02 (d, J=1.83 Hz, 1H)

Example 66

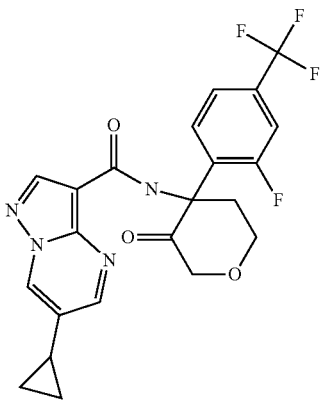 [SMILES: O=C(NC1(c2ccc(C(F)(F)F)cc2F)CCOCC1=O)c1cnn2cc(C3CC3)cnc12]

Example 66 was synthesized in analogy to Example 1, starting from acid Intermediate 5 (16.8 mg, 0.08 mmol) and amino alcohol Intermediate 44 (20 mg, 0.08 mmol) to give, after flash chromatographic purification (eluent: water/acetonitrile; gradient from 0% to 100% of acetonitrile), 11 mg of the title compound.

LC-MS (METHOD 1): R$_t$=4.78 min
MS (ESI pos): m/z=463 (M+H)$^+$

Example 67

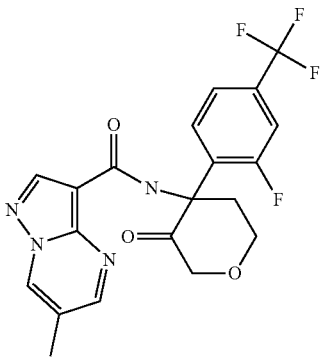 [SMILES: Cc1cnc2c(C(=O)NC3(c4ccc(C(F)(F)F)cc4F)CCOCC3=O)cnn2c1]

Example 67 was synthesized in analogy to Example 1, starting from acid Intermediate 2 (19.7 mg, 0.11 mmol) and amino alcohol Intermediate 44 (35 mg, 0.11 mmol) to give, after flash chromatographic purification (eluent: water/acetonitrile; gradient from 0% to 100% of acetonitrile), 24 mg of the title compound.

LC-MS (METHOD 1): R$_t$=4.40 min
MS (ESI pos): m/z=437 (M+H)$^+$

Examples 68, 69, 70, 71

Examples 68, 69, 70 and 71 were synthesized in analogy to Example 1, starting from acid Intermediate 5 (150 mg, 0.74 mmol) and amino alcohol Intermediate 37 (230 mg, 0.71 mmol) to give, after flash chromatographic purification (eluent: water/acetonitrile; gradient from 0% to 80% of acetonitrile), 143 mg of mixture of the title compounds, which were obtained as single stereoisomers by chiral HPLC separation.

| Ex. # | Structure | MS m/z [M + H]$^+$ | R$_t$ (min) [LC-MS Method] | R$_t$ (min) [Chiral HPLC Method] |
|---|---|---|---|---|
| 68 CIS single stereoisomer a | 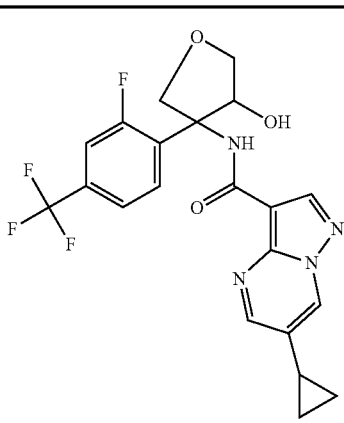 | 451 | 4.28 METHOD 1 | 9.66 [C3] |
| 69 CIS single stereoisomer b | 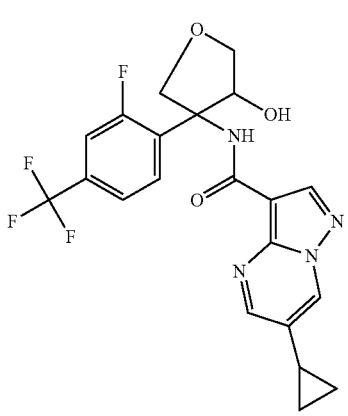 [SMILES: O=C(NC1(c2ccc(C(F)(F)F)cc2F)COCC1O)c1cnn2cc(C3CC3)cnc12] | 451 | 4.28 METHOD 1 | 11.30 [C3] |
| 70 TRANS stereoisomer a | 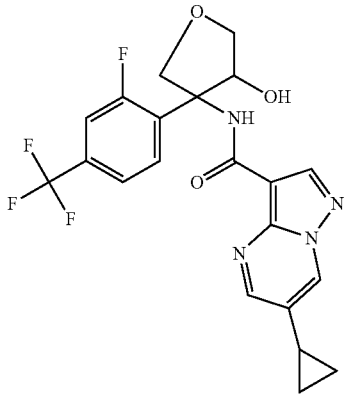 [SMILES: O=C(NC1(c2ccc(C(F)(F)F)cc2F)COCC1O)c1cnn2cc(C3CC3)cnc12] | 451 | 4.21 METHOD 1 | 16.32, [C3] |

| Ex. # | Structure | MS m/z [M + H]+ | R_t (min) [LC-MS Method] | R_t (min) [Chiral HPLC Method] |
|---|---|---|---|---|
| 71 TRANS single stereoisomer b | 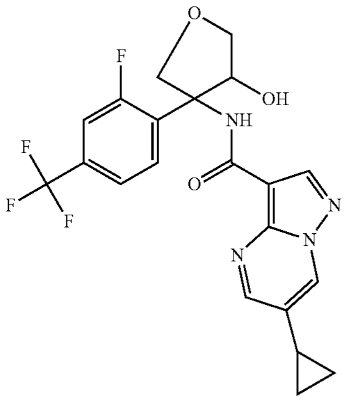 [SMILES: O=C(NC1(c2ccc(C(F)(F)F)cc2F)COCC1O)c1cnn2cc(C3CC3)cnc12] | 451 | 4.23 METHOD 1 | 22.71 [C3] |

Relative Stereochemistry Assigned by NMR:

| Example | Structure | Relative stereochemistry | 1H-NMR | NOE |
|---|---|---|---|---|
| 68 | | CIS single stereoisomer a | 1H NMR (500 MHz, DMSO-d6) δ ppm 0.94-1.06 (m, 4 H) 2.07-2.14 (m, 1 H) 3.58 (dd, J = 9.29, 5.14 Hz, 1 H) 4.02 (dd, J = 9.29, 5.87 Hz, 1 H) 4.14 (d, J = 9.78 Hz, 1 H) 4.40 (br s, 1 H) 4.80 (d, J = 10.03 Hz, 1 H) 6.34 (br s, 1 H) 7.54-7.63 (m, 2 H) 7.63-7.68 (m, 1 H) 8.39 (s, 1 H) 8.72 (d, J = 2.20 Hz, 1 H) 9.09-9.13 (m, 2 H) | 9.11 (NH): 6.34; 4.14; 3.58 6.34(OH): 9.11, 4.14; 3.58 4.40 (CH): 4.80 |
| 69 | | CIS single stereoisomer b | 1H NMR (500 MHz, DMSO-d6) δ ppm 0.94-1.06 (m, 4 H) 2.07-2.14 (m, 1 H) 3.58 (dd, J = 9.29, 5.14 Hz, 1 H) 4.02 (dd, J = 9.29, 5.87 Hz, 1 H) 4.14 (d, J = 9.78 Hz, 1 H) 4.40 (br s, 1 H) 4.80 (d, J = 10.03 Hz, 1 H) 6.34 (br s, 1 H) 7.54-7.63 (m, 2 H) 7.63-7.68 (m, 1 H) 8.39 (s, 1 H) 8.72 (d, J = 2.20 Hz, 1 H) 9.09-9.13 (m, 2 H) | 9.11 (NH): 6.34; 4.14; 3.58 6.34(OH): 9.11, 4.14; 3.58 4.40 (CH): 4.80 |

| Example | Relative stereochemistry | | 1H-NMR | NOE |
|---|---|---|---|---|
| 70 | TRANS single stereoisomer a | (structure) | 1H NMR (500 MHz, DMSO-d6) δ ppm 0.92 -1.07 (m, 4 H) 3.71-3.80 (m, 1 H) 4.25 (dd, J = 9.78, 4.40 Hz, 1 H) 4.35 (d, J = 8.80 Hz, 1 H) 4.69 (d, J = 8.80 Hz, 1 H) 4.76 (br s, 1 H) 5.64 (br s, 1 H) 7.51-7.56 (m, 2 H) 7.73 (t, J = 7.82 Hz, 1 H) 8.28 (s, 1 H) 8.36 (s, 1 H) 8.74 (d, J = 1.96 Hz, 1 H) 9.09-9.11 (m, 1 H) | 8.28 (NH): 4.69; 4.76; 4.25 5.64(OH): 4.35; 3.76 4.76 (CH): 8.28 |
| 71 | TRANS single stereoisomer b | (structure) | 1H NMR (500 MHz, DMSO-d6) δ ppm 0.92-1.07 (m, 4 H) 3.71-3.80 (m, 1 H) 4.25 (dd, J = 9.78, 4.40 Hz, 1 H) 4.35 (d, J = 8.80 Hz, 1 H) 4.69 (d, J = 8.80 Hz, 1 H) 4.76 (br s, 1 H) 5.64 (br s, 1 H) 7.51-7.56 (m, 2 H) 7.73 (t, J = 7.82 Hz, 1 H) 8.28 (s, 1 H) 8.36 (s, 1 H) 8.74 (d, J = 1.96 Hz, 1 H) 9.09-9.11 (m, 1 H) | 8.28 (NH): 4.69; 4.76; 4.25 5.64(OH): 4.35; 3.76 4.76 (CH): 8.28 |

Examples 72, 73, 74, 75

Examples 72, 73, 74 and 75 were synthesized in analogy to Example 1, starting from acid Intermediate 2 (92 mg, 0.52 mmol) and amino alcohol Intermediate 37 (160 mg, 43% content, 0.26 mmol) to give, after two subsequent flash chromatographic purifications (eluent: water/acetonitrile; gradient from 0% to 80% of acetonitrile; eluent: DCM/isopropyl alcohol; gradient from 0% to 30% of isopropyl alcohol), 110 mg of mixture of the title compounds, which were obtained as single stereoisomers by chiral HPLC separation.

| Ex. # | Structure | MS m/z [M + H]$^+$ | R$_t$ (min) [LC-MS Method] | R$_t$ (min) [Chiral HPLC Method] |
|---|---|---|---|---|
| 72 CIS single stereoisomer a | (structure) | 425 | 3.84 METHOD 1 | 12.08 [C3] |

| Ex. # | Structure | MS m/z [M + H]+ | R$_t$ (min) [LC-MS Method] | R$_t$ (min) [Chiral HPLC Method] |
|---|---|---|---|---|
| 73 CIS single stereoisomer b | 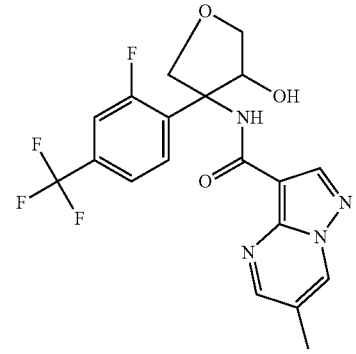 [SMILES: Cc1cnc2c(C(=O)NC3(c4ccc(C(F)(F)F)cc4F)COCC3O)cnn2c1] | 425 | 3.85 METHOD 1 | 13.41 [C3] |
| 74 TRANS single stereoisomer a | 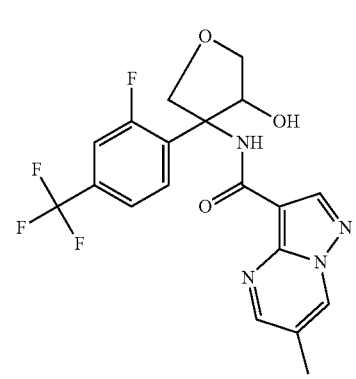 [SMILES: Cc1cnc2c(C(=O)NC3(c4ccc(C(F)(F)F)cc4F)COCC3O)cnn2c1] | 425 | 3.75 METHOD 1 | 22.54 [C3] |
| 75 TRANS single stereoisomer b | 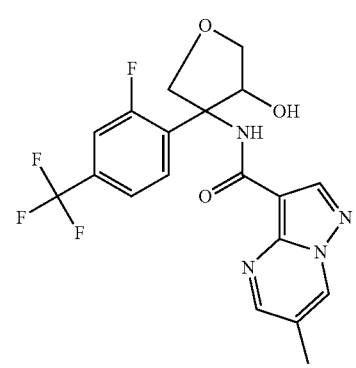 [SMILES: Cc1cnc2c(C(=O)NC3(c4ccc(C(F)(F)F)cc4F)COCC3O)cnn2c1] | 425 | 3.78 METHOD 1 | 26.59 [C3] |
The following examples were obtained as single stereoisomers by chiral HPLC separation of the corresponding racemic mixture:

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 40 | 80 a Single stereoisomer a | | 450 | 3.89 METHOD 10 | 5.98 [C1] |
| 40 | 80b single stereoisomer b | | 450 | 3.89 METHOD 10 | 6.76 [C1] |
| 46 TRANS-Racemic mixture | 81a TRANS-single stereoisomer a | | 439 | 3.67 METHOD 1 | 11.19 [C4] |
| 46 TRANS-Racemic mixture | 81b TRANS-single stereoisomer b | | 439 | 3.67 METHOD 1 | 13.99 [C4] |

-continued

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 48 TRANS-Racemic mixture | 82a TRANS-single stereoisomer a | | 465 | 3.41 METHOD 10 | 11.78 [C4] |
| 48 TRANS-Racemic mixture | 82b TRANS-single stereoisomer b | | 465 | 3.41 METHOD 10 | 14.22 [C4] |
| 55 TRANS/CIS 96/4 Racemic mixture | 83a TRANS-single stereoisomer a | | 453 | METHOD 1 | 11.71 [C3] |
| 55 TRANS/CIS 96/4 Racemic mixture | 83b TRANS-single stereoisomer b | | 453 | 4.07 METHOD 1 | 26.90 [C3] |

-continued

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 55 TRANS/ CIS 96/4 Racemic mixture | 84a CIS- single stereoisomer a | 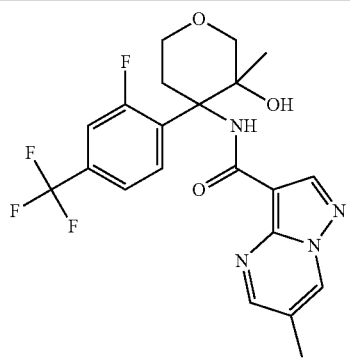 [SMILES: Cc1cnc2c(C(=O)NC3(c4ccc(C(F)(F)F)cc4F)CCOCC3(C)O)cnn2c1] | 453 | 4.07 METHOD 1 | 13.67 [C3] |
| 55 TRANS/ CIS 96/4 Racemic mixture | 84b CIS- single stereoisomer b | 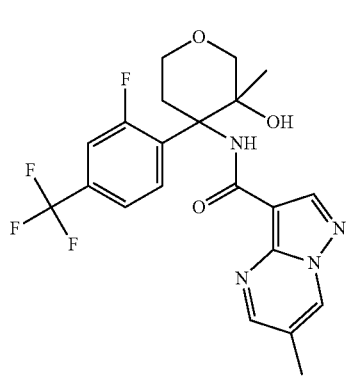 [SMILES: Cc1cnc2c(C(=O)NC3(c4ccc(C(F)(F)F)cc4F)CCOCC3(C)O)cnn2c1] | 453 | 4.07 METHOD 1 | 18.13 [C3] |
| 54 TRANS/ CIS 92/8 Racemic mixture | 85a CIS- single stereoisomer a | 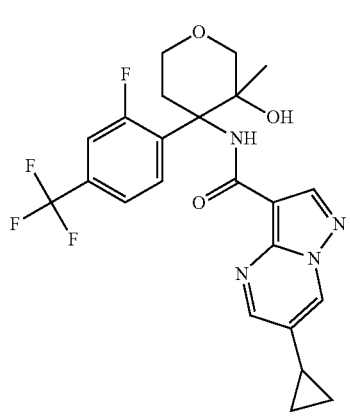 [SMILES: CC1(O)COCCC1(NC(=O)c1cnn2cc(C3CC3)cnc12)c1ccc(C(F)(F)F)cc1F] | 479 | 4.48 METHOD 1 | 5.46 [C1] |
| 54 TRANS/ CIS 92/8 Racemic mixture | 85b CIS- single stereoisomer b | 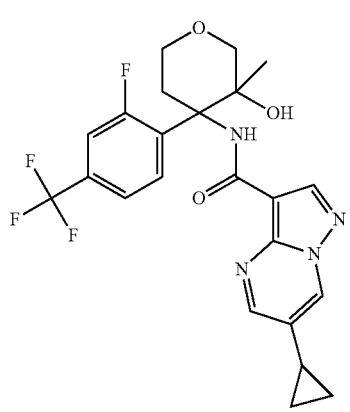 [SMILES: CC1(O)COCCC1(NC(=O)c1cnn2cc(C3CC3)cnc12)c1ccc(C(F)(F)F)cc1F] | 479 | 4.48 METHOD 1 | 6.73 [C1] |

-continued

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 54 TRANS/CIS 92/8 Racemic mixture | 86a TRANS- single stereoisomer a | 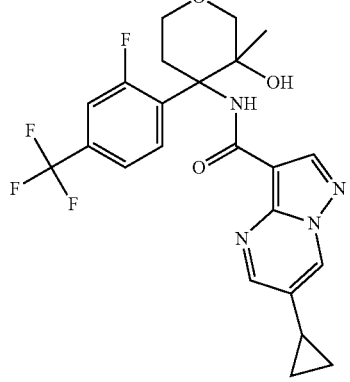 | 479 | 4.48 METHOD 1 | 6.08 [C1] |
| 54 TRANS/CIS 92/8 Racemic mixture | 86b TRANS- single stereoisomer b | 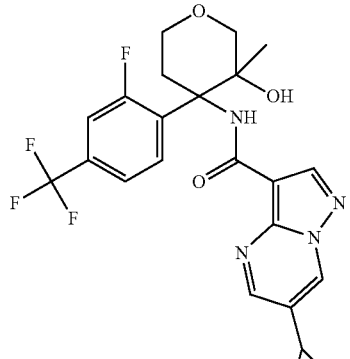 | 479 | 4.48 METHOD 1 | 10.75 [C1] |
| 50 TRANS- Racemic mixture | 87a TRANS- single stereoisomer a | 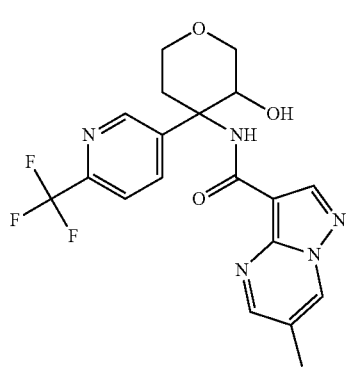 [SMILES: Cc1cnc2c(C(=O)NC3(c4ccc(C(F)(F)F)nc4)CCOCC3O)cnn2c1] | 422 | 3.08 METHOD 1 | 9.97 [C6] |
| 50 TRANS- Racemic mixture | 87b TRANS- single stereoisomer b | 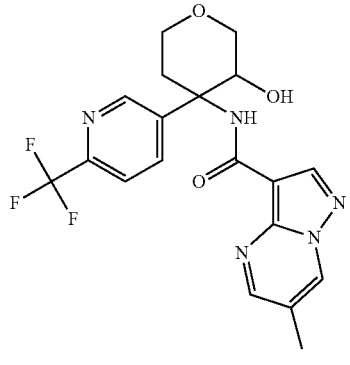 [SMILES: Cc1cnc2c(C(=O)NC3(c4ccc(C(F)(F)F)nc4)CCOCC3O)cnn2c1] | 422 | 3.08 METHOD 1 | 12.98 [C6] |

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 51 TRANS-Racemic mixture | 88a TRANS-single stereoisomer a | | 462 | 3.87 METHOD 1 | 7.71 [C1] |
| 51 TRANS-Racemic mixture | 88b TRANS-single stereoisomer b | | 462 | 3.87 METHOD 1 | 9.49 [C1] |
| 52 TRANS-Racemic mixture | 89a TRANS-single stereoisomer a | 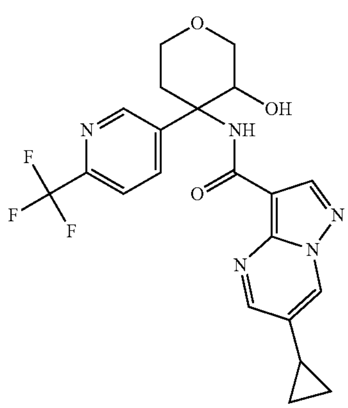 [SMILES: O=C(NC1(c2ccc(C(F)(F)F)nc2)CCOCC1O)c1cnn2cc(C3CC3)cnc12] | 448 | 3.60 METHOD 1 | 11.82 [C6] |

-continued
| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 52 TRANS- Racemic mixture | 89b TRANS- single stereoisomer b | 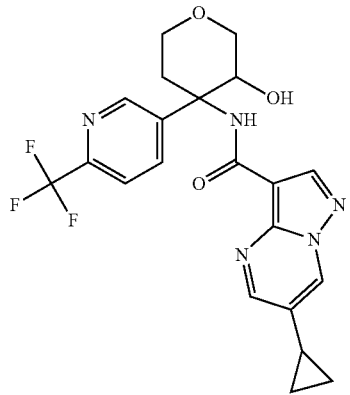 [SMILES: O=C(NC1(c2ccc(C(F)(F)F)nc2)CCOCC1O)c1cnn2cc(C3CC3)cnc12] | 448 | 3.60 METHOD 1 | 16 [C6] |
| 61 TRANS- Racemic mixture | 90a TRANS single stereoisomer a | 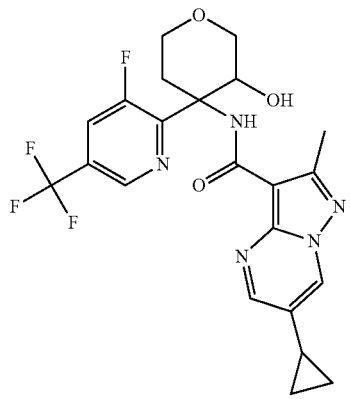 [SMILES: Cc1nn2cc(C3CC3)cnc2c1C(=O)NC1(c2ncc(C(F)(F)F)cc2F)CCOCC1O] | 480 | 4.22 METHOD 1 | 4.9 [C7] |
| 61 TRANS- Racemic mixture | 90b TRANS single stereoisomer b | 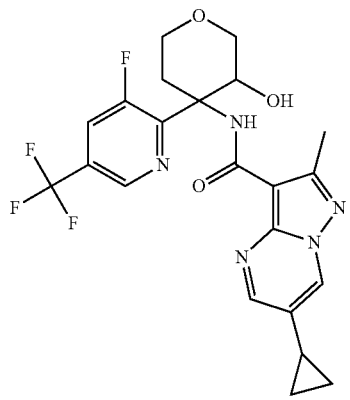 [SMILES: Cc1nn2cc(C3CC3)cnc2c1C(=O)NC1(c2ncc(C(F)(F)F)cc2F)CCOCC1O] | 480 | 4.22 METHOD 1 | 5.54 [C7] |

-continued

| Starting Racemic Mixture Ex. # | Ex. # | Structure | MS m/z [M + H]+ | R*t* (min) [LC-MS Method] | R*t* (min) [Chiral HPLC Method] |
|---|---|---|---|---|---|
| 62 TRANS-Racemic mixture | 91a TRANS single stereoisomer a | | 494 | 4.4 METHOD 1 | 6.68 [C1] |
| 62 TRANS-Racemic mixture | 91b TRANS single stereoisomer b | | 494 | 4.4 METHOD 1 | 12.94 [C1] |
| 58 TRANS/CIS 91/9 Racemic mixture | 92a CIS Single stereoisomer a | | 439 | 3.16 METHOD 10 | 4.76 [C1] |
| 58 TRANS/CIS 91/9 Racemic mixture | 92b CIS Single stereoisomer b | | 439 | 3.16 METHOD 10 | 8.24 [C1] |

-continued

| Starting Racemic Mixture Ex. # | Ex. # | Structure | MS m/z [M + H]+ | R$_t$ (min) [LC-MS Method] | R$_t$ (min) [Chiral HPLC Method] |
|---|---|---|---|---|---|
| 58 TRANS/ CIS 91/9 Racemic mixture | 93a TRANS Single stereoisomer a | | 439 | 3.16 METHOD 10 | 7.20 [C1] |
| 58 TRANS/ CIS 91/9 Racemic mixture | 93b TRANS Single stereoisomer b | | 439 | 3.16 METHOD 10 | 16.60 [C1] |

Relative Stereochemistry Assigned by NMR:

| Example | | Relative stereochemistry | 1H-NMR | NOE |
|---|---|---|---|---|
| 81a | | TRANS-single stereoisomer a | 1H NMR (500 MHz, DMSO-d6) δ ppm 2.40 (s, 3 H) 2.60-2.71 (m, 2 H) 3.63-3.69 (m, 1 H) 3.82 (br d, J = 11.98 Hz, 2 H) 4.03 (d, J = 11.74 Hz, 1 H) 4.08-4.11 (m, 1 H) 5.32 (d, J = 5.38 Hz, 1 H) 7.46-7.56 (m, 2 H) 7.73 (t, J = 7.51 Hz, 1 H) 8.34 (s, 1 H) 8.42 (s, 1 H) 8.81 (d, J = 2.20 Hz, 1 H) 9.17-9.19 (m, 1 | 8.42 (NH): 4.08; 4.03; 3.65; 3.82 5.32 (OH): 4.10; 3.70. |

-continued

| Example | Relative stereochemistry | 1H-NMR | NOE |
|---------|--------------------------|--------|-----|
| 82a | TRANS-single stereoisomer a | 1H NMR (500 MHz, DMSO-d6) δ ppm 0.93-1.06 (m, 4 H) 2.10 (tt, J = 8.38, 5.20 Hz, 1 H) 2.59-2.71 (m, 2 H) 3.66 (td, J = 11.68, 2.08 Hz, 1 H) 3.81 (br d, J = 11.25 Hz, 2 H) 4.03 (d, J = 11.86 Hz, 1 H) 4.09 (br d, J = 4.65 Hz, 1 H) 5.32 (d, J = 5.38 Hz, 1 H) 7.48 (d, J = 12.47 Hz, 1 H) 7.54 (dd, J = 8.31, 1.22 Hz, 1 H) 7.73 (t, J = 8.19 Hz, 1 H) 8.33 (s, 1 H) 8.40 (s, 1 H) 8.77 (d, J = 2.20 Hz, 1 H) 9.13 (s, 1 H) | 8.40 (NH): 4.09 5.32(OH): 4.09 |
| 83a | TRANS-single stereoisomer a | 1H NMR (500 MHz, DMSO-d6) δ ppm 1.10 (d, J = 2.57 Hz, 3 H) 2.41 (d, J = 0.73 Hz, 3 H) 2.52-2.57 (m, 1 H) 3.03 (br d, J = 4.40 Hz, 1 H) 3.56-3.58 (m, 1 H) 3.60-3.65 (m, 1 H) 3.75 (br dd, J = 11.49, 2.57 Hz, 1 H) 3.88 (d, J = 12.23 Hz, 1 H) 5.10 (s, 1 H) 7.46 (dd, J = 12.78, 1.41 Hz, 1 H) 7.53 (dd, J = 8.31, 1.34 Hz, 1 H) 7.67 (t, J = 8.25 Hz, 1 H) 8.39 (s, 1 H) 8.50 (s, 1 H) 8.83 (d, J = 2.08 Hz, 1 H) 9.23 (dd, J = 1.96, 1.10 Hz, 1 H) | 8.50 (NH): 1.10; 3.88; 2.53 5.10(OH): 3.57, 3.03 1.10 (Me): 8.50; 3.88; 2.53 |
| 84A | CIS-single stereoisomer a | 1H NMR (500 MHz, DMSO-d6) δ ppm 1.12 (s, 2 H) 2.36-2.47 (m, 3 H) 2.67-2.84 (m, 1 H) 2.98 (br d, J = 14.18 Hz, 1 H) 3.47 (d, J = 11.00 Hz, 1 H) 3.56 (br t, J = 11.98 Hz, 1 H) 3.75 (br dd, J = 11.37, 3.55 Hz, 1 H) 3.81 (d, J = 11.25 Hz, 1 H) 5.39 (s, 1 H) 7.46-7.55 (m, 2 H) 7.70 (t, J = 8.07 Hz, 1 H) 8.35 (s, 1 H) 8.77 (d, J = 1.96 Hz, 1 H) 8.96 (s, 1 H) 9.18 (dd, J = 2.08, 1.10 Hz, 1 H) | 8.96 (NH): 5.39; 2.73 5.39(OH): 8.96; 2.73 |

-continued

| Example | Relative stereochemistry | 1H-NMR | NOE |
|---|---|---|---|
| 84b | CIS-single stereoisomer b | 1H NMR (500 MHz, DMSO-d6) δ ppm 1.12 (s, 2 H) 2.36-2.47 (m, 3 H) 2.67-2.84 (m, 1 H) 2.98 (br d, J = 14.18 Hz, 1 H) 3.47 (d, J = 11.00 Hz, 1 H) 3.56 (br t, J = 11.98 Hz, 1 H) 3.75 (br dd, J = 11.37, 3.55 Hz, 1 H) 3.81 (d, J = 11.25 Hz, 1 H) 5.39 (s, 1 H) 7.46-7.55 (m, 2 H) 7.70 (t, J = 8.07 Hz, 1 H) 8.35 (s, 1 H) 8.77 (d, J = 1.96 Hz, 1 H) 8.96 (s, 1 H) 9.18 (dd, J = 2.08, 1.10 Hz, 1 H) | 8.96 (NH): 5.39; 2.73 5.39(OH): 8.96; 2.73 |
| 83b | TRANS-single stereoisomer b | 1H NMR (500 MHz, DMSO-d6) δ ppm 1.10 (d, J = 2.57 Hz, 3 H) 2.41 (d, J = 0.73 Hz, 3 H) 2.52-2.57 (m, 1 H) 3.03 (br d, J = 4.40 Hz, 1 H) 3.56-3.58 (m, 1 H) 3.60-3.65 (m, 1 H) 3.75 (br dd, J = 11.49, 2.57 Hz, 1 H) 3.88 (d, J = 12.23 Hz, 1 H) 5.10 (s, 1 H) 7.46 (dd, J = 12.78, 1.41 Hz, 1 H) 7.53 (dd, J = 8.31, 1.34 Hz, 1 H) 7.67 (t, J = 8.25 Hz, 1 H) 8.39 (s, 1 H) 8.50 (s, 1 H) 8.83 (d, J = 2.08 Hz, 1 H) 9.23 (dd, J = 1.96, 1.10 Hz, 1 H) | 8.50 (NH): 1.10; 3.88; 2.53 5.10(OH): 3.57, 3.03 1.10 (Me): 8.50; 3.88; 2.53 |
| 85a | CIS-single stereoisomer a | 1H NMR (500 MHz, DMSO-d6) δ ppm 0.94-1.07 (m, 4 H) 1.12 (s, 3 H) 2.12 (tt, J = 8.38, 5.20 Hz, 1 H) 2.72 (br t, J = 11.98 Hz, 1 H) 2.98 (br d, J = 13.69 Hz, 1 H) 3.47 (d, J = 11.25 Hz, 1 H) 3.56 (br t, J = 11.74 Hz, 1 H) 3.75 (br dd, J = 11.37, 3.30 Hz, 1 H) 3.81 (d, J = 11.25 Hz, 1 H) 5.38 (s, 1 H) 7.46-7.56 (m, 2 H) 7.70 (t, J = 8.07 Hz, 1 H) 8.35 (s, 1 H) 8.72 (d, J = 2.20 Hz, 1 H) 8.92 (s, 1 H) 9.12 (d, J = 2.20 Hz, 1 H) | 8.92 (NH): 5.38; 3.81; 3.56 5.38(OH): 8.92; 1.12 (Me): 3.47; 2.72 |

| Example | Relative stereochemistry | 1H-NMR | NOE |
|---|---|---|---|
| 86a | TRANS-single stereoisomer a | 1H NMR (500 MHz, DMSO-d6) δ ppm 0.95-1.07 (m, 5 H) 1.10 (d, J = 2.57 Hz, 2 H) 2.12 (tt, J = 8.44, 5.14 Hz, 1 H) 2.51-2.56 (m, 1 H) 3.03 (td, J = 12.65, 4.28 Hz, 1 H) 3.54-3.59 (m, 1 H) 3.62 (t, J = 11.25 Hz, 1 H) 3.75 (br dd, J = 11.25, 2.45 Hz, 1 H) 3.88 (d, J = 12.23 Hz, 1 H) 5.10 (s, 1 H) 7.46 (br d, J = 12.96 Hz, 1 H) 7.47-7.56 (m, 1 H) 7.59-7.71 (m, 1 H) 8.35-8.40 (m, 1 H) 8.48 (s, 1 H) 8.79 (d, J = 2.20 Hz, 1 H) 9.16 (d, J = 2.20 Hz, 1 H) | 8.48 (NH): 1.10; 3.88; 2.53 5.10(OH): 3.57; 3.03 1.10 (Me): 8.48; 3.88; 2.53 |
| 85b | CIS-single stereoisomer b | 1H N MR (500 MHz, DMSO-d6) δ ppm 0.94-1.07 (m, 4 H) 1.12 (s, 3 H) 2.12 (tt, J = 8.38, 5.20 Hz, 1 H) 2.72 (br t, J = 11.98 Hz, 1 H) 2.98 (br d, J = 13.69 Hz, 1 H) 3.47 (d, J = 11.25 Hz, 1 H) 3.56 (br t, J = 11.74 Hz, 1 H) 3.75 (br dd, J = 11.37, 3.30 Hz, 1 H) 3.81 (d, J = 11.25 Hz, 1 H) 5.38 (s, 1 H) 7.46-7.56 (m, 2 H) 7.70 (t, J = 8.07 Hz, 1 H) 8.35 (s, 1 H) 8.72 (d, J = 2.20 Hz, 1 H) 8.92 (s, 1 H) 9.12 (d, J = 2.20 Hz, 1 H) | 8.92 (NH): 5.38; 3.81; 3.56 5.38(OH): 8.92; 1.12 (Me): 3.47; 2.72 |
| 86b | TRANS-single stereoisomer b | 1H NMR (500 MHz, DMSO-d6) δ ppm 0.95-1.07 (m, 5 H) 1.10 (d, J = 2.57 Hz, 2 H) 2.12 (tt, J = 8.44, 5.14 Hz, 1 H) 2.51-2.56 (m, 1 H) 3.03 (td, J = 12.65, 4.28 Hz, 1 H) 3.54-3.59 (m, 1 H) 3.62 (t, J = 11.25 Hz, 1 H) 3.75 (br dd, J = 11.25, 2.45 Hz, 1 H) 3.88 (d, J = 12.23 Hz, 1 H) 5.10 (s, 1 H) 7.46 (br d, J = 12.96 Hz, 1 H) 7.47-7.56 (m, 1 H) 7.59-7.71 (m, 1 H) 8.35-8.40 (m, 1 H) 8.48 (s, 1 H) 8.79 (d, J = 2.20 Hz, 1 H) 9.16 (d, J = 2.20 Hz, 1 H) | 8.48 (NH): 1.10; 3.88; 2.53 5.10(OH): 3.57; 3.03 1.10 (Me): 8.48; 3.88; 2.53 |

| Example | | Relative stereochemistry | 1H-NMR | NOE |
|---|---|---|---|---|
| 87a | (structure: 4-[6-(trifluoromethyl)pyridin-3-yl]-4-amino-tetrahydropyran-3-ol coupled via amide to 6-methylpyrazolo[1,5-a]pyrimidine-3-carboxamide) | TRANS-single stereoisomer a | 1H NMR (400 MHz, DMSO-d6) δ ppm 2.41 (s, 3 H) 2.47 (m, 1 H) 2.63-2.74 (m, 1 H) 3.63-3.75 (m, 1 H) 3.76-3.87 (m, 2 H) 3.94 (br d, J = 4.89 Hz, 1 H) 4.08 (d, J = 11.74 Hz, 1 H) 5.30 (d, J = 5.67 Hz, 1 H) 7.83 (d, J = 8.22 Hz, 1 H) 8.10 (dd, J = 8.31, 1.66 Hz, 1 H) 8.38 (s, 1 H) 8.44 (s, 1 H) 8.82 (d, J = 1.96 Hz, 1 H) 8.85 (d, J = 1.76 Hz, 1 H) 9.20 (dd, J = 1.96, 0.98 Hz, 1 H) | 8.44 (NH): 4.08; 3.94; 2.47 5.30(OH): 3.81, 2.68 3.94 (CH): 8.44; 2.47 |
| 88a | (structure: 4-[6-(trifluoromethyl)pyridin-3-yl]-4-amino-tetrahydropyran-3-ol coupled via amide to 6-cyclopropyl-2-methylpyrazolo[1,5-a]pyrimidine-3-carboxamide) | TRANS-single stereoisomer a | 1H NMR (500 MHz, DMSO-d6) δ ppm 0.87-0.99 (m, 2 H) 1.00-1.06 (m, 2 H) 2.10 (tt, J = 8.47, 5.10 Hz, 1 H) 2.46 (s, 3 H) 2.51-2.53 (m, 1 H) 2.64-2.71 (m, 1 H) 3.64-3.72 (m, 1 H) 3.77-3.88 (m, 3 H) 4.10 (d, J = 11.49 Hz, 1 H) 5.29 (br s, 1 H) 7.84 (d, J = 8.07 Hz, 1 H) 8.08 (dd, J = 8.19, 2.08 Hz, 1 H) 8.65 (s, 1 H) 8.71 (d, J = 2.20 Hz, 1 H) 8.83 (d, J = 2.20 Hz, 1 H) 9.04 (d, J = 1.71 Hz, 1 H) | — |
| 89b | (structure: 4-[6-(trifluoromethyl)pyridin-3-yl]-4-amino-tetrahydropyran-3-ol coupled via amide to 6-cyclopropylpyrazolo[1,5-a]pyrimidine-3-carboxamide) | TRANS-single stereoisomer b | 1H NMR (500 MHz, DMSO-d6) δ ppm 0.92-1.07 (m, 4 H) 2.12 (tt, J = 8.47, 5.10 Hz, 1 H) 2.44-2.48 (m, 1 H) 2.64-2.72 (m, 1 H) 3.65-3.73 (m, 1 H) 3.76-3.86 (m, 2 H) 3.92 (br d, J = 5.87 Hz, 1 H) 4.09 (d, J = 11.49 Hz, 1 H) 5.29 (d, J = 6.11 Hz, 1 H) 7.83 (d, J = 8.07 Hz, 1 H) 8.10 (dd, J = 8.19, 2.08 Hz, 1 H) 8.37 (s, 1 H) 8.43 (s, 1 H) 8.77 (d, J = 2.20 Hz, 1 H) 8.84 (d, J = 2.20 Hz, 1 H) 9.14 (d, J = 2.20 Hz, 1 H) | — |

The invention claimed is:

1. A method of treating cognitive impairment in bipolar disorder or cognitive impairment in schizoaffective disorder in a subject comprising administering to the subject an effective amount of a compound of formula (I)

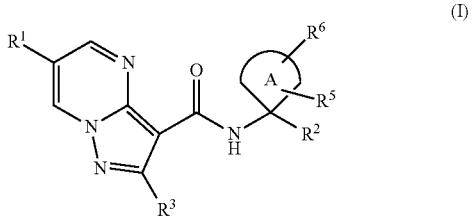

(I)

wherein
A is selected from the group $A^a$ consisting of

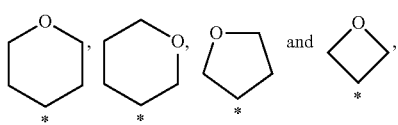

wherein above mentioned groups are substituted with one $R^5$ and one $R^6$;
$R^1$ is selected from the group $R^{1a}$ consisting of
halogen, $C_{1-3}$-alkyl- and $C_{3-6}$-cycloalkyl-
wherein the above mentioned $C_{1-3}$-alkyl-, and $C_{3-6}$-cycloalkyl-groups may optionally be substituted with 1 to 5 substituents independently selected from the group consisting of halogen, NC— and HO—;
$R^2$ is selected from the group $R^{2a}$ consisting of
aryl and heteroaryl,
wherein the above mentioned aryl and heteroaryl-groups may optionally be substituted with 1 to 5 substituents $R^4$;
$R^3$ is selected from the group $R^{3a}$ consisting of
H— and $C_{1-3}$-alkyl-,
wherein the above mentioned $C_{1-3}$-alkyl-groups may optionally be substituted with 1 to 7 substituents independently from each other selected from the group consisting of halogen;
$R^4$ is independently from each other selected from the group $R^{4a}$ consisting of
halogen, NC—, HO—, $C_{1-4}$-alkyl- and $C_{1-3}$-alkyl-O—
wherein the above mentioned $C_{1-4}$-alkyl- and $C_{1-3}$-alkyl-O-groups may optionally be substituted with 1 to 5 substituents independently selected from the group consisting of HO— and F—;
$R^5$ is selected from the group $R^{5a}$ consisting of
H—, halogen, NC—, HO— and $C_{1-3}$-alkyl-,
wherein the above mentioned $C_{1-3}$-alkyl-group may optionally be substituted with 1 to 5 substituents independently selected from the group consisting of HO— and F—
or $R^5$ and $R^6$ together form an group O=;
$R^6$ is selected from the group $R^{6a}$ consisting of
H—, halogen, NC—, HO— and $C_{1-3}$-alkyl-,
wherein the above mentioned $C_{1-3}$-alkyl-group may optionally be substituted with 1 to 5 substituents independently selected from the group consisting of HO— and F—
or $R^5$ and $R^6$ together form a group O=;
or a pharmaceutically acceptable salt thereof.

2. The method of claim 1, wherein
A is selected from the group $A^b$ consisting of

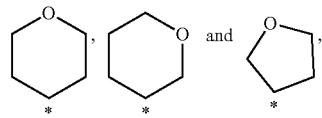

wherein above mentioned groups are substituted with one $R^5$ and one $R^6$;
or a pharmaceutically acceptable salt thereof.

3. The method of claim 1, wherein
A is selected from the group $A^c$ consisting of

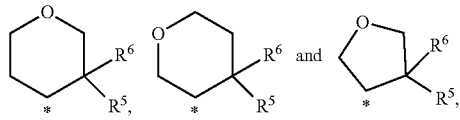

or a pharmaceutically acceptable salt thereof.

4. The method of claim 1, wherein
A is selected from the group $A^d$ consisting of

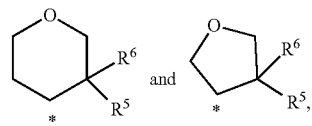

or a pharmaceutically acceptable salt thereof.

5. The method of claim 1, wherein
$R^1$ is selected from the group $R^{1b}$ consisting of
F—, Cl—, $C_{1-3}$-alkyl- and $C_{3-6}$-cycloalkyl-,
wherein the above mentioned $C_{1-3}$-alkyl- and $C_{3-6}$-cycloalkyl-groups may optionally be substituted with 1 to 3 substituents independently selected from the group consisting of F—,
or a pharmaceutically acceptable salt thereof.

6. The method of claim 1, wherein
$R^1$ is selected from the group $R^{1c}$ consisting of
F—, $H_3C$— and cyclopropyl-,
or a pharmaceutically acceptable salt thereof.

7. The method of claim 1, wherein
$R^2$ is selected from the group $R^{2b}$ consisting of
quinolinyl, phenyl and pyridynyl,
wherein the above mentioned quinoline, phenyl and pyridyl-groups may optionally be substituted with 1 to 5 substituents $R^4$,
or a pharmaceutically acceptable salt thereof.

8. The method of claim 1, wherein
$R^2$ is selected from the group $R^{2c}$ consisting of
phenyl and pyridyl,
wherein the above mentioned phenyl and pyridyl-groups may optionally be substituted with 1 to 2 substituents $R^4$,
or a pharmaceutically acceptable salt thereof.

9. The method of claim 1, wherein
$R^3$ is selected from the group $R^{3b}$ consisting of
H—, $H_3C$—, $F_3C$—, $F_2HC$—, $FH_2C$— and $F_3C$—,
or a pharmaceutically acceptable salt thereof.

10. The method of claim 1, wherein $R^4$ is independently from each other selected from the group $R^{4b}$ consisting of halogen, $C_{1-4}$-alkyl- and $C_{1-3}$-alkyl-O— wherein the above mentioned $C_{1-4}$-alkyl- and $C_{1-3}$-alkyl-O-groups may optionally be substituted with 1 to 5 substituents independently selected from the group consisting of HO—, and F—, or a pharmaceutically acceptable salt thereof.

11. The method of claim 1, wherein $R^5$ is selected from the group $R^{5b}$ consisting of H—, HO— and $C_{1-2}$-alkyl-, wherein the above mentioned $C_{1-2}$-alkyl-group may optionally be substituted with 1 to 5 F—, or $R^5$ and $R^6$ together form an group O=, or a pharmaceutically acceptable salt thereof.

12. The method of claim 1, wherein $R^6$ is selected from the group $R^{6b}$ consisting of H— and $C_{1-2}$-alkyl-, wherein the above mentioned $C_{1-2}$-alkyl-group may optionally be substituted with 1 to 5 F—, or $R^5/R^6$ together form a group O=, or a pharmaceutically acceptable salt thereof.

13. The method of claim 1, wherein the compound of formula (I) is selected from the group consisting of

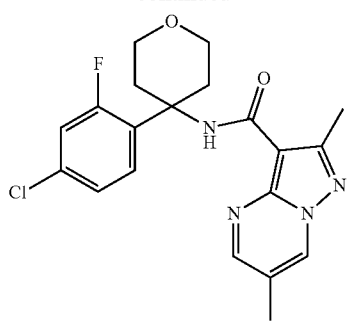

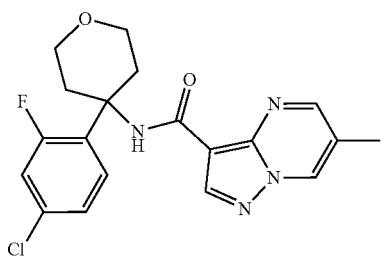

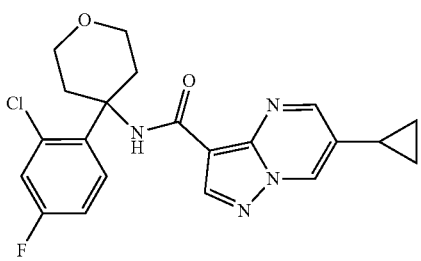

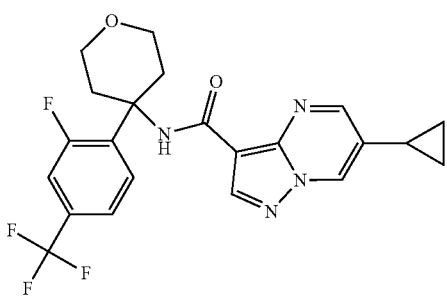

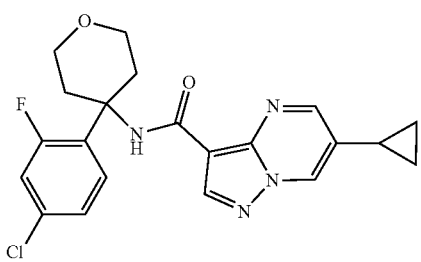

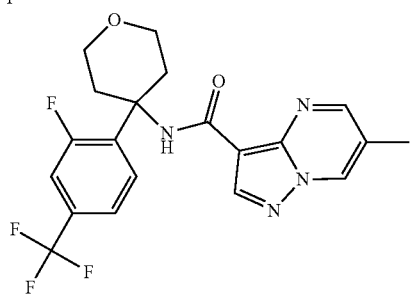

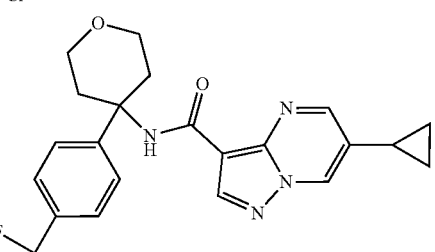

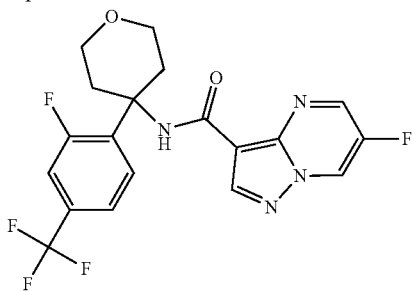

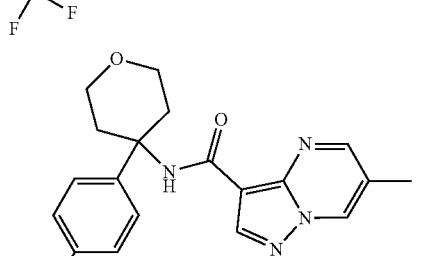

-continued
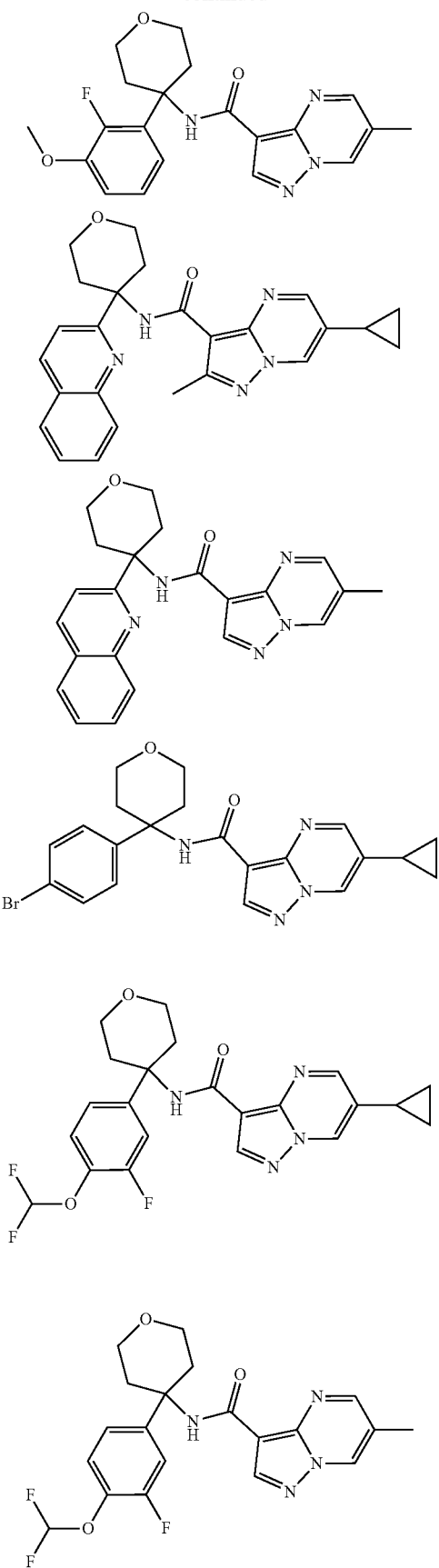
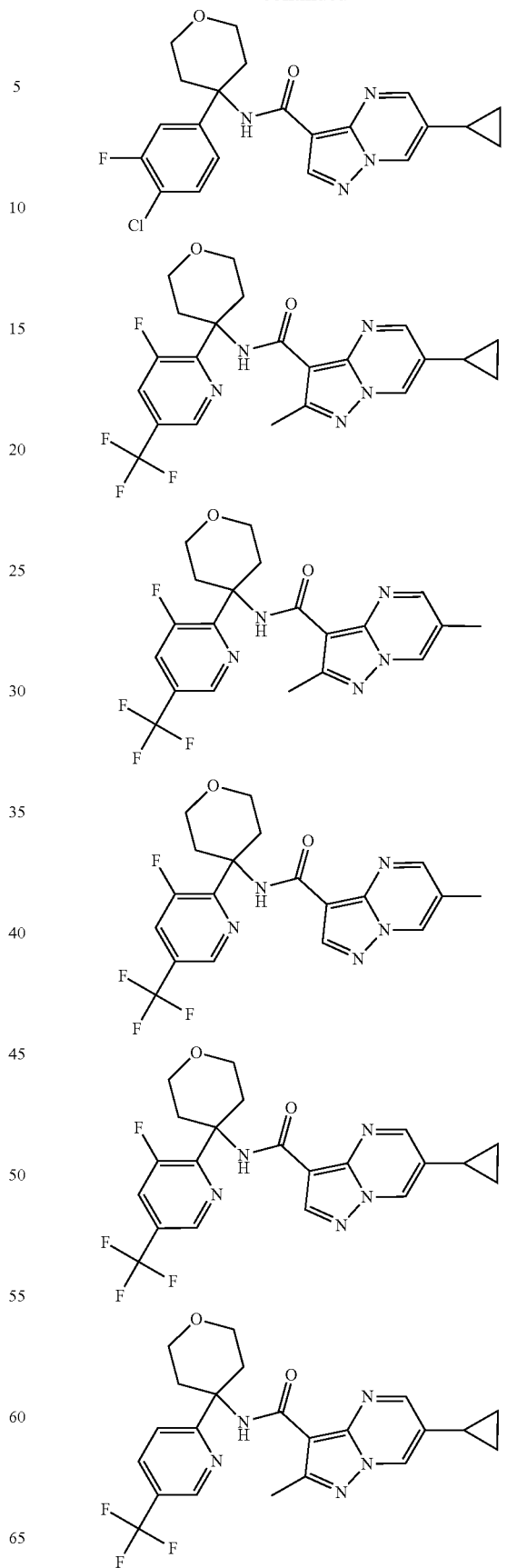

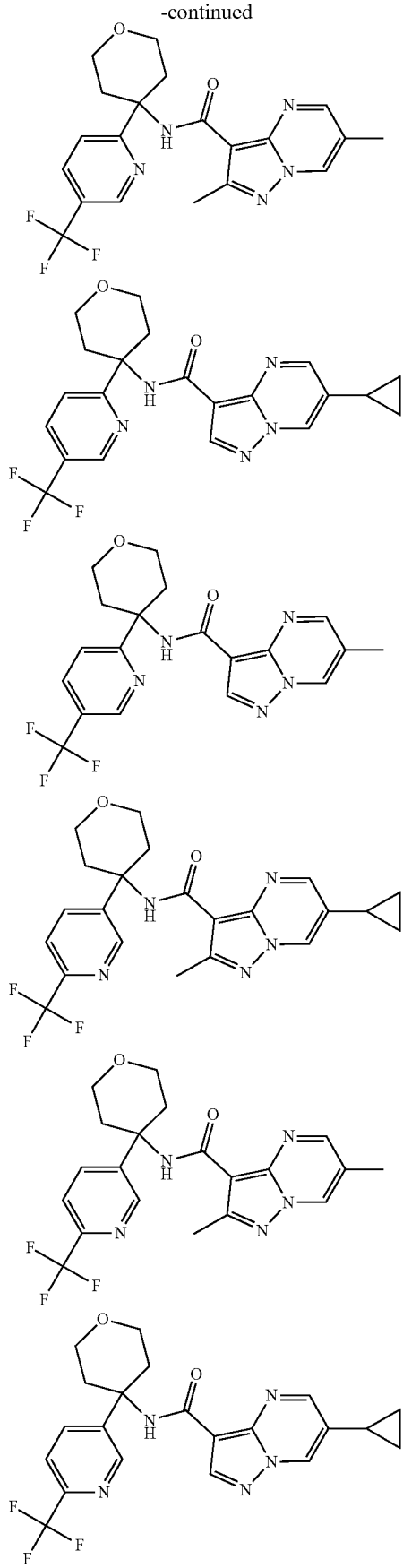
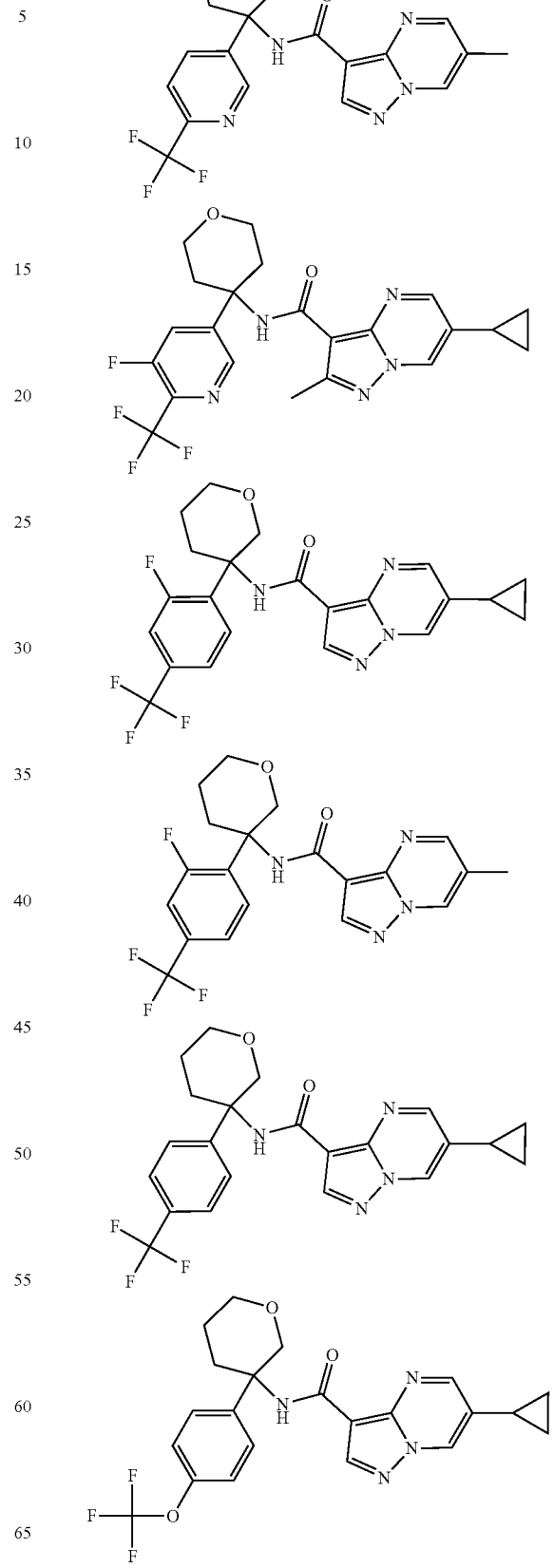

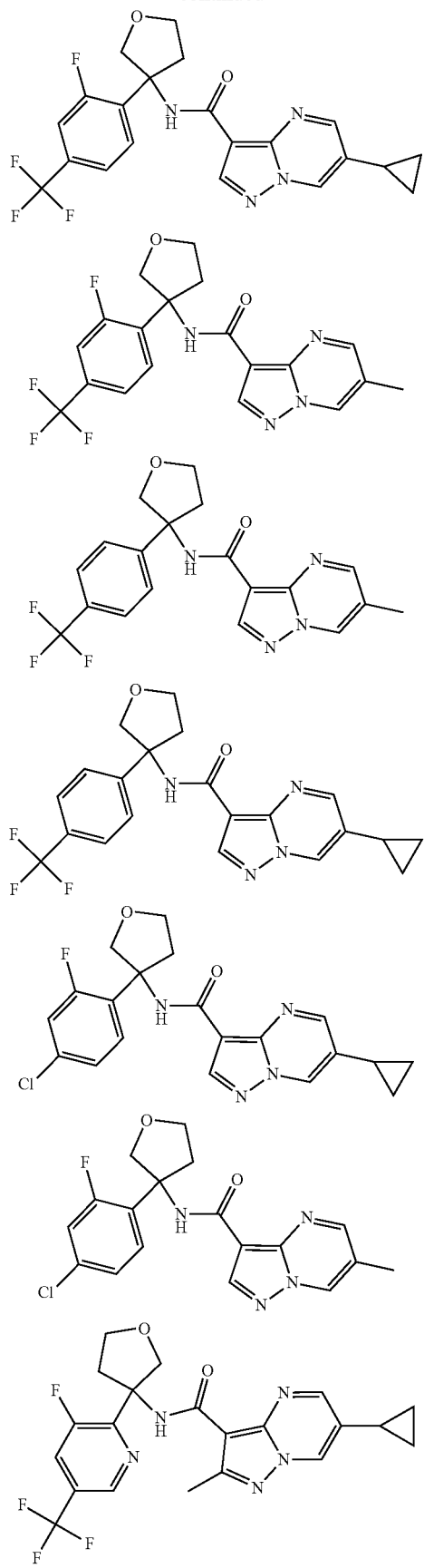
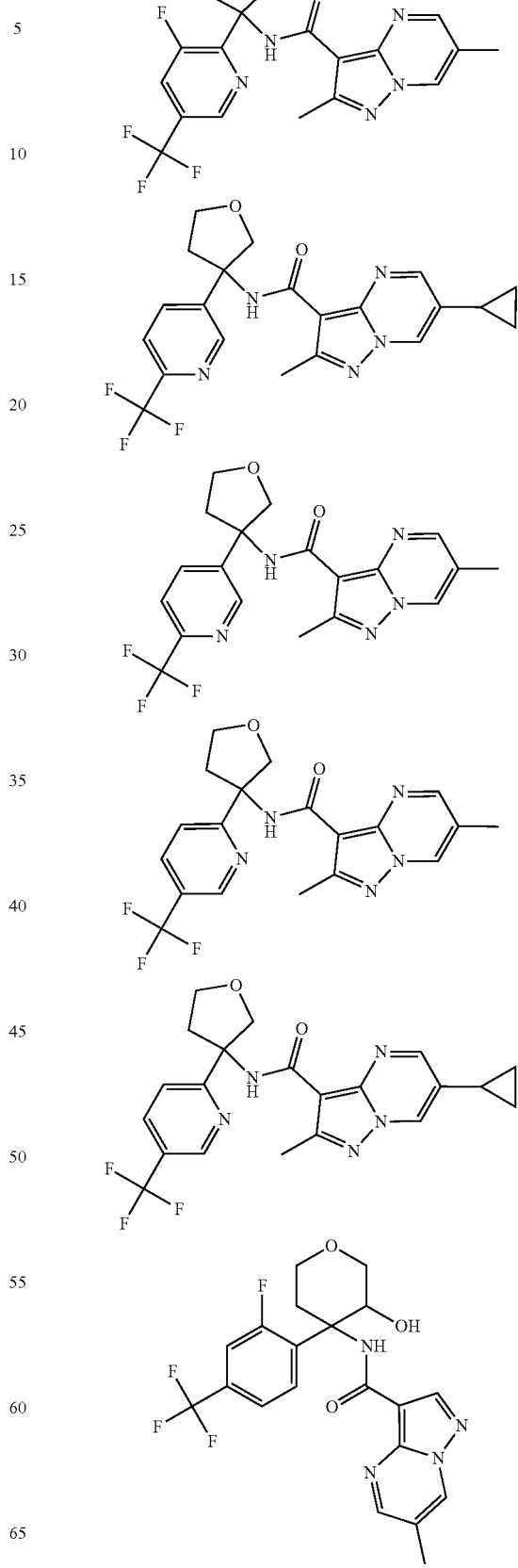

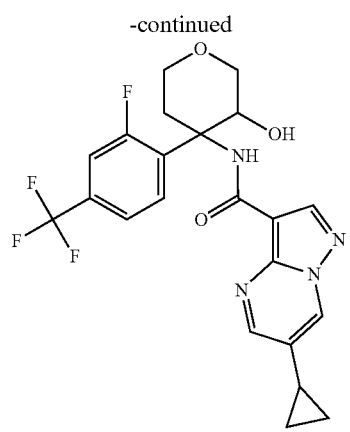
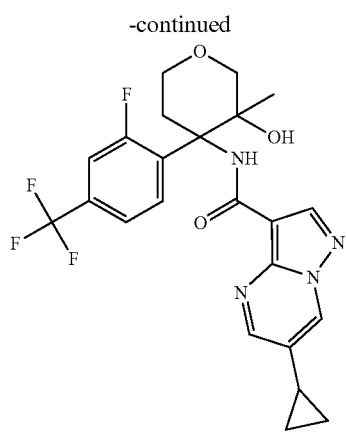
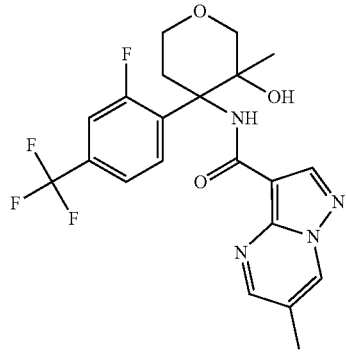
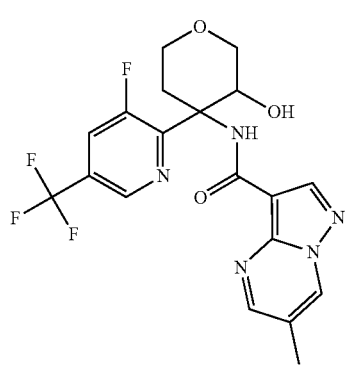
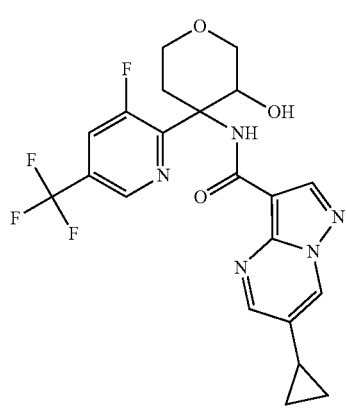

-continued
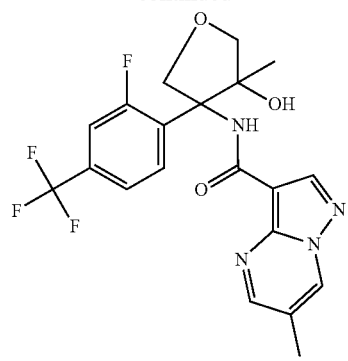
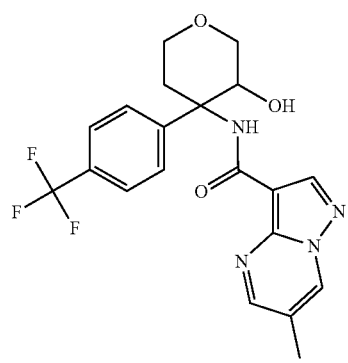
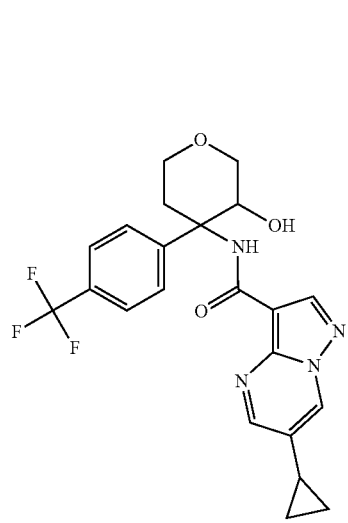
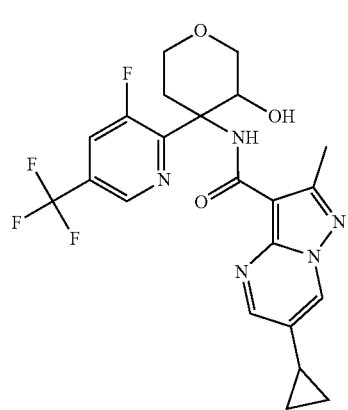
-continued
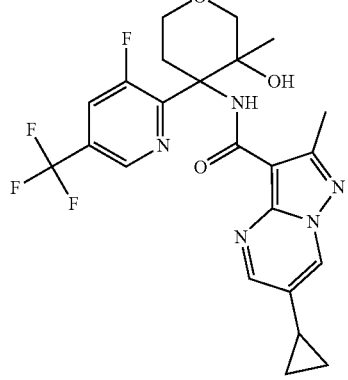
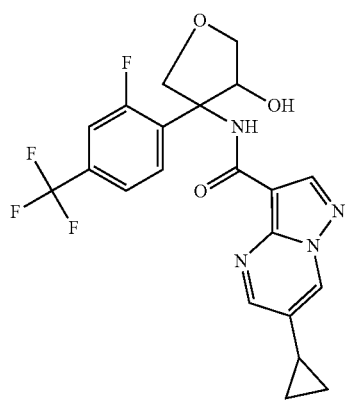
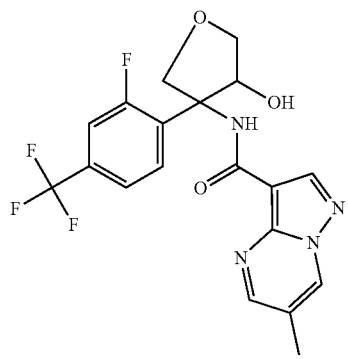
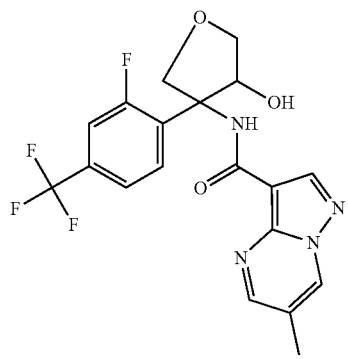

-continued
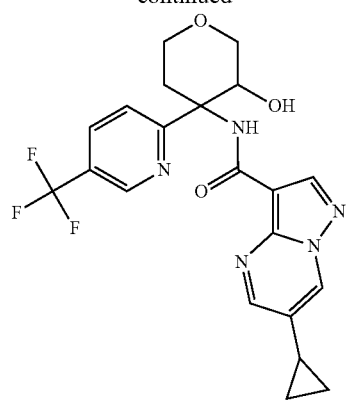
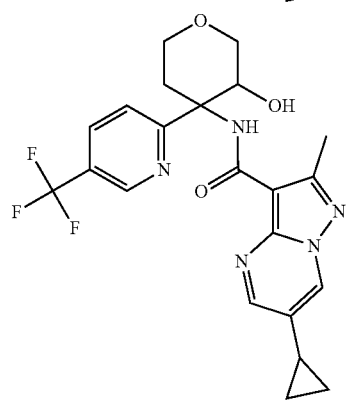
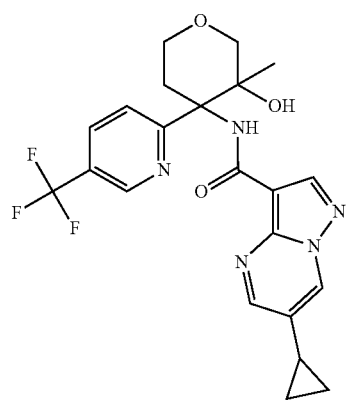
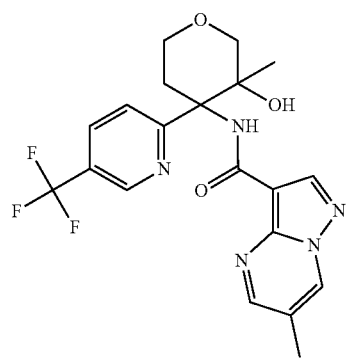
-continued
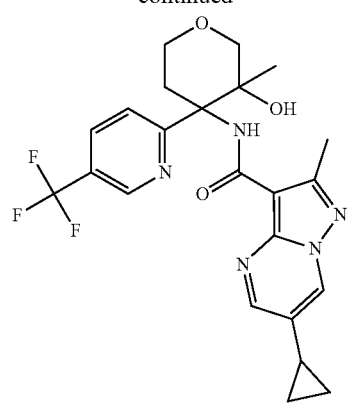
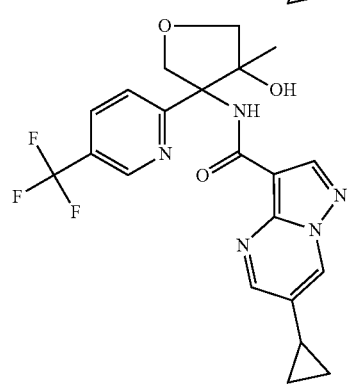
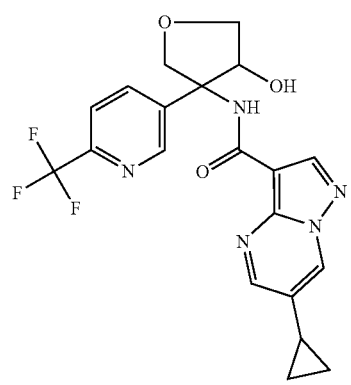
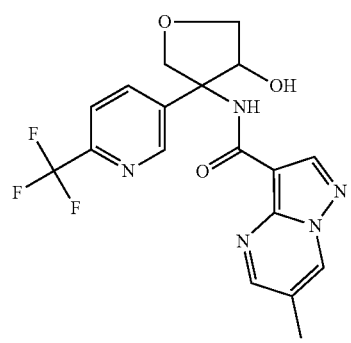

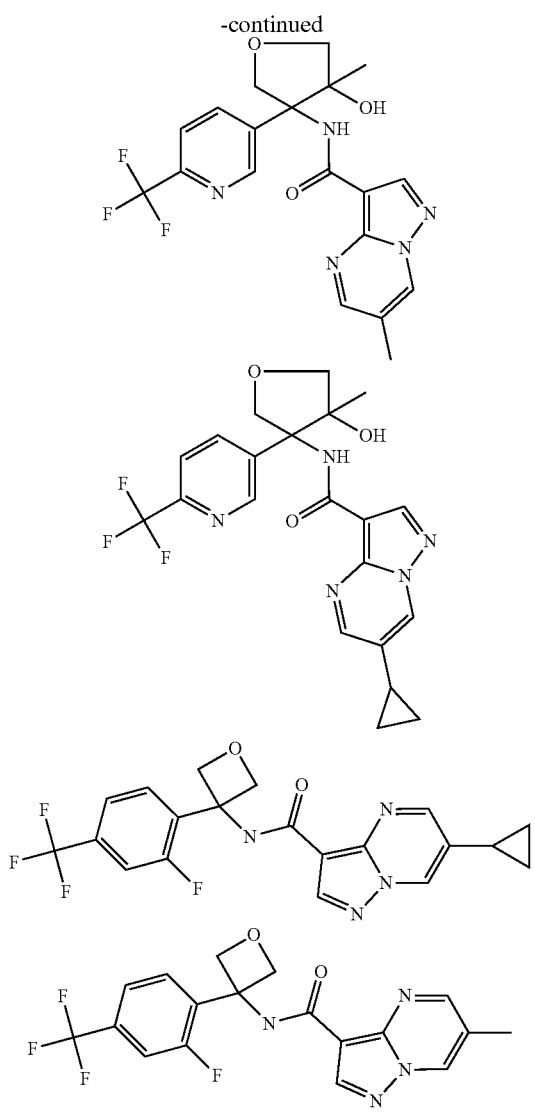
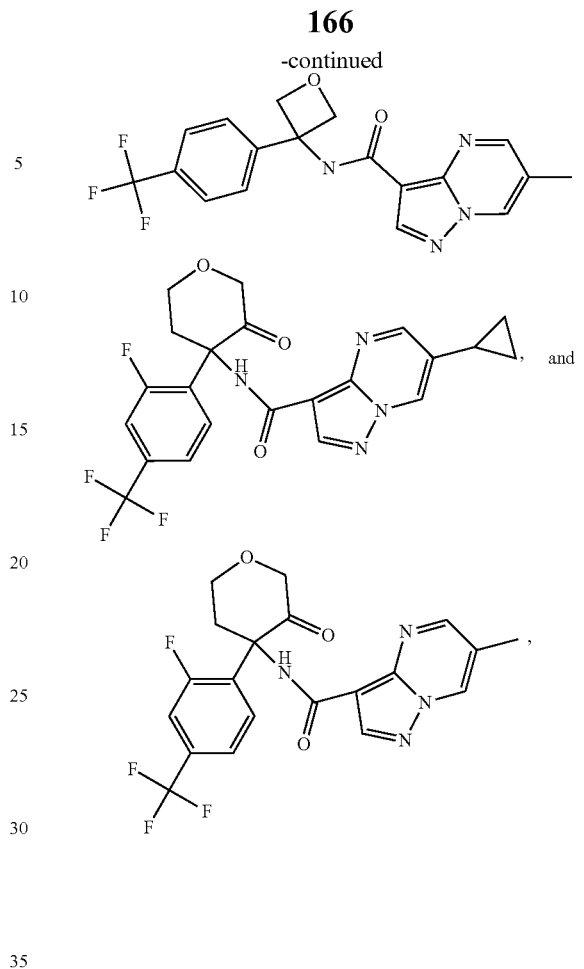
or a pharmaceutically acceptable salt thereof.
14. The method of claim 1, for treating cognitive impairment in bipolar disorder.
15. The method of claim 1, for treating cognitive impairment in schizoaffective disorder.
* * * * *